(12) United States Patent
Tindale et al.

(10) Patent No.: US 9,382,190 B2
(45) Date of Patent: Jul. 5, 2016

(54) CONTINUOUS PROCESS FOR THE CARBONYLATION OF ETHYLENE

(71) Applicant: Lucite International UK Limited, Southampton (GB)

(72) Inventors: Neil Tindale, Wilton (GB); Graham Ronald Eastham, Wilton (GB)

(73) Assignee: LUCITE INTERNATIONAL UK LIMITED, South Hampton (GB)

( * ) Notice: Subject to any disclaimer, the term of this patent is extended or adjusted under 35 U.S.C. 154(b) by 0 days.

(21) Appl. No.: 14/364,718

(22) PCT Filed: Dec. 20, 2012

(86) PCT No.: PCT/GB2012/053204
§ 371 (c)(1),
(2) Date: Jun. 12, 2014

(87) PCT Pub. No.: WO2013/093472
PCT Pub. Date: Jun. 27, 2013

(65) Prior Publication Data
US 2015/0099896 A1 Apr. 9, 2015

(30) Foreign Application Priority Data
Dec. 21, 2011 (GB) .................................. 1122054.8

(51) Int. Cl.
C07C 69/00 (2006.01)
C07C 67/38 (2006.01)
C07C 67/54 (2006.01)

(52) U.S. Cl.
CPC ................. *C07C 67/38* (2013.01); *C07C 67/54* (2013.01)

(58) Field of Classification Search
CPC .......... C07C 67/38; C07C 67/54; C07C 69/24
See application file for complete search history.

(56) References Cited

U.S. PATENT DOCUMENTS 4,262,138 A 4/1981 Gelbein

FOREIGN PATENT DOCUMENTS

| EP | 2 243 549 A1 | 10/2010 |
| EP | 2243549 | * 10/2010 |
| WO | 98 41495 A1 | 9/1998 |
| WO | 2007 020379 A1 | 2/2007 |
| WO | 2011 073655 A1 | 6/2011 |

OTHER PUBLICATIONS

M. T. Tham (Basic Distillation Equipment and Operation, 2009).*
M. T. Tham (Basic Distillation Equipment and Operation, 2009)M. T. Tham (Basic Distillation Equipment and Operation, 2009).*
Pilling et al. (Choosing Trays and Packings for Distillation, 2009).*
International Search Report dated Mar. 27, 2013 for International Patent Application No. PCT/GB2012/053204.
Chinese Office Action for 201280063887.8 dated Nov. 25, 2015.

* cited by examiner

*Primary Examiner* — Yevegeny Valenrod
*Assistant Examiner* — Blaine G Doletski
(74) *Attorney, Agent, or Firm* — Shumaker, Loop & Kendrick, LLP

(57) ABSTRACT

A continuous process for the production of an alkyl ester product is described. The process includes the steps of carbonylating ethylene with carbon monoxide in the presence of C1-6 alkanol co-reactant to form the alkyl ester product. The carbonylation takes place in the presence of a catalyst system that includes (a) a bidentate ligand, (b) a catalytic metal selected from a group 8, 9 or 10 metal or a compound thereof, and (c) a sulphonic acid capable of forming an acid alkyl ester with the C1-6 alkanol. The process includes the step of separating the alkyl ester product from a carbonylated crude product stream by treatment effective to vaporizing the alkyl ester product in a single stage flash distillation column and providing a purified alkyl ester product stream separated from the bidentate ligand and catalytic metal.

15 Claims, 3 Drawing Sheets

CONTINUOUS PROCESS FOR THE CARBONYLATION OF ETHYLENE

CROSS-REFERENCE TO RELATED APPLICATION

This U.S. National Stage Application claims priority from PCT/GB2012/053204 filed Dec. 20, 2012, which claims priority from GB 1122054.8 filed Dec. 21, 2011, the entirety of which are incorporated herein by reference.

TECHNICAL FIELD AND BACKGROUND OF THE INVENTION

This invention relates to an improved continuous process for the carbonylation of ethylene.

The carbonylation of ethylenically unsaturated compounds using carbon monoxide in the presence of an alcohol or water and a catalyst system comprising a group 6, 8, 9 or 10 metal, for example, palladium, and a phosphine ligand, for example an alkyl phosphine, cycloalkyl phosphine, aryl phosphine, pyridyl phosphine or bidentate phosphine, has been described in numerous European patents and patent applications, for example EP-A-0055875, EP-A-04489472, EP-A-0106379, EP-A-0235864, EP-A-0274795, EP-A-0499329, EP-A-0386833, EP-A-0441447, EP-A-0489472, EP-A-0282142, EP-A-0227160, EP-A-0495547 and EP-A-0495548. In particular, EP-A-0227160, EP-A-0495547 and EP-A-0495548 disclose that bidentate phosphine ligands provide catalyst systems which enable high reaction rates to be achieved. C3 alkyl bridges between the phosphorus atoms are exemplified in EPO495548 together with tertiary butyl substituents on the phosphorus. WO96/19434, WO 01/68583, WO 98/42717, WO 03/070370, WO 04/103948 and WO 05/082830 relate to developments in these bidentate ligands and their applications.

In particular, WO96/19434 relates to an improved carbonylation of ethylene in the presence of methanol co-reactant to produce methyl propionate in the presence of a bidentate phosphine ligand and a palladium catalyst. The reaction is advantageously carried out in the presence of an acid such as a sulphonic acid. It is advantageous to include acid in the catalyst feed because this allows a more stable metal(0) compound to be used so that the catalytically active metal cation can be generated in situ by the presence of acid prior to the reactor. Unfortunately, the design of a continuous process is hindered by the presence of this acid because whereas the reactants are consumed by the reaction and the palladium and the ligand catalyst eventually decompose in the reactor, the acid will tend to accumulate in the reactor and potentially lead to a steady and unwanted pH rise. The catalyst system can be removed in the product stream, be separated subsequently and neutralised before recycling but this leads to potential contamination of the catalyst system with base salts. Neutralisation of the product stream with base followed by removal of the metal and ligand is an even more complex series of separation steps. Accordingly, it is necessary to address the problem of acid build up in the reactor without contaminating the catalyst system or the product.

BRIEF SUMMARY OF THE INVENTION

Surprisingly, it has now been found that acid can be surprisingly removed and also that an acid treatment step can be carried out at an unexpected stage of the continuous process.

According to a first aspect of the present invention there is provided a continuous process for the production of an alkyl ester product comprising the steps of:— carbonylating ethylene with carbon monoxide in the presence of $C_{1-6}$ alkanol co-reactant to form the said alkyl ester product, wherein the carbonylation takes place in the presence of a catalyst system comprising (a) a bidentate ligand, (b) a catalytic metal selected from a group 8, 9 or 10 metal or a compound thereof, and (c) a sulphonic acid capable of forming an acid alkyl ester with the $C_{1-6}$ alkanol, the process including the step of separating the formed alkyl ester product from a carbonylated crude product stream by suitable treatment effective to vaporise the alkyl ester product in a single stage flash distillation column and provide a purified alkyl ester product stream separated from the said bidentate ligand and catalytic metal, wherein the said distillation column includes further separation means effective to provide further separation of the product.

Typically, the further separation means is packing in or associated with the upper part of the flash distillation column. However, the further separation may also be provided by trays. Preferably, the packing is structured packing although random packing may also be utilised.

Preferably, the packing provides further theoretical plates such as between 0.01 and 5 further theoretical plates, more preferably, between 0.1 and 2 further plates, most preferably, between 0.2 and 3 further theoretical plates for separation. Generally, the packing occupies between 5 and 40% of the column and is located at the upper end thereof, more preferably, between 10 and 25% of the column at the upper end thereof.

Advantageously, the packing not only prevents carry over of catalyst but preferentially separates the acid component of the catalyst from the metal and ligand component allowing a small amount of acid carry over. This small carry over is sufficient to prevent build up of acid in the reactor during a continuous catalyst fed process.

DETAILED DESCRIPTION OF THE INVENTION

By the term "further" in "further theoretical plates" and "further separation means" is meant in addition to the separation provided by the single stage flash distillation column per se.

A suitable structured packing is the Sulzer range, such as the Mellapak products, one example is the Mellapak Plus 202.Y product. However, other types of structured packing are available to the skilled person.

In addition, it is preferable to introduce a small amount of reflux into the flash distillation column. Typically, 0.1 to 5% w/w reflux is provided. A suitable reflux component is a separate stream of the alkyl ester product of the reaction or a mixture thereof, for instance, with the $C_{1-6}$ alkanol of the reaction.

Preferably, the purified alkyl ester product stream is subsequently subjected to a sulphonic acid treatment step effective to separate the said acid from or neutralise the said acid in the said purified alkyl ester product stream.

Preferably, the sulphonic acid treatment step is either carried out with base to at least partly, more preferably, fully neutralise the acid in the said purified product stream or is carried out by suitable heat and/or pressure treatment effective to preferentially vaporise the alkyl ester product from the purified stream such as by distillation thus leaving the acid and its ester as a heavy fraction. The sulphonic acid treatment may be carried out by separation at approximately atmospheric pressure and with a re-boiler operating at or just above the boiling point of the alkyl ester product, for instance, at 0-5° C., more preferably, 0-3° C. above the boiling point. In the case of methyl propionate, the re-boiler may be at 79-82° C. The pressure range may be from 0.9-1.1 barg. However, it will be appreciated by those skilled in the art that the same separations can be carried out at different pressures as long as the temperature is adjusted accordingly or vice versa.

The formed alkyl ester product may include a proportion of $C_{1-6}$ alkanol co-reactant. This may be separated at suitable temperatures and pressures from the formed alkyl ester product as a light or heavy fraction or, if one is formed, as an azeotrope. The alkanol co-reactant separation is preferably carried out before any acid treatment step.

Advantageously, the invention also relates to the surprising discovery of small, ppm levels, such as less than 10 ppm, more typically, less than 5 ppm, most typically less than 3 or 2 ppm of sulphonic acid in the purified alkyl ester product stream. Such levels of acid would not normally be noticed and are also surprising because the boiling temperatures of the sulphonic acids are considerably higher than the vaporisation temperatures of the alkyl ester products. Without being bound by theory, one possible explanation may be that in a continuous process, in the presence of an alcohol, the sulphonic acid may form a lower boiling alkyl ester of the acid in equilibrium with the sulphonic acid and even though the acid alkyl ester still boils at considerably higher temperatures than the alkyl ester product of the invention, the corresponding vapour pressure increase may be sufficient to cause a small, ppm amount as referred to above to vaporise with the alkyl ester product during the crude product stream treatment step. The surprising discovery is only generally possible by concentrating, for instance by 10, 20 or 50 fold, the product stream to raise the level of acid to measurable levels. The surprising presence of small amounts of the acid and its alkyl ester in the purified alkyl ester product stream allows post reactor treatment of the relatively small amount of acid without contamination of the reaction medium, catalyst, recycle streams or subsequent processes that use the alkyl ester product thus providing a surprisingly convenient means to avoid neutralisation of the catalyst system and prevent acid build up in the reaction medium in the continuous process. Acid build up would otherwise provide an unacceptable corrosion source in the reactor. In particular, this treatment avoids the necessity to carry out periodic acid purges of the reactor which would otherwise be necessary to prevent acid build up in the reaction medium or to remove contaminated catalyst and/or base salts. In this regard, it should also be appreciated that the effective solvent in a continuous process is the product of the reaction so that any recycle of the product containing the trace acid will also act as a source of acid.

It will be appreciated by the skilled person that in a continuous process acid build up is caused by the reactants and catalyst system being fed continuously or periodically into the reactor to maintain the reaction at the predetermined rate. The catalyst components can generally be fed at the rate of decomposition thereof to maintain catalyst efficacy but the acid component of the catalyst system unlike the ligand and metal components will not generally decompose thus providing a potential problem of acid build up in the reaction medium. Alternatively, periodic or continuous neutralisation of the catalyst system will cause build up of undesirable base salts.

One possibility is to neutralise the low level of acid in a subsequent process which uses the purified alkyl ester product. One such process is the catalytic conversion of methyl propionate (MEP) to MMA using formaldehyde. Advantageously, in this process, the source of formaldehyde is generally formalin formaldehyde:methanol:water in the ratio 35 to 55%:0.05 to 18%:42 to 53% by weight. The presence of methanol and water means that the base can be easily dissolved therein before contacting the formalin with the alkyl ester. In addition this prevents any reaction of the acid with the formalin. The salt and any excess base can be removed by evaporation of the lighter organic components.

The amount of base added to the sulphonic acid containing alkyl ester product can vary depending upon the amount of acid in the purified alkyl ester product and the amount of neutralisation required. However, it may be typically between 1 and 3 times the molar level of the sulphonic acid, typically, between 1 and 2 times the molar level of sulphonic acid.

Acid

Preferably, a sulphonic acid is selected to have a pKa less than 6 measured in dilute aqueous solution at 25° C. The pKa is preferably less than about 4 measured in dilute aqueous solution at 18° C. Particularly preferred acids have a pKa of less than 2 measured in dilute aqueous solution at 25° C. but in the case of some substrates such as dienes a pKa of between 2-6 measured in dilute aqueous solution at 18° C. is preferred. Suitable sulphonic acids may be selected from the acids listed below.

Suitable acids comprise those having anions which will weakly coordinate to the catalytic metal. Suitable acids may be selected from methane sulphonic acid, chlorosulphonic acid, fluorosulphonic acid, trifluoromethane sulphonic acid, benzene sulphonic acid, naphthalene sulphonic acid, toluene sulphonic acid (e.g. p-toluene sulphonic acid), t-butyl sulphonic acid, 2-hydroxypropane sulphonic acid, $C_2$-$C_{12}$ alkanesulphonic acid, camphor sulphonic acid and 1 and 2-adamantanesulphonic acid. In the present invention, the more preferred acids are methane sulphonic acid, $C_2$-$C_8$ alkanesulphonic acid, benzene sulphonic acid, t-butyl sulphonic acid and toluene sulphonic acid, the most preferred acid being methane sulphonic acid.

Preferably, the sulphonic acid is added to the catalyst system prior to the catalyst being contacted with the reactants.

Addition of the acids to the catalyst system provides acidic reaction conditions which are favourable to TON. It also provides a source of sulphonate anions which coordinate with the group 8, 9 or 10 metal.

For the purposes of the invention herein, the pKa may be determined by suitable techniques known to those skilled in the art.

In the carbonylation reaction the quantity of acid present can be expressed as the molar ratio of Group 8, 9 or 10 metal/compound to acid and may be from 1:1 to 1:4000, more preferably, 1:2 to 1:1000, most preferably, 1:5 to 1:200, especially, 1:10 to 1:200.

Typically, the alkyl ester product is vaporised from within the crude product stream by effective heat treatment in the flash distillation column at a suitable temperature and pressure effective to vaporise the product and/or its azeotrope with other components present. For example in the case of methyl propionate product the heat treatment may for instance be in the range 60-120° C., more typically, 65-95° C. Typically, the treatment is carried out at less than 130° C., more typically, less than 110° C., most typically, at less than 100° C. Generally, the pressure during the treatment step will be effective at between 80-220 KPa, more typically, 100-200 KPa, most typically, 130-180 KPa in the above temperature ranges.

It is particularly surprising that any acid is removed by the said treatment of the alkyl ester crude product stream because the sulphonic acids have a boiling point in the range 300-400° C. and often decompose before they can boil. Furthermore, the bulk of the catalyst including the sulphonic acid is generally recovered as a heavy fraction after the said crude product single stage flash column treatment step. The loss of acid at this stage would be too low to be monitored directly. The catalyst system in the heavy fraction is recycled back to the reaction medium in the reactor.

Typically, the alkyl ester product is vaporised from within the crude product stream together with less than 5 ppm sulphonic acid and/or alkyl ester thereof, more typically, less than 5 ppm thereof, most typically, less than 2 ppm thereof.

Typically, the bidentate ligand is a bidentate ligand of general formula (I)

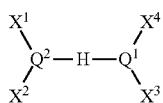

I wherein H is a bivalent organic bridging group with 1-6 atoms in the bridge;
the groups $X^1$, $X^2$, $X^3$ and $X^4$ independently represent univalent radicals of up to 30 atoms, optionally having at least one tertiary carbon atom via which the group is joined to the $Q^1$ or $Q^2$ atom, or $X^1$ and $X^2$ and/or $X^3$ and $X^4$ together form a bivalent radical of up to 40 atoms, optionally having at least two tertiary carbon atoms via which the radical is joined to the $Q^1$ and/or $Q^2$ atom; and
$Q^1$ and $Q^2$ each represent phosphorus, arsenic or antimony. Optionally, the catalyst system includes a source of further anions.

By continuous process herein is meant that the reaction process continues beyond that of a simple batch reaction where a batch of reactants and catalyst are allowed to react to completion without further reactant or catalyst input either with or without removal of product during the reaction. In a continuous reaction herein, the reactants are fed continuously so that the reaction can continue, the catalyst is replenished as it degrades and product is removed from the reactor as a product stream as the reaction proceeds.

As mentioned above, in a continuous reaction the catalyst is replenished as the reaction proceeds, more preferably, the catalyst concentration is generally maintained throughout the continuous reaction so that the rate of addition matches the rate of catalyst decay. Further, it is preferred that the unreacted reactant gases are continuously recycled back into the reactor. Still, further it is preferred that the unreacted liquid reactants are continuously recycled back to the reactor.

Preferably, the ethylene and carbon monoxide input feed streams are combined into a single input feed stream prior to contact with the liquid phase. The ethylene:CO molar ratio in the single combined input feed stream is preferably greater than 2:1. However, if the input feed streams are fed into the liquid phase separately then they preferably do so simultaneously to achieve the required input ratio continuously.

Gas Phase Reactant Ratios

The reactor includes provision for a gaseous phase. Typically, a headspace above the liquid phase containing the catalyst and reactants is provided to allow the establishment of a headspace gaseous phase in the reactor.

Preferably, the ethylene:CO gas molar ratio in the gaseous phase of the reactor is between 40:1 and 200:1, more preferably between 55:1 and 150:1, optionally, between 25:1 and 49:1.

Preferably, in a continuous process according to the present invention, the gas phase ethylene and CO are recycled back into the liquid phase of the reactor via the input feed stream, typically, more than 40% by volume of the ethylene and CO are recycled back into the liquid phase of the reactor.

Feed Stream Reactant Ratios

Preferably, the ethylene:CO molar ratio in the gaseous input feed stream(s) of the reactor (including any recycled ethylene and CO) is between 2:1 and 20:1, more preferably, between 2:1 and 10:1, most preferably, between 3:1 and 6:1, especially, 4:1. Typically, the gas feed stream is introduced directly into the liquid phase.

Liquid Phase Reactant Ratios

In a continuous process it is not easy to determine the ethylene:CO ratio in the liquid phase because any analysis in real-time is compromised by the reaction proceeding during the course of the analysis.

Nevertheless, by the use of Henry's constant and the partial pressure in the gas phase, it is possible to calculate the liquid phase concentration of CO. On this basis, preferably, the ethylene:CO molar ratio in the liquid phase is between 10:1 and 1000:1.

Preferably, the gaseous feed stream is directed into the liquid phase for reaction and after passing therethrough, any unreacted gases enter the gas phase which eventually stabilises to be in equilibrium with the liquid phase.

Preferably, the molar ratio of ethylene:CO in the liquid phase is greater than 10:1, more preferably, greater than 20:1 and most preferably greater than 30:1 with, in any case, an optional upper limit of 1000:1. A preferred molar ratio of ethylene:CO in the liquid phase is 30:1 to 600:1, more preferably, a molar ratio of 50:1 to 300:1, most preferably, a molar ratio of 75:1 to 300:1.

Preferably, the ethylene:CO molar ratio entering the liquid phase from the input feed streams is greater than 2:1. Preferably, the ethylene:CO gas molar ratio in the gaseous phase is between 20:1 and 1000:1.

The liquid phase compositions of CO and Ethylene have been determined using an equilibrium flash calculation. This calculation accounts for non-ideality in the liquid phase by the UNIQUAC activity coefficient model, and non-ideality in the vapour phase by the Redlich Kwong equations of state. Parameters in these models have been experimentally measured (including the Henry constants for CO and Ethylene) for the components of interest.

Other Gases

The carbon monoxide or ethylene may be used in the presence of other gases which are generally inert in the in the reaction. Suitable gases include hydrogen, nitrogen, carbon dioxide, ethane and methane or any of the noble gases such as argon.

The level of any such inert gas in the gaseous phase is between 0-75% by volume, more typically, 5-70% by volume, most typically, 15-35% by volume.

Typically, the ethylene, CO and optional inert or other gases are initially introduced into the liquid phase by the gas feed stream.

Gas Mixing

Preferably, the liquid phase is well mixed during the reaction. A preferred type of mixing is achieved using a dual impeller mixer which mixes in two opposed directions in the reactor so that forward flow and back flow are achieved simultaneously.

Preferably, therefore, the present invention includes a mixing apparatus which enables controllable mixing of fluids or solids whilst simultaneously providing an effective mixing environment.

Preferably, the mixing apparatus for mixing the fluids of the present invention in the reactor comprises a shaft rotatable about its longitudinal axis, a first and a second radially extending impeller mounted on the shaft in the liquid phase and respectively axially spaced apart, the first impeller comprising a plurality of curved blades operable to move said fluids in an axial direction towards the second impeller, and the second impeller comprises a plurality of curved blades operable to move said fluids in an axial direction towards the first impeller.

Preferably, the blades on each impeller are inward pumping into the space between the impellers. In the case of a typical substantially vertical shaft, the lower impeller is, therefore, upward pumping and the upper impeller is downward pumping. Preferably, the blades of each impeller are hydrofoil blades. A suitable hydrofoil blade is the Chemineer Maxflo™ W. Alternatively, the Lightnin A315™, A320™ or A340™ may be used.

Obviously, the fluids of the present invention to be mixed in the liquid phase comprise liquid and gas.

Preferably, the first impeller and the second impeller each comprise two or more curved blades, more preferably, three or more curved blades, most preferably, are impellers with four curved blades. The provision of an impeller with a large number of curved blades increases the shear forces acting to break up large bubbles. The small bubbles produced have a smaller average bubble diameter than those produced with a first impeller and/or a second impeller with fewer curved blades and therefore, the available surface area for a reaction to occur is increased.

Preferably, when operating at a low power number complete uniform dispersed phase distribution is achieved. This is highly desirable and is because of the energy efficiency of the blades, typically hydrofoil blades.

Preferably, the specific power used when the first impeller and the second impeller rotate is effective to provide a narrow bubble size distribution.

Preferably, when dual opposed Maxflo impellers are used, the arithmetic mean size ($d_{10}$) is substantially between 250 µm to 550 µm and the surface volume mean diameter ($d_{32}$) is substantially between 400 µm to 750 µm.

Preferably, when BT-6 type impellers are used, the $d_{10}$ is substantially between 250 µm to 1500 µm. In the reactor the gas is sparged into an agitated liquid medium, preferably, the sparged gas rate is substantially between 0.05 to 1.0 $m^3/s$, preferably substantially between 0.1 to 0.5 $m^3/S$, most preferably substantially 0.13 $m^3/s$ at an impeller speed of preferably between 50 rpm to 1200 rpm, most preferably substantially 50 rpm to 200 rpm.

The critical dispersion speed for achieving dispersion in a dual opposed flow hydrofoil system in a vessel having a diameter of preferably substantially between 1 to 10 m, more preferably, substantially between 2 to 5 m, is preferably substantially between 1 to 100 rpm, preferably substantially between 5 to 50 rpm, more preferably substantially between 10 to 20 rpm, most preferably substantially 14 rpm.

Ligands

It will be appreciated by those skilled in the art that the compounds of formulas (I) or (II) may function as ligands that coordinate with the Group 8, 9 or 10 metal or compound thereof to form the compounds for use in the invention. Typically, the Group 8, 9 or 10 metal or compound thereof coordinates to the one or more phosphorus, arsenic and/or antimony atoms of the compound of formulas (I) or (II).

Co-Reactant

The ratio (v/v) of ethylene and co-reactant in the reaction can vary between wide limits and suitably lies in the range of 10:1 to 1:500.

The co-reactant of the present invention may be branched or linear, cyclic, acyclic, part cyclic or aliphatic and comprises an alkanol, particularly a $C_1$-$C_4$ alkanol, which may be optionally substituted with one or more substituents selected from alkyl, halo, especially fluoro. Highly preferred alkanols are methanol, ethanol, propanol, iso-propanol, iso-butanol, t-butyl alcohol, phenol and n-butanol. Especially preferred alkanols are methanol and ethanol. The most preferred alkanol is methanol.

The amount of alcohol is not critical. Generally, amounts are used in excess of the amount of substrate to be carbonylated. Thus the alcohol may serve as the reaction solvent as well, although, if desired, separate solvents may also be used.

It will be appreciated that the end product of the reaction is determined at least in part by the source of alkanol used. For instance, use of methanol produces the corresponding methyl ester. Accordingly, the invention provides a convenient way of adding the group —C(O)O$C_1$-$C_6$ alkyl or aryl across the ethylene double bond.

Solvents

Preferably, the reaction of the present invention is carried out in the presence of a suitable solvent. Suitable solvents will be described hereafter. Preferably, the group 8, 9 or 10 metal/metal compound and ligand are added to the solvent(s) and preferably, dissolved therein.

Suitable solvents for use in the present invention include ketones, such as for example methylbutylketone; ethers, such as for example anisole (methyl phenyl ether), 2,5,8-trioxanonane (diglyme), diethyl ether, dimethyl ether, methyl-tert-butylether (MTBE), tetrahydrofuran, diphenylether, diisopropylether and the dimethylether of di-ethylene-glycol; oxanes, such as for example dioxane; esters, such as for example methylacetate, dimethyladipate methyl benzoate, dimethyl phthalate and butyrolactone; amides, such as for example dimethylacetamide, N-methylpyrrolidone and dimethyl formamide; sulfoxides and sulphones, such as for example dimethylsulphoxide, di-isopropylsulphone, sulfolane (tetrahydrothiophene-2,2-dioxide), 2-methylsulfolane, diethyl sulphone, tetrahydrothiophene 1,1-dioxide and 2-methyl-4-ethylsulfolane; aromatic compounds, including halo variants of such compounds e.g. benzene, toluene, ethyl benzene o-xylene, m-xylene, p-xylene, chlorobenzene, o-dichlorobenzene, m-dichlorobenzene: alkanes, including halo variants of such compounds e.g. hexane, heptane, 2,2,3-trimethylpentane, methylene chloride and carbon tetrachloride; nitriles e.g. benzonitrile and acetonitrile.

Very suitable are aprotic solvents having a dielectric constant that is below a value of 50, more preferably 1-30, most preferably, 1-10, especially in the range of 2 to 8, at 298 or 293K and $1 \times 10^5$ $Nm^{-2}$. In the context herein, the dielectric constant for a given co-solvent is used in its normal meaning of representing the ratio of the capacity of a condenser with that substance as dielectric to the capacity of the same condenser with a vacuum for dielectric. Values for the dielectric constants of common organic liquids can be found in general reference books, such as the Handbook of Chemistry and Physics, 76$^{th}$ edition, edited by David R. Lide et al, and published by CRC press in 1995, and are usually quoted for a temperature of about 20° C. or 25° C., i.e. about 293.15 k or 298.15 K, and atmospheric pressure, i.e. about $1 \times 10^5$ $Nm^{-2}$, and can readily be converted to 298.15 K and atmospheric pressure using the conversion factors quoted. If no literature data for a particular compound is available, the dielectric constant may be readily measured using established physicochemical methods.

Measurement of a dielectric constant of a liquid can easily be performed by various sensors, such as immersion probes, flow-through probes, and cup-type probes, attached to various meters, such as those available from the Brookhaven Instruments Corporation of Holtsville, N.Y. (e.g., model BI-870) and the Scientifica Company of Princeton, N.J. (e.g. models 850 and 870). For consistency of comparison, preferably all measurements for a particular filter system are performed at substantially the same sample temperature, e.g., by use of a water bath. Generally, the measured dielectric constant of a substance will increase at lower temperatures and decrease at higher temperatures. The dielectric constants falling within any ranges herein, may be determined in accordance with ASTM D924.

However, if there is doubt as to which technique to use to determine the dielectric constant a Scientifica Model 870 Dielectric Constant Meter with a 1-200 ∈ range setting should be used.

For example, the dielectric constant of methyl-tert-butyl ether is 4.34 (at 293 K), of dioxane is 2.21 (at 298 K), of toluene is 2.38 (at 298 K), tetrahydrofuran is 7.5 (at 295.2 K) and of acetonitrile is 37.5 (at 298 K). The dielectric values are taken from the handbook of chemistry and physics and the temperature of the measurement is given.

Alternatively, the reaction may proceed in the absence of an aprotic solvent not generated by the reaction itself. In other words, the only aprotic solvent is the reaction product. This aprotic solvent may be solely generated by the reaction itself or, more preferably, is added as a solvent initially and then also produced by the reaction itself. A particularly preferred aprotic solvent is methyl propionate.

Alternatively, a protic solvent other than water may be used. The protic solvent may include a carboxylic acid (as defined above) or an alcohol. Suitable protic solvents include the conventional protic solvents known to the person skilled in the art, such as lower alcohols, such as, for example, methanol, ethanol and isopropanol, and primary and secondary amines, particularly methanol. Mixtures of the aprotic and protic co-solvents may also be employed both initially and when generated by the reaction itself, particularly methyl propionate and methanol.

By protic solvent is meant any solvent that carries a donatable hydrogen ion such as those attached to oxygen as in a hydroxyl group or nitrogen as in an amine group. By aprotic solvent is meant a type of solvent which neither donates nor accepts protons.

Metal

For the avoidance of doubt, references to Group 8, 9 or 10 metals herein should be taken to include Groups 8, 9 and 10 in the modern periodic table nomenclature. By the term "Group 8, 9 or 10" we preferably select metals such as Ru, Rh, Os, Ir, Pt and Pd. Preferably, the metals are selected from Ru, Pt and Pd. More preferably, the metal is Pd.

Carbonylating Agent and Process Conditions

In the process according to the present invention, the carbon monoxide may be used in pure form or diluted with an inert gas such as nitrogen, carbon dioxide, ethane and methane or a noble gas such as argon.

Hydrogen may optionally be added to the carbonylation reaction to improve reaction rate. Suitable levels of hydrogen when utilised may be in the ratio of between 0.1 and 10% vol/vol of the carbon monoxide, more preferably, 1-10% vol/vol of the carbon monoxide, more preferably, 2-5% vol/vol of the carbon monoxide, most preferably 3-5% vol/vol of carbon monoxide.

The molar ratio of the amount of ethylene used in the reaction to the amount of solvent (when present) may vary between wide limits, e.g. from 1:1 to 1:1000 mol/mol. Preferably, the molar ratio of the amount of ethylene used in the reaction to the amount of solvent is between 1:5 and 1:500, more preferably, 1:10 and 1:100. For the avoidance of doubt, such solvent includes the reaction product and co-reactant.

The amount of the catalyst of the invention used in the carbonylation reaction is preferably in the range $1\times10^{-7}$ to $10^{-1}$ moles per mole of ethylene, more preferably, $1\times10^{-6}$ to $10^{-1}$ moles, most preferably $1\times10^{-6}$ to $10^{-2}$ moles per mole of ethylene.

Preferably, the amount of ligand of formulas [I-II] herein to ethylene is in the range $1\times10^{-6}$ to $10^{-1}$, more preferably, $1\times10^{-6}$ to $10^{-1}$, most preferably, $1\times10^{-5}$ to $10^{-2}$ moles per mole of ethylene. Preferably, the amount of catalyst is sufficient to produce product at an acceptable rate commercially.

Preferably, the carbonylation is carried out at temperatures of between −30 to 170° C., more preferably −10° C. to 160° C., most preferably 20° C. to 150° C. An especially preferred temperature is one chosen between 40° C. to 150° C.

Preferably, the carbonylation is carried out at a CO partial pressure in the reactor of between $0.01\times10^5$ N·m$^{-2}$–$2\times10^5$ N·m$^{-2}$, more preferably $0.02\times10^5$ N·m$^{-2}$–$1\times10^5$ N·m$^{-2}$, most preferably $0.05$-$0.5\times10^5$ N·m$^{-2}$. Especially preferred is a CO partial pressure of $0.1$ to $0.3\times10^5$ N·m$^{-2}$.

In the present invention, the ligand to metal molar ratio in the liquid phase is typically between 1:1 and 2:1. Nevertheless, the mole ratio of ligand to group 8, 9 or 10 metal for a bidentate ligand can still be between 1:1 and 100:1, more preferably, 1:1 to 50:1, most preferably, 1:1 to 20:1. However, for commercial reasons, as mentioned above, the bidentate ligand to metal ratio is preferably between 1:1 and 2:1.

Preferably, the mole ratio of ligand to acid in the reactor for a bidentate ligand and a monoprotic acid is between 1:1 and 1:2000, more preferably 1:2 to 1:500, most preferably, 1:5 to 1:100.

Preferably, the mole ratio of group 8, 9 or 10 metal to acid for a monoprotic acid is from 1:1 to 1:4000, more preferably, 1:2 to 1:1000, most preferably, 1:5 to 1:200, especially, 1:10 to 1:200.

For the avoidance of doubt, the above ratio conditions are given for the continuous reaction.

As mentioned, the catalyst system of the present invention may be used homogeneously or heterogeneously. Preferably, the catalyst system is used homogeneously.

Suitably, the catalysts of the invention are prepared in a separate step preceding their use in-situ in the carbonylation reaction.

Conveniently, the process of the invention may be carried out by dissolving the Group 8, 9 or 10 metal or compound thereof as defined herein in a suitable solvent such as one of the alkanols or aprotic solvents previously described or a mixture thereof. A particularly preferred solvent would be the product of the specific carbonylation reaction which may be mixed with other solvents or co-reactants. Subsequently, the admixed metal and solvent may be mixed with a compound of formulas I-II as defined herein. Alternatively, the metal and compound of formulas I-II may be added to the solvent simultaneously or the compound may be dissolved and then the metal may be dissolved subsequently.

The carbon monoxide may be used in the presence of other gases which are inert in the reaction. Examples of such gases include hydrogen, nitrogen, carbon dioxide, ethane and methane and the noble gases such as argon.

The product of the reaction may be separated from the other components by any suitable means. However, it is an advantage of the present process that significantly fewer by-products are formed thereby reducing the need for further purification after the initial separation of the product as may be evidenced by the generally significantly higher selectivity.

A further advantage is that the other components which contain the catalyst system which may be recycled and/or reused in further reactions with minimal supplementation of fresh catalyst.

In particular, the gaseous phase may be recycled into the gas feed stream which may then be adjusted with fresh supplies of carbon monoxide and ethylene as required to provide the desired input gas feed stream.

The continuous reaction can continue as long as the TON is commercially acceptable.

Support and Dispersant

According to a further aspect, the present invention provides a process for the carbonylation of ethylene as defined herein wherein the process is carried out with the catalyst comprising a support, preferably an insoluble support.

Preferably, the support comprises a polymer such as a polyolefin, polystyrene or polystyrene copolymer such as a divinylbenzene copolymer or other suitable polymers or copolymers known to those skilled in the art; a silicon derivative such as a functionalised silica, a silicone or a silicone rubber; or other porous particulate material such as for example inorganic oxides and inorganic chlorides.

Preferably the support material is porous silica which has a surface area in the range of from 10 to 700 m$^2$/g, a total pore volume in the range of from 0.1 to 4.0 cc/g and an average particle size in the range of from 10 to 500 µm. More preferably, the surface area is in the range of from 50 to 500 m$^2$/g, the pore volume is in the range of from 0.5 to 2.5 cc/g and the average particle size is in the range of from 20 to 200 µm. Most desirably the surface area is in the range of from 100 to 400 m$^2$/g, the pore volume is in the range of from 0.8 to 3.0 cc/g and the average particle size is in the range of from 30 to 100 µm. The average pore size of typical porous support materials is in the range of from 10 to 1000 Å. Preferably, a support material is used that has an average pore diameter of from 50 to 500 Å, and most desirably from 75 to 350 Å. It may be particularly desirable to dehydrate the silica at a temperature of from 100° C. to 800° C. anywhere from 3 to 24 hours.

Suitably, the support may be flexible or a rigid support, the insoluble support is coated and/or impregnated with the compounds of the process of the invention by techniques well known to those skilled in the art.

Alternatively, the compounds of the process of the invention are fixed to the surface of an insoluble support, optionally via a covalent bond, and the arrangement optionally includes a bifunctional spacer molecule to space the compound from the insoluble support.

The compounds of the invention may be fixed to the surface of the insoluble support by promoting reaction of a functional group present in the compound of formula I or II with a complimentary reactive group present on or previously inserted into the support. The combination of the reactive group of the support with a complimentary substituent of the compound of the invention provides a heterogeneous catalyst where the compound of the invention and the support are linked via a linkage such as an ether, ester, amide, amine, urea, keto group.

The choice of reaction conditions to link a compound of the process of the present invention to the support depends upon the groups of the support. For example, reagents such as carbodiimides, 1,1'-carbonyldiimidazole, and processes such as the use of mixed anhydrides, reductive amination may be employed.

According to a further aspect, the present invention provides the use of the process or catalyst of any aspect of the invention wherein the catalyst is attached to a support.

Additionally, the bidentate ligand may be bonded to a suitable polymeric substrate via at least one of the bridge substituents (including the cyclic atoms), the bridging group X, the linking group A or the linking group B e.g. cis-1,2-bis (di-t-butylphosphinomethyl)benzene may be bonded, preferably, via the 3, 4, 5 or 6 cyclic carbons of the benzene group to polystyrene to give an immobile heterogeneous catalyst.

The use of stabilising compounds with the catalyst system may also be beneficial in improving recovery of metal which has been lost from the catalyst system. When the catalyst system is utilized in a liquid reaction medium such stabilizing compounds may assist recovery of the group 8, 9 or 10 metal.

Preferably, therefore, the catalyst system includes in a liquid reaction medium a polymeric dispersant dissolved in a liquid carrier, said polymeric dispersant being capable of stabilising a colloidal suspension of particles of the group 8, 9 or 10 metal or metal compound of the catalyst system within the liquid carrier.

The liquid reaction medium may be a solvent for the reaction or may comprise one or more of the reactants or reaction products themselves. The reactants and reaction products in liquid form may be miscible with or dissolved in a solvent or liquid diluent.

The polymeric dispersant is soluble in the liquid reaction medium, but should not significantly increase the viscosity of the reaction medium in a way which would be detrimental to reaction kinetics or heat transfer. The solubility of the dispersant in the liquid medium under the reaction conditions of temperature and pressure should not be so great as to deter significantly the adsorption of the dispersant molecules onto the metal particles.

The polymeric dispersant is capable of stabilising a colloidal suspension of particles of said group 8, 9 or 10 metal or metal compound within the liquid reaction medium such that the metal particles formed as a result of catalyst degradation are held in suspension in the liquid reaction medium and are discharged from the reactor along with the liquid for reclamation and optionally for re-use in making further quantities of catalyst. The metal particles are normally of colloidal dimensions, e.g. in the range 5-100 nm average particle size although larger particles may form in some cases. Portions of the polymeric dispersant are adsorbed onto the surface of the metal particles whilst the remainder of the dispersant molecules remain at least partially solvated by the liquid reaction medium and in this way the dispersed group 8, 9 or 10 metal particles are stabilised against settling on the walls of the reactor or in reactor dead spaces and against forming agglomerates of metal particles which may grow by collision of particles and eventually coagulate. Some agglomeration of particles may occur even in the presence of a suitable dispersant but when the dispersant type and concentration is optimised then such agglomeration should be at a relatively low level and the agglomerates may form only loosely so that they may be broken up and the particles re-dispersed by agitation.

The polymeric dispersant may include homopolymers or copolymers including polymers such as graft copolymers and star polymers.

Preferably, the polymeric dispersant has sufficiently acidic or basic functionality to substantially stabilise the colloidal suspension of said group 8, 9 or 10 metal or metal compound.

By substantially stabilise is meant that the precipitation of the group 8, 9 or 10 metal from the solution phase is substantially avoided.

Particularly preferred dispersants for this purpose include acidic or basic polymers including carboxylic acids, sulphonic acids, amines and amides such as heterocycle, substituted polyvinyl polymers such as polyvinyl pyrrolidone or copolymers of the aforesaid.

Examples of such polymeric dispersants may be selected from polyvinylpyrrolidone, polyacrylamide, polyacrylonitrile, polyethylenimine, polyglycine, polyacrylic acid, polymethacrylic acid, poly(3-hydroxybutyricacid), poly-L-leucine, poly-L-methionine, poly-L-proline, poly-L-serine, poly-L-tyrosine, poly(vinylbenzenesulphonic acid) and poly(vinylsulphonic acid), acylated polyethylenimine. Suitable acylated polyethylenimines are described in BASF patent publication EP1330309 A1 and U.S. Pat. No. 6,723,882.

Preferably, the polymeric dispersant incorporates acidic or basic moieties either pendant or within the polymer backbone. Preferably, the acidic moieties have a dissociation constant ($pK_a$) of less than 6.0, more preferably, less than 5.0, most preferably less than 4.5. Preferably, the basic moieties have a base dissociation constant ($pK_b$) being of less than 6.0, more preferably less than 5.0 and most preferably less than 4.5, $pK_a$ and $pK_b$ being measured in dilute aqueous solution at 25° C.

Suitable polymeric dispersants, in addition to being soluble in the reaction medium at reaction conditions, contain at least one acidic or basic moiety, either within the polymer backbone or as a pendant group. We have found that polymers incorporating acid and amide moieties such as polyvinylpyrrolidone (PVP) and polyacrylates such as polyacrylic acid (PAA) are particularly suitable. The molecular weight of the polymer which is suitable for use in the invention depends upon the nature of the reaction medium and the solubility of the polymer therein. We have found that normally the average molecular weight is less than 100,000. Preferably, the average molecular weight is in the range 1,000-200,000, more preferably, 5,000-100,000, most preferably, 10,000-40,000 e.g. Mw is preferably in the range 10,000-80,000, more preferably 20,000-60,000 when PVP is used and of the order of 1,000-10,000 in the case of PAA.

The effective concentration of the dispersant within the reaction medium should be determined for each reaction/catalyst system which is to be used.

The dispersed group 8, 9 or 10 metal may be recovered from the liquid stream removed from the reactor e.g. by filtration and then either disposed of or processed for re-use as a catalyst or other applications. In a continuous process the liquid stream may be circulated through an external heat-exchanger and in such cases it may be convenient to locate filters for the palladium particles in these circulation apparatus.

Preferably, the polymer:metal mass ratio in g/g is between 1:1 and 1000:1, more preferably, between 1:1 and 400:1, most preferably, between 1:1 and 200:1. Preferably, the polymer:metal mass ratio in g/g is up to 1000, more preferably, up to 400, most preferably, up to 200.

Conveniently, the process of the invention may utilise highly stable compounds under typical carbonylation reaction conditions such that they require little or no replenishment. Conveniently, the process of the invention may have a high rate for the carbonylation reaction. Conveniently, the process of the invention may promote high conversion rates, thereby yielding the desired product in high yield with little or no impurities. Consequently, the commercial viability of the carbonylation reaction may be increased by employing the process of the invention. It is especially advantageous that the process of the invention provides a carbonylation reaction with a high TON number.

It will be appreciated that any of the features set forth in the first aspect of the invention may be regarded as preferred features of the second, third or other aspect of the present invention and vice versa.

Ligand of General Formula I

As mentioned above, the bidentate phosphine, arsine or stibine ligand has a formula I

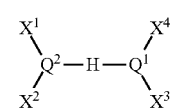

wherein H is a bivalent organic bridging group with 1-6 atoms in the bridge;

the groups $X^1$, $X^2$, $X^3$ and $X^4$ independently represent univalent radicals of up to 30 atoms, optionally having at least one tertiary carbon atom via which the group is joined to the $Q^1$ or $Q^2$ atom, or $X^1$ and $X^2$ and/or $X^3$ and $X^4$ together form a bivalent radical of up to 40 atoms, optionally having at least two tertiary carbon atoms via which the radical is joined to the $Q^1$ and/or $Q^2$ atom; and $Q^1$ and $Q^2$ each independently represent phosphorus, arsenic or antimony.

Preferably, the group H has 3-5 atoms in the bridge.

In any case, the bivalent organic bridging group H may be an unsubstituted or substituted, branched or linear, cyclic, acyclic or part cyclic aliphatic, aromatic or araliphatic bivalent group having 1-50 atoms in the bridging group and 1-6, more preferably, 2-5, most preferably 3 or 4 atoms in the bridge.

The bivalent organic bridging group may be substituted or interrupted by one or more heteroatoms such as O, N, S, P or Si. Such heteroatoms may be found in the bridge but it is preferred that the bridge consists of carbon atoms.

Suitable aliphatic bridging groups include alkylene groups such as 1,2-ethylene, 1-3 propylene, 1,2-propylene, 1,4-butylene, 2,2-dimethyl-1,3-propylene, 2-methyl-1,3-propylene, 1,5-pentylene, —O—CH$_2$CH$_2$—O— and —CH$_2$—NR—CH$_2$— or partial cycloaliphatic bridges including 1-methylene-cyclohex-2-yl, 1,2-dimethylene-cyclohexane and 1,2-dimethylene-cyclopentane. Suitable aromatic or araliphatic bridges include 1,2-dimethylenebenzene, 1,2-dimethyleneferrocene, 1-methylene-phen-2-yl, 1-methylene-naphth-8-yl, 2-methylene-biphen-2'-yl and 2-methylene-binaphth-2'-yl. Bidentate phosphine aromatic bridged radicals of the latter three are illustrated below.

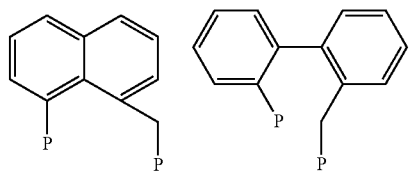

1, 8, Napthyl     2, 2', Biphenyl

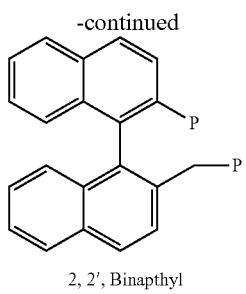

2, 2', Binapthyl

In one set of embodiments, H in formula I is the group -A-R—B— so so that the formula is a bidentate ligand of general formula II

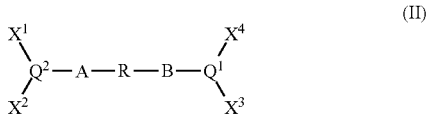

wherein:
A and/or B each independently represent optional lower alkylene linking groups;
R represents a cyclic hydrocarbyl structure to which $Q^1$ and $Q^2$ are linked, via the said linking group if present, on available adjacent cyclic atoms of the cyclic hydrocarbyl structure; and
$Q^1$ and $Q^2$ each independently represent phosphorus, arsenic or antimony.

Preferably, the groups $X^3$ and $X^4$ independently represent univalent radicals of up to 30 atoms having at least one tertiary carbon atom or $X^3$ and $X^4$ together form a bivalent radical of up to 40 atoms having at least two tertiary carbon atoms wherein each said univalent or bivalent radical is joined via said at least one or two tertiary carbon atoms respectively to the respective atom $Q^1$.

Preferably, the groups $X^1$ and $X^2$ independently represent univalent radicals of up to 30 atoms having at least one primary, secondary, aromatic ring or tertiary carbon atom or $X^1$ and $X^2$ together form a bivalent radical of up to 40 atoms having at least two primary, secondary, aromatic ring or tertiary carbon atoms wherein each said univalent or bivalent radical is joined via said at least one or two primary, secondary, aromatic ring or tertiary carbon atom(s) respectively to the respective atom $Q^2$.

Preferably, the groups $X^1$, $X^2$, $X^3$ and $X^4$ independently represent univalent radicals of up to 30 atoms having at least one tertiary carbon atom or $X^1$ and $X^2$ and/or $X^3$ and $X^4$ together form a bivalent radical of up to 40 atoms having at least two tertiary carbon atoms wherein each said univalent or bivalent radical is joined via said at least one or two tertiary carbon atoms respectively to the appropriate atom $Q^1$ or $Q^2$.

Preferably, when $X^1$ and $X^2$ or $X^1$ and $X^2$ together are not joined via at least one or two tertiary carbon atom(s) respectively to the respective atom $Q^2$, it is particularly preferred that at least one of the groups $X^1$ or $X^2$ which is thereby joined to the $Q^2$ atom via a primary, secondary or aromatic ring carbon includes a substituent. Preferably, the substituent is either on the carbon directly joined to the $Q^2$ atom or on the carbon adjacent thereto. However, the substituent can be more remote from the $Q^2$ atom. For instance, it may be up to 5 carbons removed from the $Q^2$ atom. Accordingly, it is preferred that the carbon joined to the $Q^2$ atom is an aliphatic secondary carbon atom or the alpha carbon thereto is an aliphatic secondary or tertiary carbon atom or the carbon joined to the $Q^2$ atom is an aromatic carbon which forms part of an aromatic ring substituted at a suitable position in the ring. Preferably, in this case, the substituent is on the atom adjacent the atom in the ring joined to the $Q^2$ atom.

Preferably, the further substituent in the preceding paragraph is a $C_1$-$C_7$ alkyl group or O—$C_1$-$C_7$ alkyl group, such as a methyl, ethyl, n-propyl, iso-butyl t-butyl, methoxy or ethoxy group or a relatively inert group such as —CN, —F, —Si(alkyl)$_3$, —OCOR$^{63}$, —C(O)—, or —CF$_3$ wherein R$^{63}$ is alkyl, aryl or Het. Particularly preferred substituents are methyl, ethyl and propyl groups, especially methyl, methoxy or ethyl, more especially, methyl. A preferred range of groups are the $C_1$-$C_7$ alkyl, O— $C_1$-$C_7$ alkyl substituted phenyl groups, especially, methyl, methoxy or ethyl phenyl groups. In such phenyl embodiments, substitution may be at the ortho, meta or para position, preferably, the ortho or meta position, most preferably, the ortho position of the ring.

Suitable non tertiary carbon joined $X^1$ or $X^2$ groups are prop-2-yl, phen-1-yl, 2-methyl-phen-1-yl, 2-methoxy-phen-1-yl, 2-fluoro-phen-1-yl, 2-trifluoromethyl-phen-1-yl, 2-trimethylsilyl-phen-1-yl, 4-methyl-phen-1-yl, 3-methyl-phen-1-yl, but-2-yl, pent-2-yl, pent-3-yl, 2-ethyl-phen-1-yl, 2-propyl-phen-1-yl and 2-prop-2'-yl-phen-1-yl.

The cyclic hydrocarbyl structure which R in formula II represents may be aromatic, non-aromatic, mixed aromatic and non-aromatic, mono-, bi-, tri- or polycyclic, bridged or unbridged, substituted or unsubstituted or interrupted by one or more hetero atoms, with the proviso that the majority of the cyclic atoms (i.e. more than half) in the structure are carbon. The available adjacent cyclic atoms to which the $Q^1$ and $Q^2$ atoms are linked form part of a or the ring of the cyclic hydrocarbyl structure. This ring to which the $Q^1$ and $Q^2$ atoms are immediately linked via the linking group, if present, may itself be an aromatic or non-aromatic ring. When the ring to which the $Q^1$ and $Q^2$ atoms are directly attached via the linking group, if present, is non-aromatic, any further rings in a bicyclic, tricyclic or polycyclic structure can be aromatic or non-aromatic or a combination thereof. Similarly, when the ring to which the $Q^1$ and $Q^2$ atoms are immediately attached via the linking group if present is aromatic, any further rings in the hydrocarbyl structure may be non-aromatic or aromatic or a combination thereof.

For simplicity, these two types of bridging group R will be referred to as an aromatic bridged cyclic hydrocarbyl structure or a non-aromatic bridged cyclic hydrocarbyl structure irrespective of the nature of any further rings joined to the at least one ring to which the $Q^1$ and $Q^2$ atoms are linked via the linking groups directly.

The non-aromatic bridged cyclic hydrocarbyl structure which is substituted by A and B at adjacent positions on the at least one non-aromatic ring preferably, has a cis-conformation with respect to the A and B substituents i.e. A and B extend away from the structure on the same side thereof.

Preferably, the non-aromatic bridged cyclic hydrocarbyl structure has from 3 up to 30 cyclic atoms, more preferably from 4 up to 18 cyclic atoms, most preferably from 4 up to 12 cyclic atoms and especially 5 to 8 cyclic atoms and may be monocyclic or polycyclic. The cyclic atoms may be carbon or hetero, wherein references to hetero herein are references to sulphur, oxygen and/or nitrogen. Typically, the non-aromatic bridged cyclic hydrocarbyl structure has from 2 up to 30 cyclic carbon atoms, more preferably from 3 up to 18 cyclic carbon atoms, most preferably from 3 up to 12 cyclic carbon atoms and especially 3 to 8 cyclic carbon atoms, may be monocyclic or polycyclic and may or may not be interrupted by one or more hetero atoms. Typically, when the non-aromatic bridged cyclic hydrocarbyl structure is polycyclic it is preferably bicyclic or tricyclic. The non-aromatic bridged cyclic hydrocarbyl structure as defined herein may include unsaturated bonds. By cyclic atom is meant an atom which forms part of a cyclic skeleton.

The non-aromatic bridged cyclic hydrocarbyl structure, apart from that it may be interrupted with hetero atoms may be unsubstituted or substituted with one or more further substituents selected from aryl, alkyl, hetero (preferably oxygen), Het, halo, cyano, nitro, —$OR^{19}$, —$OC(O) R^{20}$, —$C(O) R^{21}$, —$C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$ or —$CF_3$ wherein $R^{19}$-$R^{30}$ are as defined herein.

The non-aromatic bridged cyclic hydrocarbyl structure may be selected from cyclohexyl, cyclopentyl, cyclobutyl, cyclopropyl, cycloheptyl, cyclooctyl, cyclononyl, tricyclodecyl, piperidinyl, morpholinyl, norbornyl, isonorbornyl, norbornenyl, isonorbornenyl, bicyclo[2,2,2]octyl, tetrahydrofuryl, dioxanyl, O-2,3-isopropylidene-2,3-dihydroxy-ethyl, cyclopentanonyl, cyclohexanonyl, cyclopentenyl, cyclohexenyl, cyclohexadienyl, cyclobutenyl, cyclopentenonyl, cyclohexenonyl, adamantyl, furans, pyrans, 1,3 dioxane, 1,4 dioxane, oxocene, 7-oxabicyclo[2.2.1]heptane, pentamethylene sulphide, 1,3 dithiane, 1,4 dithiane, furanone, lactone, butyrolactone, pyrone, succinic anhydride, cis and trans 1,2-cyclohexanedicarboxylic anhydride, glutaric anhydride, pyrollidine, piperazine, imidazole, 1,4,7 triazacyclononane, 1,5,9 triazacyclodecane, thiomorpholine, thiazolidine, 4,5-diphenyl-cyclohexyl, 4 or 5-phenyl-cyclohexyl, 4,5-dimethyl-cyclohexyl, 4 or 5-methylcyclohexyl, 1,2-decalinyl, 2,3,3a,4,5, 6,7,7a-octahydro-1H-inden-5,6-yl, 3a,4,5,6,7,7a-hexahydro-1H-inden-5,6-yl, 1, 2 or 3 methyl-3a, 4,5,6,7,7a hexahydro-1H-inden-5,6-yl, trimethylene norbornanyl, 3a, 4,7,7a-tetrahydro-1H-inden-5,6-yl, 1, 2 or 3-dimethyl-3a, 4,5,6,7, 7a-hexahydro-1H-inden 5,6-yls, 1,3-bis(trimethylsilyl)-3a,4, 5,6,7,7a-hexahydro-3H-isobenzofuran and wherein the linking group A or B is joined to available non-substituted adjacent cyclic atoms.

R may represent a non-aromatic bridged cyclic hydrocarbyl structure having at least one non-aromatic ring to which the $Q^1$ and $Q^2$ atoms are linked, via the said linking group, if present, on available adjacent cyclic atoms of the at least one ring. Apart from that it may be in the form of a polycyclic structure, the non-aromatic bridged cyclic hydrocarbyl structure may be unsubstituted or substituted with at least one substituent, preferably on at least one further non-adjacent cyclic atom of the at least one ring.

By the term one further non-adjacent cyclic atom is meant any further cyclic atom in the ring which is not adjacent to any one of said available adjacent cyclic atoms to which the $Q^1$ and $Q^2$ atoms are linked.

However, the cyclic atoms adjacent to the said available adjacent cyclic atoms and cyclic atoms elsewhere in the hydrocarbyl structure may also be substituted and suitable substituents for the cyclic atom(s) are defined herein.

For the avoidance of doubt, references to the cyclic atoms adjacent to the said available adjacent cyclic atoms or the like is not intended to refer to one of the said two available adjacent cyclic atoms themselves. As an example, a cyclohexyl ring joined to a $Q^1$ atom via position 1 on the ring and joined to a $Q^2$ atom via position 2 on the ring has two said further non adjacent cyclic atoms as defined at ring position 4 and 5 and two adjacent cyclic atoms to the said available adjacent cyclic atoms at positions 3 and 6.

The term a non-aromatic bridged cyclic hydrocarbyl structure means that the at least one ring to which the $Q^1$ and $Q^2$ atom are linked via B & A respectively is non-aromatic, and aromatic should be interpreted broadly to include not only a phenyl type structure but other rings with aromaticity such as that found in the cyclopentadienyl anion ring of ferrocenyl, but, in any case, does not exclude aromatic substituents on this non-aromatic at least one ring.

The substituents on the said cyclic atoms of the non-aromatic bridged hydrocarbyl structure may be selected to encourage greater stability but not rigidity of conformation in the cyclic hydrocarbyl structure. The substituents may, therefore, be selected to be of the appropriate size to discourage or lower the rate of non-aromatic ring conformation changes. Such groups may be independently selected from lower alkyl, aryl, het, hetero, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$ or —$CF_3$, more preferably, lower alkyl, or hetero most preferably, $C_1$-$C_6$ alkyl. Where there are two or more further cyclic atoms in the hydrocarbyl structure they may each be independently substituted as detailed herein. Accordingly, where two such cyclic atoms are substituted, the substituents may combine to form a further ring structure such as a 3-20 atom ring structure. Such a further ring structure may be saturated or unsaturated, unsubstituted or substituted by one or more substituents selected from halo, cyano, nitro, $OR^{19}$, $OC(O)R^{20}$, $C(O) R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, aryl, alkyl, Het, wherein $R^{19}$ to $R^{30}$ are as defined herein and/or be interrupted by one or more (preferably less than a total of 4) oxygen, nitrogen, sulphur, silicon atoms or by silano or dialkyl silicon groups or mixtures thereof.

Particularly preferred substituents are methyl, ethyl, propyl, isopropyl, phenyl, oxo, hydroxy, mercapto, amino, cyano and carboxy. Particularly preferred substituents when two or more further non adjacent cyclic atoms are substituted are x,y-dimethyl, x,y-diethyl, x,y-dipropyl, x,y-di-isopropyl, x,y-diphenyl, x,y-methyl/ethyl, x,y-methyl/phenyl, saturated or unsaturated cyclopentyl, saturated or unsaturated cyclohexyl, 1,3 substituted or unsubstituted 1,3H-furyl, un-substituted cyclohexyl, x,y-oxo/ethyl, x,y-oxo/methyl, disubstitution at a single ring atom is also envisaged, typically, x,x-lower dialkyl. More typical substituents are methyl, ethyl, n-propyl, iso-propyl, n-butyl, isobutyl, t-butyl, or oxo, most typically methyl or ethyl, or oxo most typically, methyl; wherein x and y stand for available atom positions in the at least one ring.

Preferably, further substitution of said non-aromatic cyclic hydrocarbyl structure is not on said available adjacent carbon atoms to which said $Q^1$ and $Q^2$ atoms are linked. The non-aromatic cyclic hydrocarbyl structure may be substituted at one or more said further cyclic atoms of the hydrocarbyl structure but is preferably substituted at 1, 2, 3 or 4 such cyclic atoms, more preferably 1, 2 or 3, most preferably at 1 or 2 such cyclic atoms, preferably on the at least one non-aromatic ring. The substituted cyclic atoms may be carbon or hetero but are preferably carbon.

When there are two or more substituents on the said cyclic hydrocarbyl structure they may meet to form a further ring structure unless excluded herein.

The non-aromatic bridged cyclic hydrocarbyl structure may be selected from 4 and/or 5 lower alkylcyclohexane-1, 2-diyl, 4 lower alkylcyclopentane-1,2-diyl, 4,5 and/or 6 lower alkylcycloheptane-1,2-diyl, 4, 5, 6 and/or 7 lower alkylcyclooctane-1,2-diyl, 4, 5, 6, 7 and/or 8 lower alkylcyclononane-1,2-diyl, 5 and/or 6 lower alkyl piperidinane-2,3-diyl, 5 and/or 6 lower alkyl morpholinane-2,3-diyl, O-2,3-isopropylidene-2,3-dihydroxy-ethane-2,3-diyl, cyclopentanone-3,4-diyl, cyclohexanone-3,4-diyl, 6-lower alkyl cyclohexanone-3,4-diyl, 1-lower alkyl cyclopentene-3,4-diyl, 1 and/or 6 lower alkyl cyclohexene-3,4-diyl, 2 and/or 3 lower alkyl cyclohexadiene-5,6-diyl, 5 lower alkyl cyclohexen-4-one-1,2-diyl, adamantyl-1-2-diyl, 5 and/or 6 lower alkyl tetrahydropyran-2,3 diyl, 6-lower alkyl dihydropyran-2,3 diyl, 2-lower alkyl 1,3 dioxane-5,6-diyl, 5 and/or 6 lower alkyl-1,4 dioxane-2,3-diyl, 2-lower alkyl pentamethylene sulphide 4,5-diyl, 2-lower alkyl-1,3 dithiane-5,6-diyl, 2 and/or 3-lower alkyl 1,4 dithiane-5,6-diyl, tetrahydro-furan-2-one-4,5-diyl, delta-valero lactone 4,5-diyl, gamma-butyrolactone 3,4-diyl, 2H-dihydropyrone 5,6-diyl, glutaric anhydride 3,4-diyl, 1-lower alkyl pyrollidine-3,4-diyl, 2,3 di-lower alkyl piperazine-5,6-diyl, 2-lower alkyl dihydro imidazole-4,5-diyl, 2,3,5 and/or 6 lower alkyl-1,4,7 triazacyclononane-8,9-diyl, 2,3,4 and/or 10 lower alkyl-1,5,9 triazacyclodecane 6,7-diyl, 2,3-di-lower alkyl thiomorpholine-5,6-diyl, 2-lower alkyl-thiazolidine-4,5-diyl, 4,5-diphenyl-cyclohexane-1,2-diyl, 4 and/or 5-phenyl-cyclohexane-1,2-diyl, 4,5-dimethyl-cyclohexane-1,2-diyl, 4 or 5-methylcyclohexane-1,2-diyl, 2, 3, 4 and/or 5 lower alkyl-decahydronaphthalene 8,9-diyl, bicyclo[4.3.0]nonane-3,4 diyl, 3a,4,5,6,7,7a-hexahydro-1H-inden-5,6-diyl, 1, 2 and/or 3 methyl-3a, 4,5,6,7,7a hexahydro-1H-inden-5,6-diyl, Octahydro-4,7 methano indene-1,2-diyl, 3a, 4,7,7a-tetrahydro-1H-inden-5,6-diyl, 1,2 and/or 3-dimethyl-3a, 4,5,6,7,7a-hexahydro-1H-inden 5,6-diyls, 1,3-bis(trimethylsilyl)-3a,4,5,6,7,7a-hexahydro-3H-isobenzofuran-5,6-diyl.

Alternatively, the substituents on the said at least one further non adjacent cyclic atom of the non-aromatic bridged hydrocarbyl structure may be a group Y where Y represents a group which is at least as sterically hindering as phenyl and when there are two or more substituents Y they are each as sterically hindering as phenyl and/or combine to form a group which is more sterically hindering than phenyl.

Preferably, Y represents —$SR^{40}R^{41}R^{42}$ wherein S represents Si, C, N, S, O or aryl and $R^{40}R^{41}R^{42}$ are as defined herein. Preferably each Y and/or combination of two or more Y groups is at least as sterically hindering as t-butyl.

More preferably, when there is only one substituent Y, it is at least as sterically hindering as t-butyl whereas where there are two or more substituents Y, they are each at least as sterically hindering as phenyl and at least as sterically hindering as t-butyl if combined into a single group.

Preferably, when S is aryl, $R^{40}$, $R^{41}$ and $R^{42}$ are independently hydrogen, alkyl, —$BQ^3$-$X^3(X^4)$ (wherein B, $X^3$ and $X^4$ are as defined herein and $Q^3$ is defined as $Q^1$ or $Q^2$ above), phosphorus, aryl, arylene, alkaryl, arylenalkyl, alkenyl, alkynyl, het, hetero, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$, —$CF_3$, —$SiR^{71}R^{72}R^{73}$ or alkylphosphorus.

Preferably, when S is Si, C, N, S or O, $R^{40}$, $R^{41}$ and $R^{42}$ are independently hydrogen, alkyl, phosphorus, aryl, arylene, alkaryl, aralkyl, arylenalkyl, alkenyl, alkynyl, het, hetero, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$, —$CF_3$, —$SiR^{71}R^{72}R^{73}$, or alkylphosphorus wherein at least one of $R^{40}$-$R^{42}$ is not hydrogen and wherein $R^{19}$-$R^{30}$ are as defined herein; and $R^{71}$-$R^{73}$ are defined as $R^{40}$-$R^{42}$ but are preferably $C_1$-$C_4$ alkyl or phenyl.

Preferably, S is Si, C or aryl. However, N, S or O may also be preferred as one or more of the Y groups in combined groups. For the avoidance of doubt, as oxygen or sulphur can be bivalent, $R^{40}$-$R^{42}$ can also be lone pairs.

Preferably, in addition to group Y, the non-aromatic bridged structure may be unsubstituted or further substituted with groups selected from Y, alkyl, aryl, arylene, alkaryl, aralkyl, arylenalkyl, alkenyl, alkynyl, het, hetero, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$, —$CF_3$, —$SiR^{71}R^{72}R^{73}$, or alkylphosphorus wherein $R^{19}$-$R^{30}$ are as defined herein; and $R^{71}$-$R^{73}$ are defined as $R^{40}$-$R^{42}$ but are preferably $C_1$-$C_4$ alkyl or phenyl.

In addition, when S is aryl, the aryl may be substituted with in addition to $R^{40}$, $R^{41}$, $R^{42}$ any of the further substituents defined for the non-aromatic bridged structure above.

More preferred Y substituents may be selected from t-alkyl or t-alkyl, aryl such as -t-butyl, —$SiMe_3$, or 2-phenylprop-2-yl, -phenyl, alkylphenyl-, phenylalkyl- or phosphinoalkyl-such as phosphinomethyl.

Preferably, when S is Si or C and one or more of $R^{40}$-$R^{42}$ are hydrogen, at least one of $R^{40}$-$R^{42}$ should be sufficiently bulky to give the required steric hindrance and such groups are preferably phosphorus, phosphinoalkyl-, a tertiary carbon bearing group such as -t-butyl, -aryl, -alkaryl, -aralkyl or tertiary silyl.

In some embodiments, there may be two or more said Y substituents on further cyclic atoms of the non-aromatic bridged structure. Optionally, the said two or more substituents may combine to form a further ring structure such as a cycloaliphatic ring structure.

Some typical hydrocarbyl structures are shown below wherein R', R'', R''', R'''' etc are defined in the same way as the substituents on the cyclic atoms above but may also be hydrogen, or represent the hetero atom being non substituted if linked directly to a hetero atom and may be the same or different. The diyl methylene linkages to the phosphorus (not shown) are shown in each case.

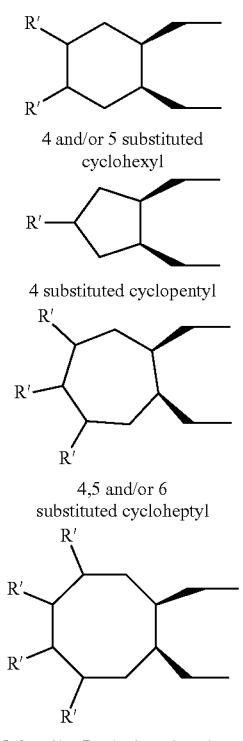

4 and/or 5 substituted cyclohexyl 4 substituted cyclopentyl 4,5 and/or 6 substituted cycloheptyl 4,5,6 and/or 7 substituted cyclooctyl -continued

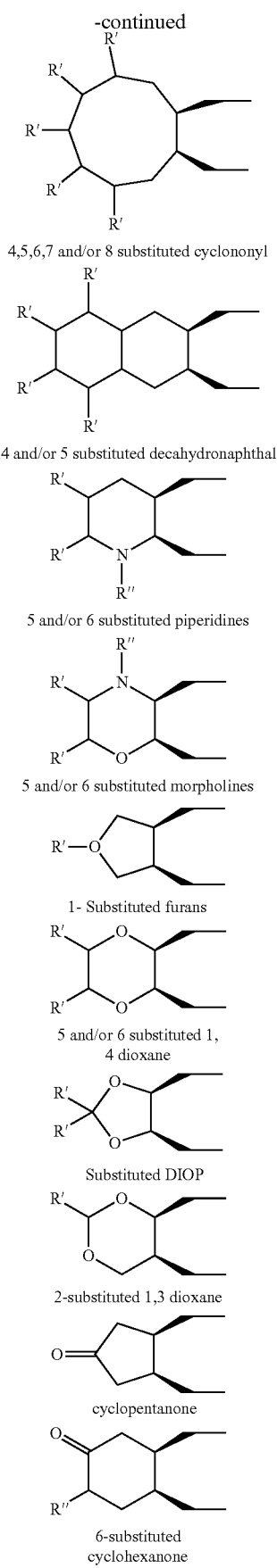

4,5,6,7 and/or 8 substituted cyclononyl 2,3,4 and/or 5 substituted decahydronaphthalene 5 and/or 6 substituted piperidines 5 and/or 6 substituted morpholines 1- Substituted furans 5 and/or 6 substituted 1,4 dioxane Substituted DIOP 2-substituted 1,3 dioxane cyclopentanone 6-substituted cyclohexanone -continued

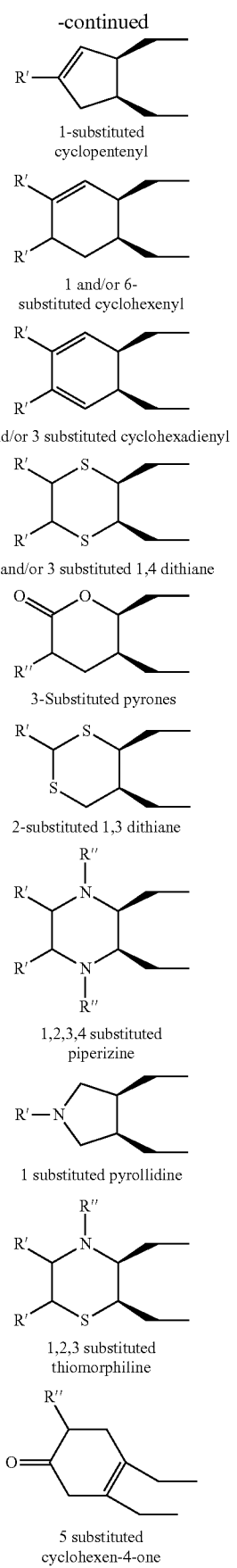

1-substituted cyclopentenyl 1 and/or 6-substituted cyclohexenyl 2 and/or 3 substituted cyclohexadienyl 2 and/or 3 substituted 1,4 dithiane 3-Substituted pyrones 2-substituted 1,3 dithiane 1,2,3,4 substituted piperizine 1 substituted pyrollidine 1,2,3 substituted thiomorphiline 5 substituted cyclohexen-4-one

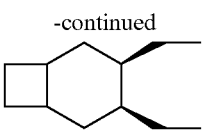
Bicyclo [4.2.0] octane

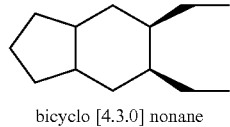
bicyclo [4.3.0] nonane

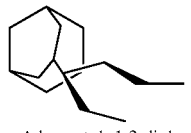
Adamantyl -1,2-diyl

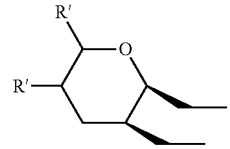
substituted tetrahydropyran

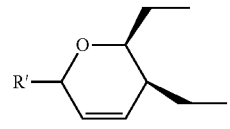
Substituted dihydropyran

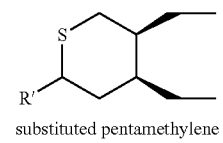
substituted pentamethylene sulphide (substituted tetrahydro- thiopyran

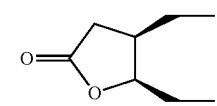
Tetrahydro-furan-2-one

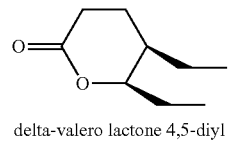
delta-valero lactone 4,5-diyl

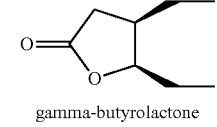
gamma-butyrolactone

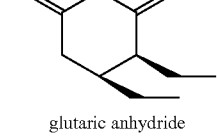
glutaric anhydride

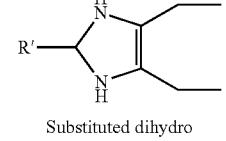
Substituted dihydro imidazole

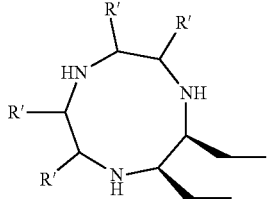
Substituted 1,4, 7 triazacyclononane

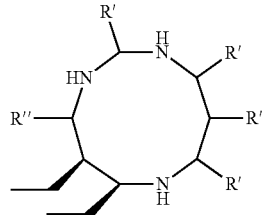
Substituted 1,5, 9 triazacyclodecane

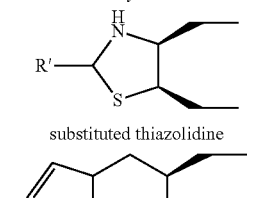
substituted thiazolidine

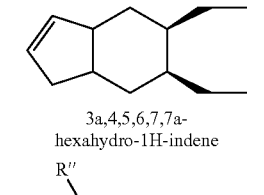
3a,4,5,6,7,7a- hexahydro-1H-indene

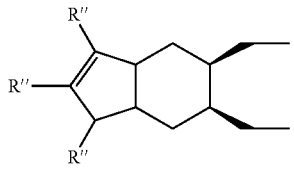
substituted 3a,4,5,6,7,7a hexahydro-1H-indene

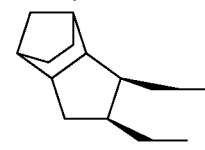
Octahydro-4, 7 methano-indene

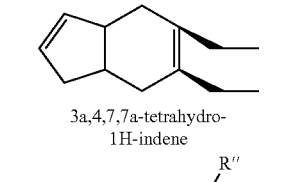
3a,4,7,7a-tetrahydro- 1H-indene

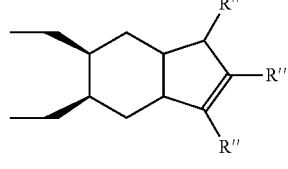
Substituted 3a,4,5,6,7,7a- hexahydro-1H-indene

In the structures herein, where there is more than one stereoisomeric form possible, all such stereoisomers are intended. However, where there are substituents it is preferable that the at least one substituent on at least one further cyclic atom of the non-aromatic bridged hydrocarbyl structure extends in a trans direction with respect to the A and or B atom i.e. extends outwardly on the opposite side of the ring.

Preferably, each adjacent cyclic atom to the said available adjacent cyclic atom is not substituted so as to form a further 3-8 atom ring structure via the other adjacent cyclic atom to the said available adjacent cyclic atoms in the at least one ring or via an atom adjacent to the said other adjacent atom but outside the at least one ring in the non-aromatic bridged structure;

An additional preferred set of embodiments is found when R represents an aromatic bridged hydrocarbyl structure i.e. having at least one aromatic ring to which $Q^1$ and $Q^2$ are each linked, via the respective linking group, on available adjacent cyclic atoms of the at least one aromatic ring. The aromatic structure may be substituted with one or more substituent(s).

The aromatic bridged hydrocarbyl structure may, where possible, be substituted with one or more substituents selected from alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)NR^{25}R^{26}$, $SR^{27}$, $C(O)SR^{27}$, or $-J-Q^3(CR^{13}(R^{14})(R^{15})CR^{16}(R^{17})(R^{18})$ where J represents lower alkylene; or two adjacent substituents together with the cyclic atoms of the ring to which they are attached form a further ring, which is optionally substituted by one or more substituents selected from alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)NR^{25}R^{26}$, $SR^{27}$ or $C(O)SR^{27}$; wherein $R^{19}$ to $R^{27}$ are defined herein.

One type of substituent for the aromatic bridged hydrocarbyl structure is the substituent $Y^x$ which may be present on one or more further cyclic atom(s), preferably aromatic cyclic atom of the aromatic bridged cyclic hydrocarbyl structure.

Preferably, when present, the substituent(s) $Y^x$ on the aromatic structure has a total $^{x=1-n}\Sigma tY^x$ of atoms other than hydrogen such that $^{x=1-n}\Sigma tY^x$ is ≥4, where n is the total number of substituent(s) $Y^x$ and $tY^x$ represents the total number of atoms other than hydrogen on a particular substituent $Y^x$.

Typically, when there is more than one substituent $Y^x$ hereinafter also referred to as simply Y, any two may be located on the same or different cyclic atoms of the aromatic bridged cyclic hydrocarbyl structure. Preferably, there are ≤10 Y groups i.e. n is 1 to 10, more preferably there are 1-6 Y groups, most preferably 1-4 Y groups on the aromatic structure and, especially, 1, 2 or 3 substituent Y groups on the aromatic structure. The substituted cyclic aromatic atoms may be carbon or hetero but are preferably carbon.

Preferably, when present, $^{x=1-n}\Sigma tY^x$ is between 4-100, more preferably, 4-60, most preferably, 4-20, especially 4-12.

Preferably, when there is one substituent Y, Y represents a group which is at least as sterically hindering as phenyl and when there are two or more substituents Y they are each as sterically hindering as phenyl and/or combine to form a group which is more sterically hindering than phenyl.

By sterically hindering herein, whether in the context of the groups $R^1$-$R^{12}$ described hereinafter or the substituent Y, or otherwise, we mean the term as readily understood by those skilled in the art but for the avoidance of any doubt, the term more sterically hindering than phenyl can be taken to mean having a lower degree of substitution (DS) than $PH_2Ph$ when $PH_2Y$ (representing the group Y) is reacted with $Ni(O)(CO)_4$ in eightfold excess according to the conditions below. Similarly, references to more sterically hindering than t-butyl can be taken as references to DS values compared with $PH_2$t-Bu etc. If, for instance, two Y groups are being compared and $PHY^1$ is not more sterically hindered than the reference then $PHY^1Y^2$ should be compared with the reference. Similarly, if three Y groups are being compared and $PHY^1$ or $PHY^1Y^2$ are not already determined to be more sterically hindered than the standard then $PY^1Y^2Y^3$ should be compared. If there are more than three Y groups they should be taken to be more sterically hindered than t-butyl.

Steric hindrance in the context of the invention herein is discussed on page 14 et seq. of "Homogenous Transition Metal Catalysis—A Gentle Art", by C. Masters, published by Chapman and Hall 1981.

Tolman ("Phosphorus Ligand Exchange Equilibria on Zerovalent Nickel. A Dominant Role for Steric Effects", Journal of American Chemical Society, 92, 1970, 2956-2965) has concluded that the property of the ligands which primarily determines the stability of the Ni(O) complexes is their size rather than their electronic character.

To determine the relative steric hindrance of a group Y or other substituent the method of Tolman to determine DS may be used on the phosphorus analogue of the group to be determined as set out above.

Toluene solutions of $Ni(CO)_4$ were treated with an eightfold excess of phosphorus ligand; substitution of CO by ligand was followed by means of the carbonyl stretching vibrations in the infrared spectrum. The solutions were equilibrated by heating in sealed tubes for 64 hr at 100°. Further heating at 100° for an additional 74 hrs did not significantly change the spectra. The frequencies and intensities of the carbonyl stretching bands in the spectra of the equilibrated solutions are then determined. The degree of substitution can be estimated semi-quantitatively from the relative intensities and the assumption that the extinction coefficients of the bands are all of the same order of magnitude. For example, in the case of $P(C_6H_{11})_3$ the $A_1$ band of $Ni(CO)_3L$ and the $B_1$ band of $Ni(CO)_2L_2$ are of about the same intensity, so that the degree of substitution is estimated at 1.5. If this experiment fails to distinguish the respective ligands then the diphenyl phosphorus $PPh_2H$ or di-t-butyl phosphorus should be compared to the $PY_2H$ equivalent as the case may be. Still further, if this also fails to distinguish the ligands then the $PPh_3$ or $P(^tBu)_3$ ligand should be compared to $PY_3$, as the case may be. Such further experimentation may be required with small ligands which fully substitute the $Ni(CO)_4$ complex.

The group Y may also be defined by reference to its cone angle which can be defined in the context of the invention as the apex angle of a cylindrical cone centred at the midpoint of the aromatic ring. By midpoint is meant a point in the plane of the ring which is equidistant from the cyclic ring atoms.

Preferably, the cone angle of the at least one group Y or the sum of the cone angles of two or more Y groups is at least 10°, more preferably, at least 20°, most preferably, at least 30°. Cone angle should be measured according to the method of Tolman {C. A. Tolman Chem. Rev. 77, (1977), 313-348} except that the apex angle of the cone is now centred at the midpoint of the aromatic ring. This modified use of Tolman cone angles has been used in other systems to measure steric effects such as those in cyclopentadienyl zirconium ethene polymerisation catalysts (Journal of Molecular Catalysis: Chemical 188, (2002), 105-113).

The substituents Y are selected to be of the appropriate size to provide steric hindrance with respect to the active site between the $Q^1$ and $Q^2$ atoms. However, it is not known whether the substituent is preventing the metal leaving, directing its incoming pathway, generally providing a more stable catalytic confirmation, or acting otherwise.

A particularly preferred ligand is found when Y represents —$SR^{40}R^{41}R^{42}$ wherein S represents Si, C, N, S, O or aryl and $R^{40}R^{41}R^{42}$ are as defined hereinafter. Preferably each Y and/or combination of two or more Y groups is at least as sterically hindering as t-butyl.

More preferably, when there is only one substituent Y, it is at least as sterically hindering as t-butyl whereas where there are two or more substituents Y, they are each at least as sterically hindering as phenyl and at least as sterically hindering as t-butyl if considered as a single group.

Preferably, when S is aryl, $R^{40}$, $R^{41}$ and $R^{42}$ are independently hydrogen, alkyl, —$BQ^3$-$X^3$($X^4$) (wherein B, $X^3$ and $X^4$ are as defined herein and $Q^3$ is defined as $Q^1$ or $Q^2$ above), phosphorus, aryl, arylene, alkaryl, arylenalkyl, alkenyl, alkynyl, het, hetero, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)$ $SR^{30}$, —$C(S)N(R^{27})$ $R^{28}$, —$CF_3$, —$SiR^{71}R^{72}R^{73}$ or alkylphosphorus.

Preferably, when S is Si, C, N, S or O, $R^{40}$, $R^{41}$ and $R^{42}$ are independently hydrogen, alkyl, phosphorus, aryl, arylene, alkaryl, aralkyl, arylenalkyl, alkenyl, alkynyl, het, hetero, halo, cyano, nitro, —$OR^{19}$, —$OC(O)R^{20}$, —$C(O)R^{21}$, —$C(O)OR^{22}$, —$N(R^{23})R^{24}$, $C(O)N(R^{25})^{26}$, $SR^{29}$, —$C(O)$ $SR^{30}$, —$C(S)N(R^{27})R^{28}$, —$CF_3$, —$SiR^{71}R^{72}R^{73}$, or alkylphosphorus wherein at least one of $R^{40}$-$R^{42}$ is not hydrogen and wherein $R^{19}$-$R^{30}$ are as defined herein; and $R^{71}$-$R^{73}$ are defined as $R^{40}$-$R^{42}$ but are preferably $C_1$-$C_4$ alkyl or phenyl.

Preferably, S is Si, C or aryl. However, N, S or O may also be preferred as one or more of the Y groups in combined or in the case of multiple Y groups. For the avoidance of doubt, as oxygen or sulphur can be bivalent, $R^{40}$-$R^{42}$ can also be lone pairs.

Preferably, in addition to group Y, the aromatic bridged cyclic hydrocarbyl structure may be unsubstituted or, when possible be further substituted with groups selected from alkyl, aryl, arylene, alkaryl, aralkyl, arylenalkyl, alkenyl, alkynyl, het, hetero, halo, cyano, nitro, —$OR^{19}$, —$OC(O)$ $R^{20}$, $C(O)^{21}$, $C(O)OR^{22}$, —$N(R^{23})^{24}$, —$C(O)N(R^{25})R^{26}$, —$SR^{29}$, —$C(O)$ $SR^{30}$, —$C(S)N(R^{27})R^{28}$, —$CF_3$, —$SiR^{71}R^{72}R^{73}$, or alkylphosphorus wherein $R^{19}$-$R^{30}$ are as defined herein; and $R^{71}$-$R^{73}$ are defined as $R^{40}$-$R^{42}$ but are preferably $C_1$-$C_4$ alkyl or phenyl. In addition, the at least one aromatic ring can be part of a metallocene complex, for instance when R is a cyclopentadienyl or indenyl anion it may form part of a metal complex such as ferrocenyl, ruthenocyl, molybdenocenyl or indenyl equivalents.

Such complexes should be considered as aromatic bridged cyclic hydrocarbyl structures within the context of the present invention and when they include more than one aromatic ring, the substituent(s) $Y^x$ or otherwise may be on the same aromatic ring as that to which the $Q^1$ and $Q^2$ atoms are linked or a further aromatic ring of the structure. For instance, in the case of a metallocene, the substituents may be on any one or more rings of the metallocene structure and this may be the same or a different ring than that to which $Q^1$ and $Q^2$ are linked.

Suitable metallocene type ligands which may be substituted as defined herein will be known to the skilled person and are extensively defined in WO 04/024322. A particularly preferred Y substituent for such aromatic anions is when S is Si.

In general, however, when S is aryl, the aryl may be unsubstituted or further substituted with, in addition to $R^{40}$, $R^{41}$, $R^{42}$, any of the further substituents defined for the aromatic structure above.

More preferred Y substituents in the present invention may be selected from t-alkyl or t-alkyl, aryl such as -t-butyl or 2-phenylprop-2-yl, —$SiMe_3$, -phenyl, alkylphenyl-, phenylalkyl- or phosphinoalkyl-such as phosphinomethyl.

Preferably, when S is Si or C and one or more of $R^{40}$-$R^{42}$ are hydrogen, at least one of $R^{40}$-$R^{42}$ should be sufficiently bulky to give the required steric hindrance and such groups are preferably phosphorus, phosphinoalkyl-, a tertiary carbon bearing group such as -t-butyl, -aryl, -alkaryl, -aralkyl or tertiary silyl.

Preferably, the aromatic bridged cyclic hydrocarbyl structure has, including substituents, from 5 up to 70 cyclic atoms, more preferably, 5 to 40 cyclic atoms, most preferably, 5-22 cyclic atoms; especially 5 or 6 cyclic atoms, if not a metallocene complex.

Preferably, the aromatic bridged cyclic hydrocarbyl structure may be monocyclic or polycyclic. The cyclic aromatic atoms may be carbon or hetero, wherein references to hetero herein are references to sulphur, oxygen and/or nitrogen. However, it is preferred that the $Q^1$ and $Q^2$ atoms are linked to available adjacent cyclic carbon atoms of the at least one aromatic ring. Typically, when the cyclic hydrocarbyl structure is polycylic it is preferably bicyclic or tricyclic. The further cycles in the aromatic bridged cyclic hydrocarbyl structure may or may not themselves be aromatic and the term aromatic bridged cyclic hydrocarbyl structure should be understood accordingly. A non-aromatic cyclic ring(s) as defined herein may include unsaturated bonds. By cyclic atom is meant an atom which forms part of a cyclic skeleton.

Preferably, the aromatic bridged cyclic hydrocarbyl structure whether substituted or otherwise preferably comprises less than 200 atoms, more preferably, less than 150 atoms, more preferably, less than 100 atoms.

By the term one further cyclic atom of the aromatic bridged hydrocarbyl structure is meant any further cyclic atom in the aromatic structure which is not an available adjacent cyclic atom of the at least one aromatic ring to which the $Q^1$ or $Q^2$ atoms are linked, via the linking group.

As mentioned above, the immediate adjacent cyclic atoms on either side of the said available adjacent cyclic atoms are preferably not substituted. As an example, an aromatic phenyl ring joined to a $Q^1$ atom via position 1 on the ring and joined to a $Q^2$ atom via position 2 on the ring has preferably one or more said further aromatic cyclic atoms substituted at ring position 4 and/or 5 and two immediate adjacent cyclic atoms to the said available adjacent cyclic atoms not substituted at positions 3 and 6. However, this is only a preferred substituent arrangement and substitution at ring positions 3 and 6, for example, is possible.

The term aromatic ring or aromatic bridged means that the at least one ring or bridge to which the $Q^1$ and $Q^2$ atom are immediately linked via B & A respectively is aromatic, and aromatic should preferably be interpreted broadly to include not only a phenyl, cyclopentadienyl anion, pyrollyl, pyridinyl, type structures but other rings with aromaticity such as that found in any ring with delocalised Pi electrons able to move freely in the said ring.

Preferred aromatic rings have 5 or 6 atoms in the ring but rings with 4n+2 pi electrons are also possible such as [14]annulene, [18]annulene, etc The aromatic bridged cyclic hydrocarbyl structure may be selected from benzene-1,2 diyl, ferrocene-1,2-diyl, naphthalene-1,2-diyl, 4 or 5 methyl benzene-1,2-diyl, l'-methyl ferrocene-1,2-diyl, 4 and/or 5 t-alkylbenzene-1,2-diyl, 4,5-diphenyl-benzene-1,2-diyl, 4 and/or 5-phenylbenzene-1,2-diyl, 4,5-di-t-butyl-benzene-1,2-diyl, 4 or 5-t-butylbenzene-1,2-diyl, 2, 3, 4 and/or 5 t-alkyl-naphthalene-8,9-diyl, 1H-inden-5,6-diyl, 1, 2 and/or 3 methyl-1H-inden-5,6-diyl, 4,7 methano-1H-indene-1,2-diyl, 1, 2 and/or 3-dimethyl-1H-inden 5,6-diyls, 1,3-bis(trimethylsilyl)-isobenzofuran-5,6-diyl, 4-(trimethylsilyl)benzene-1,2 diyl, 4-phosphinomethyl benzene-1,2 diyl, 4-(2'-phenylprop-2'-yl)benzene-1,2 diyl, 4-dimethylsilylbenzene-1,2 diyl, 4-di-t-butyl, methylsilyl benzene-1,2 diyl, 4-(t-butyldimethylsilyl)-benzene-1,2 diyl, 4-t-butylsilyl-benzene-1,2 diyl, 4-(tri-t-butylsilyl)-benzene-1,2 diyl, 4-(2'-tert-butylprop-2'-yl)benzene-1,2 diyl, 4-(2',2', 3',4',4' pentamethyl-pent-3'-yl)-benzene-1,2 diyl, 4-(2',2',4', 4'-tetramethyl, 3'-t-butyl-pent-3'-yl)-benzene-1,2 diyl, 4-(or 1')t-alkylferrocene-1,2-diyl, 4,5-diphenyl-ferrocene-1,2-diyl, 4-(or 1')phenyl-ferrocene-1,2-diyl, 4,5-di-t-butyl-ferrocene-1,2-diyl, 4-(or 1')t-butylferrocene-1,2-diyl, 4-(or 1') (trimethylsilyl)ferrocene-1,2 diyl, 4-(or 1')phosphinomethyl ferrocene-1,2 diyl, 4-(or 1')(2'-phenylprop-2'-yl)ferrocene-1,2 diyl, 4-(or 1')dimethylsilylferrocene-1,2 diyl, 4-(or 1')di-t-butyl,methylsilyl ferrocene-1,2 diyl, 4-(or 1')(t-butyldimethylsilyl)-ferrocene-1,2 diyl, 4-(or 1')t-butylsilyl-ferrocene-1,2 diyl, 4-(or 1')(tri-t-butylsilyl)-ferrocene-1,2 diyl, 4-(or 1')(2'-tert-butylprop-2'-yl)ferrocene-1,2 diyl, 4-(or 1')(2',2', 3',4',4' pentamethyl-pent-3'-yl)-ferrocene-1,2 diyl, 4-(or 1') (2',2',4',4'-tetramethyl, 3'-t-butyl-pent-3'-yl)-ferrocene-1,2 diyl.

In the structures herein, where there is more than one stereoisomeric form possible, all such stereoisomers are intended.

As mentioned above, in some embodiments, there may be two substituents on further cyclic atoms of the aromatic structure. Optionally, the said two or more substituents may, especially when on neighbouring cyclic atoms, combine to form a further ring structure such as a cycloaliphatic ring structure.

Such cycloaliphatic ring structures may be saturated or unsaturated, bridged or unbridged, substituted with alkyl, Y groups as defined herein, aryl, arylene, alkaryl, aralkyl, arylenalkyl, alkenyl, alkynyl, het, hetero, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$, —$CF_3$, —$SiR^{71}R^{72}R^{73}$, or phosphinoalkyl wherein, when present, at least one of $R^{40}$-$R^{42}$ is not hydrogen and wherein $R^{19}$-$R^{30}$ are as defined herein; and $R^{71}$-$R^{73}$ are defined as $R^{40}$-$R^{42}$ but are preferably $C_1$-$C_4$ alkyl or phenyl and/or be interrupted by one or more (preferably less than a total of 4) oxygen, nitrogen, sulphur, silicon atoms or by silano or dialkyl silicon groups or mixtures thereof.

Examples of such structures include piperidine, pyridine, morpholine, cyclohexane, cycloheptane, cyclooctane, cyclononane, furan, dioxane, alkyl substituted DIOP, 2-alkyl substituted 1,3 dioxane, cyclopentanone, cyclohexanone, cyclopentene, cyclohexene, cyclohexadiene, 1,4 dithiane, piperizine, pyrollidine, thiomorpholine, cyclohexenone, bicyclo[4.2.0]octane, bicyclo[4.3.0]nonane, adamantane, tetrahydropyran, dihydropyran, tetrahydrothiopyran, tetrahydro-furan-2-one, delta valerolactone, gamma-butyrolactone, glutaric anhydride, dihydroimidazole, triazacyclononane, triazacyclodecane, thiazolidine, hexahydro-1H-indene (5,6 diyl), octahydro-4,7 methano-indene (1,2 diyl) and tetrahydro-1H-indene (5,6 diyl) al 1 of which may be unsubstituted or substituted as defined for aryl herein.

Specific but non-limiting examples of unsubstituted aromatic bridged bidentate ligands within this invention include the following: 1,2-bis-(di-tert-butylphosphinomethyl)benzene, 1,2-bis-(di-tert-pentylphosphinomethyl)benzene, 1,2-bis-(di-tert-butylphosphimethyl)naphthalene, 1,2 bis(diadamantylphosphinomethyl)benzene, 1,2 bis(di-3,5-dimethyladamantylphosphinomethyl)benzene, 1,2 bis(di-5-tert-butyladamantylphosphinomethyl)benzene, 1,2 bis(1-adamantyl tert-butyl-phosphinomethyl)benzene, 1,2-bis-(2, 2,6,6-tetramethyl-phospha-cyclohexan-4-one)-o-xylene, 1,2-bis-(2-(phospha-adamantyl))-o-xylene, 1-(diadamantylphosphinomethyl)-2-(di-tert-butylphosphinomethyl)benzene, 1-(di-tert-butylphosphinomethyl)-2-(dicongressylphosphinomethyl)benzene, 1-(di-tert-butylphosphino)-2-(phospha-adamantyl)o-xylene, 1-(diadamantylphosphino)-2-(phospha-adamantyl)o-xylene, 1-(di-tert-butylphosphino)-2-(P-(2,2,6,6-tetramethyl-phospha-cyclohexan-4-one)o-xylene, 1-(2,2,6,6-tetramethyl-phospha-cyclohexan-4-one)-2-(phospha-adamantyl)o-xylene, 1-(di-tert-butylphosphinomethyl)-2-(di-tert-butylphosphino)benzene, 1-(phospha-adamantyl)-2-(phospha-adamantyl)methylbenzene, 1-(diadamantylphosphinomethyl)-2-(diadamantylphosphino)benzene, 1-(2-(P-(2,2,6,6-tetramethyl-phospha-cyclohexan-4-one))-benzyl)-2,2,6,6-tetramethyl-phospha-cyclohexan-4-one, 1-(di-tert-butylphosphinomethyl)-2-(phospha-adamantyl)benzene, 1-(di-tert-butylphosphinomethyl)-2-(diadamantylphosphino)benzene, 1-(di-tert-butylphosphinomethyl)-2-(P-(2,2,6,6-tetramethyl-phospha-cyclohexan-4-one)benzene, 1-(tert-butyl, adamantylphosphinomethyl)-2-(di-adamantylphosphinomethyl)benzene, 1-[(P-(2,2,6,6-tetramethyl-phospha-cyclohexan-4-one)methyl)]-2-(phospha-adamantyl)benzene, 1,2-bis-(ditert-butylphosphinomethyl)ferrocene, 1,2,3-tris-(ditert-butylphosphinomethyl)ferrocene, 1,2-bis(1,3,5,7-tetramethyl-6,9,10-trioxa-2-phospha-adamantylmethyl) ferrocene, 1,2-bis-α,α-(P-(2,2,6,6-tetramethyl-phospha-cyclohexan-4-one))dimethylferrocene, and 1-(di-tert-butylphosphinomethyl)-2-(P-(2,2,6,6-tetramethyl-phospha-cyclohexan-4-one))ferrocene and 1,2-bis(1,3,5,7-tetramethyl-6,9,10-trioxa-2-phospha-adamantylmethyl) benzene; wherein "phospha-adamantyl" is selected from 2-phospha-1,3,5,7-tetramethyl-6,9,10-trioxadamantyl, 2-phospha-1,3,5-trimethyl-6,9,10 trioxadamantyl, 2-phospha-1,3,5,7-tetra(trifluoromethyl)-6,9,10-trioxadamantyl or 2-phospha-1,3,5-tri(trifluoromethyl)-6,9,10-trioxadamantyl.

Examples of suitable substituted non-aromatic bridged bidentate ligands are cis-1,2-bis(di-t-butylphosphinomethyl)-4,5-dimethyl cyclohexane; cis-1,2-bis(di-t-butylphosphinomethyl)-5-methylcyclopentane; cis-1,2-bis(2-phosphinomethyl-1,3,5,7-tetramethyl-6,9,10-trioxa-adamantyl)-4,5-dimethylcyclohexane; cis-1,2-bis(2-phosphinomethyl-1,3,5,7-tetramethyl-6,9,10-trioxa-adamantyl) 5-methylcyclopentane; cis-1,2-bis(di-adamantylphosphinomethyl)-4,5 dimethylcyclohexane; cis-1,2-bis(di-adamantylphosphinomethyl)-5-methyl cyclopentane; cis-1-(P,P adamantyl,t-butyl phosphinomethyl)-2-(di-t-butylphosphinomethyl)-4,5-dimethylcyclohexane; cis-1-(P,P adamantyl,t-butyl phosphinomethyl)-2-(di-t-butylphosphinomethyl)-5-methylcyclopentane; cis-1-(2-phosphinomethyl-1,3,5,7-tetramethyl-6,9,10-trioxa-adamantyl)-2-(di-t-butylphosphinomethyl) 4,5-dimethylcyclohexane; cis-1-(2-phosphinomethyl-1,3,5,7-tetramethyl-6,9,10-trioxa-adamantyl)-2-(di-t-butylphosphinomethyl)-5-methyl cyclopentane; cis-1-(2-phosphinomethyl-1,3,5,7-tetramethyl-6,9,10-trioxa-adamantyl)-2-(diadamantylphosphinomethyl)-5-methyl cyclohexane; cis-1-(2-phosphinomethyl-1,3,5,7-tetramethyl-6,9,10-trioxa-adamantyl)-2-(diadamantylphosphinomethyl)-5-methyl cyclopentane; cis-1-(2-phosphinomethyl-1,3,5,7-tetramethyl-6,9,10-trioxa-adamantyl)-2-(diadamantylphosphinomethyl)cyclobutane; cis-1-(di-t-butylphosphinomethyl)-2-(diadamantylphosphinomethyl)-4,5-dimethylcyclohexane; cis-1-(di-t-butylphosphinomethyl)-2-(diadamantylphosphinomethyl)-5-methyl cyclopentane; cis-1,2-bis(2-phosphinomethyl-1,3, 5-trimethyl-6,9,10-trioxatricyclo-{3.3.1.1[3.7]}decyl)-4,5-dimethyl cyclohexane; cis-1,2-bis(2-phosphinomethyl-1,3, 5-trimethyl-6,9,10-trioxatricyclo-{3.3.1.1[3.7]}decyl)-5- methyl cyclopentane; cis-1-(2-phosphinomethyl-1,3,5-trimethyl-6,9,10-trioxatricyclo-{3.3.1.1[3.7]}decyl)-2-(di-t-butylphosphinomethyl)-4,5-dimethyl cyclohexane; cis-1-(2-phosphinomethyl-1,3,5-trimethyl-6,9,10-trioxatricyclo-{3.3.1.1[3.7]}decyl)-2-(di-t-butylphosphinomethyl)-5-methyl cyclopentane; cis-1-(2-phosphinomethyl-1,3,5-trimethyl-6,9,10-trioxatricyclo-{3.3.1.1[3.7]}decyl)-2-(diadamantylphosphinomethyl)-4,5-dimethyl cyclohexane; cis-1-(2-phosphinomethyl-1,3,5-trimethyl-6,9,10-trioxatricyclo-{3.3.1.1[3.7]}decyl)-2-(diadamantylphosphinomethyl)-5-methyl cyclopentane; cis-1,2-bis-perfluoro(2-phosphinomethyl-1,3,5,7-tetramethyl-6,9,10-trioxatricyclo{3.3.1.1[3.7]}-decyl)-4,5-dimethyl cyclohexane; cis-1,2-bis-perfluoro(2-phosphinomethyl-1,3,5,7-tetramethyl-6,9,10-trioxatricyclo{3.3.1.1[3.7]}decyl)-5-methyl cyclopentane; cis-1,2-bis-(2-phosphinomethyl-1,3,5,7-tetra(trifluoro-methyl)-6,9,10-trioxatricyclo{3.3.1.1[3.7]}decyl)-4,5-dimethyl cyclohexane; cis-1,2-bis-(2-phosphinomethyl-1,3,5,7-tetra(trifluoro-methyl)-6,9,10-trioxatricyclo{3.3.1.1[3.7]}decyl)-5-methylcyclopentane; cis-1-(2-phosphino-1,3,5,7-tetramethyl-6,9,10-trioxa-adamantyl)-2-(di-t-butylphosphinomethyl)-4,5-dimethylcyclohexane; cis-1-(2-phosphinomethyl-1,3,5,7-tetramethyl-6,9,10-trioxa-adamantyl)-2-(2-phosphino-1,3,5,7-tetramethyl-6,9,10-trioxa-adamantyl)-4,5-dimethyl cyclohexane; cis-1-(di-t-butylphosphino)-2-(di-t-butylphosphinomethyl)-4,5-dimethyl cyclohexane; cis-1-(di-adamantylphosphino)-2-(di-t-butylphosphinomethyl) 4,5-dimethyl cyclohexane; cis-1-(di-adamantylphosphino)-2-(di-adamantylphosphinomethyl)-4,5-dimethyl cyclohexane; cis-1-(2-phosphino-1,3,5,7-tetramethyl-6,9,10-trioxa-adamantyl)-2-(di-adamantylphosphinomethyl)-4,5-dimethyl cyclohexane; cis-1-(P-(2,2,6,6-tetramethyl-phospha-cyclohexan-4-one))-2-(di-t-butylphosphinomethyl)-4,5-dimethyl cyclohexane; 1-[4,5-dimethyl-2-P-(2,2,6,6-tetramethyl-phospha-cyclohexan-4-one)-[1S,2R]cyclohexylmethyl]-P-2,2,6,6-tetramethyl-phospha-cyclohexan-4-one.

Examples of suitable non-substituted non-aromatic bridged bidentate ligands are cis-1,2-bis(di-t-butylphosphinomethyl)cyclohexane; cis-1,2-bis(di-t-butylphosphinomethyl)cyclopentane; cis-1,2-bis(di-t-butylphosphinomethyl)cyclobutane; cis-1,2-bis(2-phosphinomethyl-1,3,5,7-tetramethyl-6,9,10-trioxa-adamant yl)cyclohexane; cis-1,2-bis(2-phosphinomethyl-1,3,5,7-tetramethyl-6,9,10-trioxa-adamantyl)cyclopentane; cis-1,2-bis(2-phosphinomethyl-1,3,5,7-tetramethyl-6,9,10-trioxa-adamant yl)cyclobutane; cis-1,2-bis(di-adamantylphosphinomethyl)cyclohexane; cis-1,2-bis(di-adamantylphosphinomethyl)cyclopentane; cis-1,2-bis(di-adamantylphosphinomethyl)cyclobutane; cis-1,2-bis(P-(2,2,6,6-tetramethyl-phospha-cyclohexan-4-one))dimethylcyclohexane, cis-1-(P,P-adamantyl,t-butyl-phosphinomethyl)-2-(di-t-butylphosphinomethyl)cyclohexane; cis-1-(2-phosphino-1,3,5,7-tetramethyl-6,9,10-trioxa-adamantyl)-2-(di-t-butylphosphinomethyl)cyclohexane; cis-1-(2-phosphinomethyl-1,3,5,7-tetramethyl-6,9,10-trioxa-adamantyl)-2-(2-phosphino-1,3,5,7-tetramethyl-6,9,10-trioxa-adamantyl)cyclohexane; cis-1-(di-t-butylphosphino)-2-(di-t-butylphosphinomethyl)cyclohexane; cis-1-(di-adamantylphosphino)-2-(di-t-butylphosphinomethyl)cyclohexane; cis-1-(di-adamantylphosphino)-2-(di-adamantylphosphinomethyl)cyclohexane; cis-1-(2-phosphino-1,3,5,7-tetramethyl-6,9,10-trioxa-adamantyl)-2-(di-adamantylphosphinomethyl)cyclohexane; cis-1-(P-(2,2,6,6-tetramethyl-phospha-cyclohexan-4-one))-2-(di-t-butylphosphinomethyl)cyclohexane; cis-1-(P-(2,2,6,6-tetramethyl-phospha-cyclohexan-4-one))-2-(P-(2,2,6,6-tetramethyl-phospha-cyclohexan-4-one))methylcyclohexane; cis-1-(P,P-adamantyl,t-butyl-phosphinomethyl)cyclopentane; cis-1-(P,P-adamantyl,t-butyl-phosphinomethyl)-2-(di-t-butylphosphinomethyl) cyclobutane; cis-1-(2-phosphinomethyl-1,3,5,7-tetramethyl-6,9,10-trioxa-adamantyl)-2-(di-t-butylphosphinomethyl) cyclohexane; cis-1-(2-phosphinomethyl-1,3,5,7-tetramethyl-6,9,10-trioxa-adamantyl) 2 (di-t-butylphosphinomethyl)cyclopentane; cis-1-(2-phosphinomethyl-1,3,5,7-tetramethyl-6,9,10-trioxa-adamantyl)-2-(di-t-butylphosphinomethyl)cyclobutane; cis-1-(2-phosphinomethyl-1,3,5,7-tetramethyl-6,9,10-trioxa-adamantyl)-2-(diadamantylphosphinomethyl)cyclohexane; cis-1-(2-phosphinomethyl-1,3,5,7-tetramethyl-6,9,10-trioxa-adamantyl)-2-(diadamantylphosphinomethyl)cyclopentane; cis-1-(2-phosphinomethyl-1,3,5,7-tetramethyl-6,9,10-trioxa-adamantyl)-2-(diadamantylphosphinomethyl)cyclobutane; cis-1-(di-t-butylphosphinomethyl)-2-(diadamantylphosphinomethyl)cyclohexane; cis-1-(di-t-butylphosphinomethyl)-2-(diadamantylphosphinomethyl)cyclopentane; cis-1-(di-t-butylphosphinomethyl)-2-(diadamantylphosphinomethyl)cyclobutane; cis-1,2-bis(2-phosphinomethyl-1,3,5-trimethyl-6,9,10-trioxatricyclo-{3.3.1.1[3.7]}decyl)cyclohexane; cis-1,2-bis(2-phosphinomethyl-1,3,5-trimethyl-6,9,10-trioxatricyclo-{3.3.1.1[3.7]}decyl)cyclopentane; cis-1,2-bis(2-phosphinomethyl-1,3,5-trimethyl-6,9,10-trioxatricyclo-{3.3.1.1[3.7]}decyl)cyclobutane; cis-1-(2-phosphinomethyl-1,3,5-trimethyl-6,9,10-trioxatricyclo-{3.3.1.1[3.7]}decyl)-2-(di-t-butylphosphinomethyl)cyclohexane; cis-1-(2-phosphinomethyl-1,3,5-trimethyl-6,9,10-trioxatricyclo-{3.3.1.1[3.7]}decyl)-2-(di-t-butylphosphinomethyl)cyclopentane; cis-1-(2-phosphinomethyl-1,3,5-trimethyl-6,9,10-trioxatricyclo-{3.3.1.1[3.7]}decyl)-2-(di-t-butylphosphinomethyl)cyclobutane; cis-1-(2-phosphinomethyl-1,3,5-trimethyl-6,9,10-trioxatricyclo-{3.3.1.1[3.7]}decyl)-2-(diadamantylphosphinomethyl)cyclohexane; cis-1-(2-phosphinomethyl-1,3,5-trimethyl-6,9,10-trioxatricyclo-{3.3.1.1[3.7]}decyl)-2-(diadamantylphosphinomethyl)cyclopentane; cis-1-(2-phosphinomethyl-1,3,5-trimethyl-6,9,10-trioxatricyclo-{3.3.1.1[3.7]}decyl)-2-(diadamantylphosphinomethyl)cyclobutane; cis-1,2-bis-perfluoro(2-phosphinomethyl-1,3,5,7-tetramethyl-6,9,10-trioxatricyclo{3.3.1.1[3.7]}-decyl)cyclohexane; cis-1,2-bis-perfluoro(2-phosphinomethyl-1,3,5,7-tetramethyl-6,9,10-trioxatricyclo{3.3.1.1[3.7]}decyl)cyclopentane; cis-1,2-bis-perfluoro(2-phosphinomethyl-1,3,5,7-tetramethyl-6,9,10-trioxatricyclo{3.3.1.1[3.7]}decyl)cyclobutane; cis-1,2-bis-(2-phosphinomethyl-1,3,5,7-tetra(trifluoro-methyl)-6,9,10-trioxatricyclo{3.3.1.1[3.7]}decyl)cyclohexane; cis-1,2-bis-(2-phosphinomethyl-1,3,5,7-tetra(trifluoro-methyl)-6,9,10-trioxatricyclo{3.3.1.1[3.7]}decyl)cyclopentane; and cis-1,2-bis-(2-phosphinomethyl-1,3,5,7-tetra(trifluoro-methyl)-6,9,10-trioxatricyclo{3.3.1.1[3.7]}decyl)cyclobutane, (2-exo,3-exo)-bicyclo[2.2.1]heptane-2,3-bis(di-tert-butylphosphinomethyl) and (2-endo, 3-endo)-bicyclo[2.2.1]heptane-2,3-bis(di-tert-butylphosphinomethyl).

Examples of substituted aromatic bridged ligands in accordance with the invention include 1,2-bis(di-t-butylphosphinomethyl)-4,5-diphenyl benzene; 1,2-bis(di-t-butylphosphinomethyl)-4-phenylbenzene; 1,2-bis(di-t-butylphosphinomethyl)-4,5-bis-(trimethylsilyl)benzene; 1,2-bis(di-t-butylphosphinomethyl)-4-(trimethylsilyl)benzene; 1,2-bis(2-phosphinomethyl-1,3,5,7-tetramethyl-6,9,10-trioxa-adamantyl)-4,5-diphenylbenzene; 1,2-bis(2-phosphinomethyl-1,3,5,7-tetramethyl-6,9,10-trioxa-adamantyl)-4-phenylbenzene; 1,2-bis(2-phosphinomethyl-1,3,5,7-tetramethyl-6,9,10-trioxa-adamantyl)-4,5-bis-(trimethylsilyl)benzene; 1,2-bis(2-phosphinomethyl-1,3,5,7-tetramethyl-6,9,10-trioxa-adamantyl)-4-(trimethylsilyl)benzene; 1,2-bis(di-adamantylphosphinomethyl)-4,5 diphenylbenzene; 1,2-bis(di-adamantylphosphinomethyl)-4-phenyl benzene; 1,2-bis(di-adamantylphosphinomethyl)-4,5 bis-(trimethylsilyl)benzene; 1,2-bis(di-adamantylphosphinomethyl)-4-(trimethylsilyl)benzene; 1-(P,P adamantyl,t-butyl phosphinomethyl)-2-(di-t-butylphosphinomethyl)-4,5-diphenylbenzene; 1-(P,P adamantyl,t-butylphosphinomethyl)-2-(di-t-butylphosphinomethyl)-4-phenylbenzene; 1-(P,P adamantyl,t-butyl phosphinomethyl)-2-(di-t-butylphosphinomethyl)-4,5-bis-(trimethylsilyl) benzene; 1-(P,P adamantyl,t-butyl phosphinomethyl)-2-(di-t-butylphosphinomethyl)-4-(trimethylsilyl)benzene; 1-(2-phosphinomethyl-1,3,5,7-tetramethyl-6,9,10-trioxa-adamantyl)-2-(di-t-butylphosphinomethyl) 4,5-diphenylbenzene; 1-(2-phosphinomethyl-1,3,5,7-tetramethyl-6,9,10-trioxa-adamantyl)-2-(di-t-butylphosphinomethyl)-4-phenyl benzene; 1-(2-phosphinomethyl-1,3,5,7-tetramethyl-6,9,10-trioxa-adamantyl) 2 (di-t-butylphosphinomethyl)-4,5-bis-(trimethylsilyl)benzene; 1-(2-phosphinomethyl-1,3,5,7-tetramethyl-6,9,10-trioxa-adamantyl)-2 (di-t-butylphosphinomethyl)-4-(trimethylsilyl)benzene; 1-(2-phosphinomethyl-1,3,5,7-tetramethyl-6,9,10-trioxa-adamantyl)-2-(diadamantylphosphinomethyl)-4,5-diphenyl benzene; 1-(2-phosphinomethyl-1,3,5,7-tetramethyl-6,9,10-trioxa-adamantyl)-2-(diadamantylphosphinomethyl)-4-phenyl benzene; 1-(2-phosphinomethyl-1,3,5,7-tetramethyl-6,9,10-trioxa-adamantyl)-2-(diadamantylphosphinomethyl)-4,5-bis-(trimethylsilyl)benzene; 1-(2-phosphinomethyl-1,3,5,7-tetramethyl-6,9,10-trioxa-adamantyl)-2-(diadamantylphosphinomethyl)-4-(trimethylsilyl)benzene; 1-(di-t-butylphosphinomethyl)-2-(diadamantylphosphinomethyl)-4,5-diphenyl benzene; 1-(di-t-butylphosphinomethyl)-2-(diadamantylphosphinomethyl)-4-phenyl benzene; 1-(di-t-butylphosphinomethyl)-2-(diadamantylphosphinomethyl)-4,5-bis-(trimethylsilyl)benzene; 1-(di-t-butylphosphinomethyl)-2-(diadamantylphosphinomethyl)-4-(trimethylsilyl)benzene; 1,2-bis(2-phosphinomethyl-1,3,5-trimethyl-6,9,10-trioxatricyclo-{3.3.1.1[3.7]}decyl)-4,5-diphenyl benzene; 1,2-bis(2-phosphinomethyl-1,3,5-trimethyl-6,9,10-trioxatricyclo-{3.3.1.1[3.7]}decyl)-4-phenyl benzene; 1,2-bis(2-phosphinomethyl-1,3,5-trimethyl-6,9,10-trioxatricyclo-{3.3.1.1[3.7]}decyl)-4,5-bis-(trimethylsilyl)benzene; 1,2-bis(2-phosphinomethyl-1,3,5-trimethyl-6,9,10-trioxatricyclo-{3.3.1.1[3.7]}decyl)-4-(trimethylsilyl)benzene; 1-(2-phosphinomethyl-1,3,5-trimethyl-6,9,10-trioxatricyclo-{3.3.1.1[3.7]}decyl)-2-(di-t-butylphosphinomethyl)-4,5-diphenyl benzene; 1-(2-phosphinomethyl-1,3,5-trimethyl-6,9,10-trioxatricyclo-{3.3.1.1[3.7]}decyl)-2-(di-t-butylphosphinomethyl)-4-phenyl benzene; 1-(2-phosphinomethyl-1,3,5-trimethyl-6,9,10-trioxatricyclo-{3.3.1.1[3.7]}decyl)-2-(di-t-butylphosphinomethyl)-4,5-bis-(trimethylsilyl)benzene; 1-(2-phosphinomethyl-1,3,5-trimethyl-6,9,10-trioxatricyclo-{3.3.1.1[3.7]}decyl)-2-(di-t-butylphosphinomethyl)-4-(trimethylsilyl)benzene; 1-(2-phosphinomethyl-1,3,5-trimethyl-6,9,10-trioxatricyclo-{3.3.1.1[3.7]}decyl)-2-(diadamantylphosphinomethyl)-4,5-diphenyl benzene; 1-(2-phosphinomethyl-1,3,5-trimethyl-6,9,10-trioxatricyclo-{3.3.1.1[3.7]}decyl)-2-(diadamantylphosphinomethyl)-4-phenyl benzene; 1-(2-phosphinomethyl-1,3,5-trimethyl-6,9,10-trioxatricyclo-{3.3.1.1[3.7]}decyl)-2-(diadamantylphosphinomethyl)-4,5-bis-(trimethylsilyl)benzene; 1-(2-phosphinomethyl-1,3,5-trimethyl-6,9,10-trioxatricyclo-{3.3.1.1[3.7]}decyl)-2-(diadamantylphosphinomethyl)-4-(trimethylsilyl)benzene; 1,2-bis-perfluoro(2-phosphinomethyl-1,3,5,7-tetramethyl-6,9,10-trioxatricyclo{3.3.1.1[3.7]}-decyl)-4,5-diphenyl benzene; 1,2-bis-perfluoro(2-phosphinomethyl-1,3,5,7-tetramethyl-6,9,10-trioxatricyclo{3.3.1.1[3.7]}decyl)-4-phenyl benzene; 1,2-bis-perfluoro(2-phosphinomethyl-1,3,5,7-tetramethyl-6,9,10-trioxatricyclo{3.3.1.1[3.7]}-decyl)-4,5-bis-(trimethylsilyl)benzene; 1,2-bis-perfluoro(2-phosphinomethyl-1,3,5,7-tetramethyl-6,9,10-trioxatricyclo{3.3.1.1[3.7]}decyl)-4-(trimethylsilyl)benzene; 1,2-bis-(2-phosphinomethyl-1,3,5,7-tetra(trifluoro-methyl)-6,9,10-trioxatricyclo{3.3.1.1[3.7]}decyl)-4,5-diphenyl benzene; 1,2-bis-(2-phosphinomethyl-1,3,5,7-tetra(trifluoro-methyl)-6,9,10-trioxatricyclo{3.3.1.1[3.7]}decyl)-4-phenyl benzene; 1,2-bis-(2-phosphinomethyl-1,3,5,7-tetra(trifluoro-methyl)-6,9,10-trioxatricyclo{3.3.1.1[3.7]}decyl)-4,5-bis-(trimethylsilyl)benzene; 1,2-bis-(2-phosphinomethyl-1,3,5,7-tetra(trifluoro-methyl)-6,9,10-trioxatricyclo{3.3.1.1[3.7]}decyl)-4-(trimethylsilyl)benzene; 1,2-bis(di-t-butylphosphinomethyl)-4,5-di-(2'-phenylprop-2'-yl)benzene; 1,2-bis(di-t-butylphosphinomethyl)-4-(2'-phenylprop-2'-yl)benzene; 1,2-bis(di-t-butylphosphinomethyl)-4,5-di-t-butyl benzene; 1,2-bis(di-t-butylphosphinomethyl)-4-t-butylbenzene; 1,2-bis(2-phosphinomethyl-1,3,5,7-tetramethyl-6,9,10-trioxa-adamantyl)-4,5-di-(2'-phenylprop-2'-yl)benzene; 1,2-bis(2-phosphinomethyl-1,3,5,7-tetramethyl-6,9,10-trioxa-adamantyl)-4-(2'-phenylprop-2'-yl)benzene; 1,2-bis(2-phosphinomethyl-1,3,5,7-tetramethyl-6,9,10-trioxa-adamantyl)-4,5-(di-t-butyl)benzene; 1,2-bis(2-phosphinomethyl-1,3,5,7-tetramethyl-6,9,10-trioxa-adamantyl)-4-t-butylbenzene; 1,2-bis(di-adamantylphosphinomethyl)-4,5-di-(2'-phenylprop-2'-yl)benzene; 1,2-bis(di-adamantylphosphinomethyl)-4-(2'-phenylprop-2'-yl)benzene; 1,2-bis(di-adamantylphosphinomethyl)-4,5-(di-t-butyl)benzene; 1,2-bis(di-adamantylphosphinomethyl)-4-t-butyl benzene; 1-(P,P adamantyl,t-butyl phosphinomethyl)-2-(di-t-butylphosphinomethyl)-4,5-di-(2'-phenylprop-2'-yl)benzene; 1-(P,P adamantyl,t-butyl phosphinomethyl)-2-(di-t-butylphosphinomethyl)-4-(2'-phenylprop-2'-yl)benzene; 1-(P,P adamantyl,t-butyl phosphinomethyl)-2-(di-t-butylphosphinomethyl)-4,5-(di-t-butyl)benzene; 1-(P,P adamantyl,t-butyl phosphinomethyl)-2-(di-t-butylphosphinomethyl)-4-t-butylbenzene; 1-(2-phosphinomethyl-1,3,5,7-tetramethyl-6,9,10-trioxa-adamantyl)-2-(di-t-butylphosphinomethyl)-4,5-di-(2'-phenylprop-2'-yl)benzene; 1-(2-phosphinomethyl-1,3,5,7-tetramethyl-6,9,10-trioxa-adamantyl)-2-(di-t-butylphosphinomethyl)-4-(2'-phenylprop-2'-yl)benzene; 1-(2-phosphinomethyl-1,3,5,7-tetramethyl-6,9,10-trioxa-adamantyl)-2-(di-t-butylphosphinomethyl)-4,5-(di-t-butyl)benzene; 1-(2-phosphinomethyl-1,3,5,7-tetramethyl-6,9,10-trioxa-adamantyl) 2 (di-t-butylphosphinomethyl)-4-t-butyl benzene; 1-(2-phosphinomethyl-1,3,5,7-tetramethyl-6,9,10-trioxa-adamantyl)-2-(diadamantylphosphinomethyl)-4,5-di-(2'-phenylprop-2'-yl)benzene; 1-(2-phosphinomethyl-1,3,5,7-tetramethyl-6,9,10-trioxa-adamantyl)-2-(diadamantylphosphinomethyl)-4-(2'-phenylprop-2'-yl) benzene; 1-(2-phosphinomethyl-1,3,5,7-tetramethyl-6,9,10-trioxa-adamantyl)-2-(diadamantylphosphinomethyl)-4,5-(di-t-butyl)benzene; 1-(2-phosphinomethyl-1,3,5,7-tetramethyl-6,9,10-trioxa-adamantyl)-2-(diadamantylphosphinomethyl)-4-t-butyl benzene; 1-(di-t-butylphosphinomethyl)-2-(diadamantylphosphinomethyl)-4,5-di-(2'-phenylprop-2'-yl)benzene; 1-(di-t- butylphosphinomethyl)-2-(diadamantylphosphinomethyl)-4-(2'-phenylprop-2'-yl) be 1-(di-t-butylphosphinomethyl)-2-(diadamantylphosphinomethyl)-4,5-(di-t-butyl)benzene; 1-(di-t-butylphosphinomethyl)-2-(diadamantylphosphinomethyl)-4-t-butyl benzene; 1,2-bis(2-phosphinomethyl-1,3,5-trimethyl-6,9,10-trioxatricyclo-{3.3.1.1[3.7]}decyl)-4,5-di-(2'-phenylprop-2'-yl)benzene; 1,2-bis(2-phosphinomethyl-1,3,5-trimethyl-6,9,10-trioxatricyclo-{3.3.1.1[3.7]}decyl)-4-(2'-phenylprop-2'-yl)benzene; 1,2-bis(2-phosphinomethyl-1,3,5-trimethyl-6,9,10-trioxatricyclo-{3.3.1.1[3.7]}decyl)-4,5-(di-t-butyl)benzene; 1,2-bis(2-phosphinomethyl-1,3,5-trimethyl-6,9,10-trioxatricyclo-{3.3.1.1[3.7]}decyl)-4-t-butyl benzene; 1-(2-phosphinomethyl-1,3,5-trimethyl-6,9,10-trioxatricyclo-{3.3.1.1[3.7]}decyl)-2-(di-t-butylphosphinomethyl)-4,5-di-(2'-phenylprop-2'-yl)benzene; 1-(2-phosphinomethyl-1,3,5-trimethyl-6,9,10-trioxatricyclo-{3.3.1.1[3.7]}decyl)-2-(di-t-butylphosphinomethyl)-4-(2'-phenylprop-2'-yl)benzene; 1-(2-phosphinomethyl-1,3,5-trimethyl-6,9,10-trioxatricyclo-{3.3.1.1[3.7]}decyl)-2-(di-t-butylphosphinomethyl)-4,5-(di-t-butyl)benzene; 1-(2-phosphinomethyl-1,3,5-trimethyl-6,9,10-trioxatricyclo-{3.3.1.1[3.7]}decyl)-2-(di-t-butylphosphinomethyl)-4-t-butyl benzene; 1-(2-phosphinomethyl-1,3,5-trimethyl-6,9,10-trioxatricyclo-{3.3.1.1[3.7]}decyl)-2-(diadamantylphosphinomethyl)-4,5-di-(2'-phenylprop-2'-yl)benzene; 1-(2-phosphinomethyl-1,3,5-trimethyl-6,9,10-trioxatricyclo-{3.3.1.1[3.7]}decyl)-2-(diadamantylphosphinomethyl)-4-(2'-phenylprop-2'-yl)benzene; 1-(2-phosphinomethyl-1,3,5-trimethyl-6,9,10-trioxatricyclo-{3.3.1.1[3.7]}decyl)-2-(diadamantylphosphinomethyl)-4,5-(di-t-butyl)benzene; 1-(2-phosphinomethyl-1,3,5-trimethyl-6,9,10-trioxatricyclo-{3.3.1.1[3.7]}decyl)-2-(diadamantylphosphinomethyl)-4-t-butyl benzene; 1,2-bis-perfluoro(2-phosphinomethyl-1,3,5,7-tetramethyl-6,9,10-trioxatricyclo{3.3.1.1[3.7]}-decyl)-4,5-di-(2'-phenylprop-2'-yl)benzene; 1,2-bis-perfluoro(2-phosphinomethyl-1,3,5,7-tetramethyl-6,9,10-trioxatricyclo{3.3.1.1[3.7]}decyl)-4-(2'-phenylprop-2'-yl)benzene; 1,2-bis-perfluoro(2-phosphinomethyl-1,3,5,7-tetramethyl-6,9,10-trioxatricyclo{3.3.1.1[3.7]}-decyl)-4,5-(di-t-butyl)benzene; 1,2-bis-perfluoro(2-phosphinomethyl-1,3,5,7-tetramethyl-6,9,10-trioxatricyclo{3.3.1.1[3.7]}decyl)-4-t-butyl benzene; 1,2-bis-(2-phosphinomethyl-1,3,5,7-tetra(trifluoro-methyl)-6,9,10-trioxatricyclo{3.3.1.1[3.7]}decyl)-4,5-di-(2'-phenylprop-2'-yl)benzene; 1,2-bis-(2-phosphinomethyl-1,3,5,7-tetra(trifluoro-methyl)-6,9,10-trioxatricyclo{3.3.1.1[3.7]}decyl)-4-(2'-phenylprop-2'-yl)benzene; 1,2-bis-(2-phosphinomethyl-1,3,5,7-tetra(trifluoro-methyl)-6,9,10-trioxatricyclo{3.3.1.1[3.7]}decyl)-4,5-(di-t-butyl)benzene; 1,2-bis-(2-phosphinomethyl-1,3,5,7-tetra(trifluoro-methyl)-6,9,10-trioxatricyclo{3.3.1.1[3.7]}decyl)-4-t-butyl benzene, 1,2-bis-(P-(2,2,6,6-tetramethyl-phosphinomethyl-cyclohexan-4-one)-4-(trimethylsilyl)benzene, 1-(di-tert-butylphosphinomethyl)-2-(phospha-adamantyl)-4-(trimethylsilyl)benzene, 1-(diadamantylphosphinomethyl)-2-(phospha-adamantyl)-4-(trimethylsilyl)benzene, 1-(phospha-adamantyl)-2-(phospha-adamantyl)-4-(trimethylsilyl)methylbenzene, 1-(di-tert-butylphosphinomethyl)-2-(di-tert-butylphosphino)-4-(trimethylsilyl)benzene, 1-(di-adamantylphosphinomethyl)-2-(diadamantylphosphino)-4-(trimethylsilyl)benzene, 1-(di-tert-butylphosphinomethyl)-2-(diadamantylphosphino)-4-(trimethylsilyl)benzene, 1-(di-tert-butylphosphinomethyl)-2-(P-(2,2,6,6-tetramethyl-phospha-cyclohexan-4-one)-4-(trimethylsilyl)benzene, 1-(di-tert-butylphosphinomethyl)-2-(P-(2,2,6,6-tetramethyl-phospha-cyclohexan-4-one)-4-(trimethylsilyl)benzene, 1-(2-(P-(2,2,6,6-tetramethyl-phospha-cyclohexan-4-one))-4-trimethylsilylbenzyl)-2,2,6,6-tetramethyl-phospha-cyclohexan-4-one, 1-(tert-butyl, adamantylphosphino)-2-(di-adamantylphosphinomethyl)-4-(trimethylsilyl)benzene- and wherein "phospha-adamantyl" is selected from 2-phospha-1,3,5,7-tetramethyl-6,9,10-trioxadamantyl, 2-phospha-1,3,5-trimethyl-6,9,10 trioxadamantyl, 2-phospha-1,3,5,7-tetra(trifluoromethyl)-6,9,10-trioxadamantyl or 2-phospha-1,3,5-tri(trifluoromethyl)-6,9,10-trioxadamantyl-, 1-(ditert-butylphosphinomethyl)-2-(P-(2,2,6,6-tetramethyl-phospha-cyclohexan-4-one))-4-(trimethylsilyl)ferrocene, 1,2-bis(di-t-butylphosphinomethyl)-4,5-diphenyl ferrocene; 1,2-bis(di-t-butylphosphinomethyl)-4-(or 1')phenylferrocene; 1,2-bis(di-t-butylphosphinomethyl)-4,5-bis-(trimethylsilyl)ferrocene; 1,2-bis(di-t-butylphosphinomethyl)-4-(or 1')(trimethylsilyl)ferrocene; 1,2-bis(2-phosphinomethyl-1,3,5,7-tetramethyl-6,9,10-trioxa-adamantyl)-4,5-diphenylferrocene; 1,2-bis(2-phosphinomethyl-1,3,5,7-tetramethyl-6,9,10-trioxa-adamant yl) 4-(or 1')phenylferrocene; 1,2-bis(2-phosphinomethyl-1,3,5,7-tetramethyl-6,9,10-trioxa-adamantyl)-4,5-bis-(trimethylsilyl)ferrocene; 1,2-bis(2-phosphinomethyl-1,3,5,7-tetramethyl-6,9,10-trioxa-adamant yl) 4-(or 1')(trimethylsilyl)ferrocene; 1,2-bis(di-adamantylphosphinomethyl)-4,5 diphenylferrocene; 1,2-bis (di-adamantylphosphinomethyl)-4-(or 1')phenyl ferrocene; 1,2-bis(di-adamantylphosphinomethyl)-4,5 bis-(trimethylsilyl)ferrocene; 1,2-bis(di-adamantylphosphinomethyl)-4-(or 1')(trimethylsilyl)ferrocene; 1-(P,P adamantyl,t-butyl phosphinomethyl)-2-(di-t-butylphosphinomethyl)-4,5-diphenyl-ferrocene; 1-(P,P adamantyl,t-buty l phosphinomethyl)-2-(di-t-butylphosphinomethyl)-4-(or 1')phenylferrocene; 1-(P,P adamantyl,t-butylphosphinomethyl)-2-(di-t-butylphosphinomethyl)-4,5-bis-(trimethylsilyl)ferrocene; 1-(P,P adamantyl,t-butyl phosphinomethyl)-2-(di-t-butylphosphinomethyl)-4-(or 1')(trimethylsilyl)ferrocene; 1-(2-phosphinomethyl-1,3,5,7-tetramethyl-6,9,10-trioxa-adamantyl)-2-(di-t-butylphosphinomethyl)4,5-diphenylferrocene; 1-(2-phosphinomethyl-1,3,5,7-tetramethyl-6,9,10-trioxa-adamantyl)-2-(di-t-butylphosphinomethyl)-4-(or 1')phenyl ferrocene; 1-(2-phosphinomethyl-1,3,5,7-tetramethyl-6,9,10-trioxa-adamantyl)-2-(di-t-butylphosphinomethyl)4,5-bis-(trimethylsilyl)ferrocene; 1-(2-phosphinomethyl-1,3,5,7-tetramethyl-6,9,10-trioxa-adamantyl)-2-(di-t-butylphosphinomethyl)-4-(or 1')(trimethylsilyl)ferrocene; 1-(2-phosphinomethyl-1,3,5,7-tetramethyl-6,9,10-trioxa-adamantyl)-2-(diadamantylphosphinomethyl)-4,5-diphenyl ferrocene; 1-(2-phosphinomethyl-1,3,5,7-tetramethyl-6,9,10-trioxa-adamantyl)-2-(diadamantylphosphinomethyl)-4-(or 1')phenyl ferrocene; 1-(2-phosphinomethyl-1,3,5,7-tetramethyl-6,9,10-trioxa-adamantyl)-2-(diadamantylphosphinomethyl)-4,5-bis-(trimethylsilyl)ferrocene; 1-(2-phosphinomethyl-1,3,5,7-tetramethyl-6,9,10-trioxa-adamantyl)-2-(diadamantylphosphinomethyl)-4-(or 1')(trimethylsilyl)ferrocene; 1-(di-t-butylphosphinomethyl)-2-(diadamantylphosphinomethyl)-4,5-diphenyl ferrocene; 1-(di-t-butylphosphinomethyl)-2-(diadamantylphosphinomethyl)-4-(or 1')phenyl ferrocene; 1-(di-t-butylphosphinomethyl)-2-(diadamantylphosphinomethyl)-4,5-bis-(trimethylsilyl)ferrocene; 1-(di-t-butylphosphinomethyl)-2-(diadamantylphosphinomethyl)-4-(or 1') (trimethylsilyl)ferrocene; 1,2-bis(2-phosphinomethyl-1,3,5-trimethyl-6,9,10-trioxatricyclo-{3.3.1.1[3.7]}decyl)-4,5-diphenyl ferrocene; 1,2-bis(2-phosphinomethyl-1,3,5-trimethyl-6,9,10-trioxatricyclo-{3.3.1.1[3.7]}decyl)-4-(or 1')phenyl ferrocene; 1,2-bis(2-phosphinomethyl-1,3,5-trimethyl-6,9,10-trioxatricyclo-{3.3.1.1[3.7]}decyl)-4,5-bis-(trimethylsilyl)ferrocene; 1,2-bis(2-phosphinomethyl-1,3,5-trimethyl-6,9,10-trioxatricyclo-{3.3.1.1[3.7]}decyl)-4-(or 1')(trimethylsilyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-diphenyl ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')phenyl ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-bis-(trimethylsilyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')(trimethylsilyl)ferrocene; 1-(2-phosphinomethyl-1,3,5-trimethyl-6,9,10-trioxatricyclo-{3.3.1.1[3.7]}decyl)-2-(di-adamantylphosphinomethyl)-4,5-diphenyl ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')phenyl ferrocene; 1-(2-phosphinomethyl-1,3,5-trimethyl-6,9,10-trioxatricyclo-{3.3.1.1[3.7]}decyl)-2-(diadamantylphosphinomethyl)-4,5-bis-(trimethylsilyl)ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')(trimethylsilyl)ferrocene; 1,2-bis-perfluoro(2-phosphinomethyl-1,3,5,7-tetramethyl-6,9,10-trioxatricyclo{3.3.1.1[3.7]}-decyl)-4,5-diphenyl ferrocene; 1,2-bis-perfluoro(2-phosphinomethyl-1,3,5,7-tetramethyl-6,9,10-trioxatricyclo{3.3.1.1[3.7]}decyl)-4-(or 1')phenyl ferrocene; 1,2-bis-perfluoro(2-phosphinomethyl-1,3,5,7-tetramethyl-6,9,10-trioxatricyclo{3.3.1.1[3.7]}-decyl)-4,5-bis-(trimethylsilyl)ferrocene; 1,2-bis-perfluoro(2-phosphinomethyl-1,3,5,7-tetramethyl-6,9,10-trioxatricyclo{3.3.1.1[3.7]}decyl)-4-(or 1')(trimethylsilyl)ferrocene; 1,2-bis-(2-phosphinomethyl-1,3,5,7-tetra(trifluoro-methyl)-6,9,10-trioxatricyclo{3.3.1.1[3.7]}decyl)-4,5-diphenyl ferrocene; 1,2-bis-(2-phosphinomethyl-1,3,5,7-tetra(trifluoro-methyl)-6,9,10-trioxatricyclo{3.3.1.1[3.7]}decyl)-4-(or 1')phenyl ferrocene; 1,2-bis-(2-phosphinomethyl-1,3,5,7-tetra(trifluoro-methyl)-6,9,10-trioxatricyclo{3.3.1.1[3.7]}decyl)-4,5-bis-(trimethylsilyl)ferrocene; 1,2-bis-(2-phosphinomethyl-1,3,5,7-tetra(trifluoro-methyl)-6,9,10-trioxatricyclo{3.3.1.1[3.7]}decyl)-4-(or 1°)(trimethylsilyl)ferrocene; 1,2-bis(di-t-butylphosphinomethyl)-4,5-di-(2'-phenylprop-2'-yl)ferrocene; 1,2-bis(di-t-butylphosphinomethyl)-4-(or 1')(2'-phenylprop-2'-yl)ferrocene; 1,2-bis(di-t-butylphosphinomethyl)-4,5-di-t-butyl ferrocene; 1,2-bis(di-t-butylphosphinomethyl)-4-(or 1') t-butylferrocene; 1,2-bis(2-phosphinomethyl-1,3,5,7-tetramethyl-6,9,10-trioxa-adamantyl)-4,5-di-(2'-phenylprop-2'-yl)ferrocene; 1,2-bis(2-phosphinomethyl-1,3,5,7-tetramethyl-6,9,10-trioxa-adamantyl)-4-(or 1')(2'-phenylprop-2'-yl)ferrocene; 1,2-bis(2-phosphinomethyl-1,3,5,7-tetramethyl-6,9,10-trioxa-adamantyl)-4,5-(di-t-butyl)ferrocene; 1,2-bis(2-phosphinomethyl-1,3,5,7-tetramethyl-6,9,10-trioxa-adamantyl)-4-(or 1') t-butylferrocene; 1,2-bis(di-adamantylphosphinomethyl)-4,5-di-(2'-phenylprop-2'-yl)ferrocene; 1,2-bis(di-adamantylphosphinomethyl)-4-(or 1')(2'-phenylprop-2'-yl)ferrocene; 1,2-bis(di-adamantylphosphinomethyl)-4,5-(di-t-butyl)ferrocene; 1,2-bis(di-adamantylphosphinomethyl)-4-(or 1')t-butyl ferrocene; 1-(P,P adamantyl,t-butyl phosphinomethyl)-2-(di-t-butylphosphinomethyl)-4,5-di-(2'-phenylprop-2'-yl)ferrocene; 1-(P,P adamantyl,t-butyl phosphinomethyl)-2-(di-t-butylphosphinomethyl)-4-(or 1')(2'-phenylprop-2'-yl)ferrocene; 1-(P,P adamantyl,t-butyl phosphinomethyl)-2-(di-t-butylphosphinomethyl)-4,5-(di-t-butyl)ferrocene; 1-(P,P adamantyl,t-butyl phosphinomethyl)-2-(di-t-butylphosphinomethyl)-4-(or 1')t-butyl ferrocene; 1-(2-phosphinomethyl-1,3,5,7-tetramethyl-6,9,10-trioxa-adamantyl)-2-(di-t-butylphosphinomethyl)-4,5-di-(2'-phenylprop-2'-yl)ferrocene; 1-(2-phosphinomethyl-1,3,5,7-tetramethyl-6,9,10-trioxa-adamantyl) 2 (di-t-butylphosphinomethyl)-4-(or 1')(2'-phenylprop-2'-yl) ferrocene; 1-(2-phosphinomethyl-1,3,5,7-tetramethyl-6,9,10-trioxa-adamantyl) 2 (di-t-butylphosphinomethyl) 4,5-(di-t-butyl)ferrocene; 1-(2-phosphinomethyl-1,3,5,7-tetramethyl-6,9,10-trioxa-adamantyl)-2-(di-t-butylphosphinomethyl)-4-(or 1') t-butylferrocene; 1-(2-phosphinomethyl-1,3,5,7-tetramethyl-6,9,10-trioxa-adamantyl)-2-(diadamantylphosphinomethyl)-4,5-di-(2'-phenylprop-2'-yl)ferrocene; 1-(2-phosphinomethyl-1,3,5,7-tetramethyl-6,9,10-trioxa-adamantyl)-2-(diadamantylphosphinomethyl)-4-(or 1')(2'-phenylprop-2'-yl)ferrocene; 1-(2-phosphinomethyl-1,3,5,7-tetramethyl-6,9,10-trioxa-adamantyl)-2-(diadamantylphosphinomethyl)-4,5-(di-t-butyl)ferrocene; 1-(2-phosphinomethyl-1,3,5,7-tetramethyl-6,9,10-trioxa-adamantyl)-2-(diadamantylphosphinomethyl)-4-(or 1') t-butylferrocene; 1-(di-t-butylphosphinomethyl)-2-(diadamantylphosphinomethyl)-4,5-di-(2'-phenylprop-2'-yl)ferrocene; 1-(di-t-butylphosphinomethyl)-2-(diadamantylphosphinomethyl)-4-(or 1')(2'-phenylprop-2'-yl)ferrocene; 1-(di-t-butylphosphinomethyl)-2-(diadamantylphosphinomethyl)-4,5-(di-t-butyl)ferrocene; 1-(di-t-butylphosphinomethyl)-2-(diadamantylphosphinomethyl)-4-(or 1') t-butylferrocene; 1,2-bis(2-phosphinomethyl-1,3,5-trimethyl-6,9,10-trioxatricyclo-{3.3.1.1[3.7]}decyl)-4,5-di-(2'-phenylprop-2'-yl)ferrocene; 1,2-bis(2-phosphinomethyl-1,3,5-trimethyl-6,9,10-trioxatricyclo-{3.3.1.1[3.7]}decyl)-4-(or 1')(2'-phenylprop-2'-yl)ferrocene; 1,2-bis(2-phosphinomethyl-1,3,5-trimethyl-6,9,10-trioxatricyclo-{3.3.1.1[3.7]}decyl)-4,5-(di-t-butyl)ferrocene; 1,2-bis(2-phosphinomethyl-1,3,5-trimethyl-6,9,10-trioxatricyclo-{3.3.1.1[3.7]}decyl)-4-(or 1') t-butylferrocene; 1-(2-phosphinomethyl-1,3,5-trimethyl-6,9,10-trioxatricyclo-{3.3.1.1[3.7]}decyl)-2-(di-t-butylphosphinomethyl)-4,5-di-(2'-phenylprop-2'-yl)ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')(2'-phenylprop-2'-yl)ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-(di-t-butyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')t-butylferrocene; 1-(2-phosphinomethyl-1,3,5-trimethyl-6,9,10-trioxatricyclo-{3.3.1.1[3.7]}decyl)-2-(diadamantylphosphinomethyl)-4,5-di-(2'-phenylprop-2'-yl)ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')(2'-phenylprop-2'-yl)ferrocene; 1-(2-phosphinomethyl-1,3,5-trimethyl-6,9,10-trioxatricyclo-{3.3.1.1[3.7]}decyl)-2-(diadamantylphosphinomethyl)-4,5-(di-t-butyl)ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1') t-butylferrocene; 1,2-bis-perfluoro(2-phosphinomethyl-1,3,5,7-tetramethyl-6,9,10-trioxatricyclo{3.3.1.1[3.7]}-decyl)-4,5-di-(2'-phenylprop-2'-yl)ferrocene; 1,2-bis-perfluoro(2-phosphinomethyl-1,3,5,7-tetramethyl-6,9,10-trioxatricyclo{3.3.1.1[3.7]}decyl)-4-(or 1')(2'-phenylprop-2'-yl)ferrocene; 1,2-bis-perfluoro(2-phosphinomethyl-1,3,5,7-tetramethyl-6,9,10-trioxatricyclo{3.3.1.1[3.7]}-decyl)-4,5-(di-t-butyl)ferrocene; 1,2-bis-perfluoro(2-phosphinomethyl-1,3,5,7-tetramethyl-6,9,10-trioxatricyclo{3.3.1.1[3.7]}decyl)-4-(or 1')t-butyl ferrocene; 1,2-bis-(2-phosphinomethyl-1,3,5,7-tetra(trifluoro-methyl)-6,9,10-trioxatricyclo{3.3.1.1[3.7]}decyl)-4,5-di-(2'-phenylprop-2'-yl)ferrocene; 1,2-bis-(2- phosphinomethyl-1,3,5,7-tetra(trifluoro-methyl)-6,9,10-trioxatricyclo{3.3.1.1[3.7]}decyl)-4-(or 1')(2'-phenylprop-2'-yl)ferrocene; 1,2-bis-(2-phosphinomethyl-1,3,5,7-tetra(trifluoro-methyl)-6,9,10-trioxatricyclo{3.3.1.1[3.7]}decyl)-4,5-(di-t-butyl)ferrocene; 1,2-bis-(2-phosphinomethyl-1,3,5,7-tetra(trifluoro-methyl)-6,9,10-trioxatricyclo{3.3.1.1[3.7]}decyl)-4-(or 1')t-butyl ferrocene.

Selected structures of ligands of the invention include:—

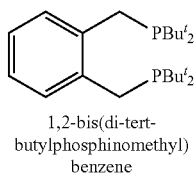

1,2-bis(di-tert-butylphosphinomethyl) benzene

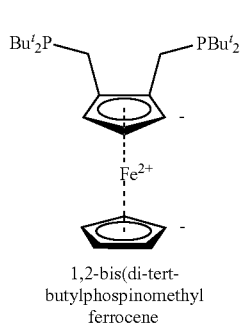

1,2-bis(di-tert-butylphospinomethyl ferrocene

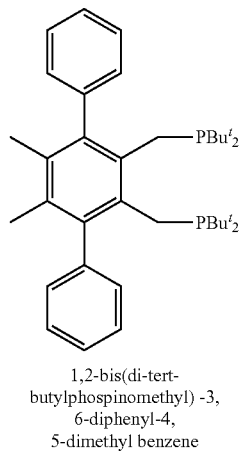

1,2-bis(di-tert-butylphospinomethyl) -3, 6-diphenyl-4, 5-dimethyl benzene

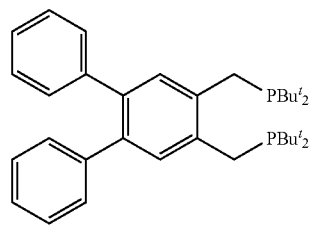

1,2-bis(di-tert-butyl (phospinomethyl) -4, 5-diphenyl benzene

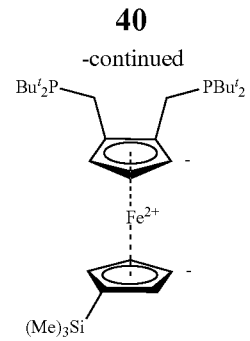

1,2-bis(di-tert-butylphosphinomethyl)-1'-trimethylsilyl ferrocene

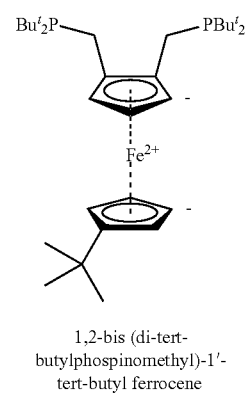

1,2-bis (di-tert-butylphosphinomethyl)-1'-tert-butyl ferrocene

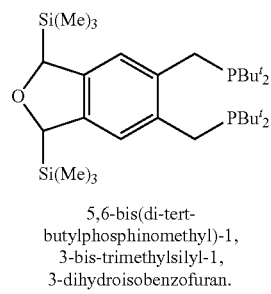

5,6-bis(di-tert-butylphosphinomethyl)-1, 3-bis-trimethylsilyl-1, 3-dihydroisobenzofuran.

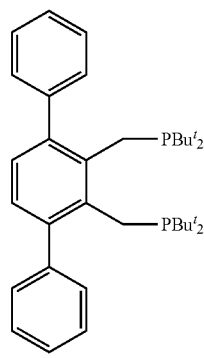

1,2-bis(di-tert-butylphosphinomethyl)-3, 6-diphenyl benzene

-continued

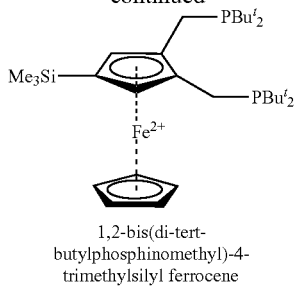

1,2-bis(di-tert-butylphosphinomethyl)-4-trimethylsilyl ferrocene

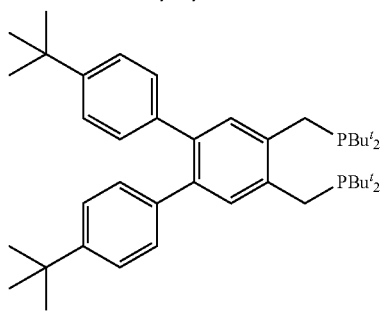

1,2 bis(di-tert-butyl(phosphinomethyl))-4,5- di(4'-tert butyl phenyl) benzene

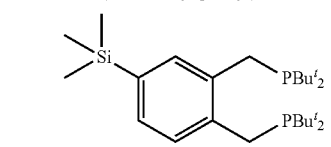

1,2-bis(di-tert-butyl(phosphinomethyl))-4-trimethylsilyl benzene

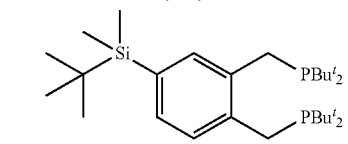

1,2-bis(di-tert-butyl(phosphinomethyl))-4-(tert-butyldimethylsilyl)benzene

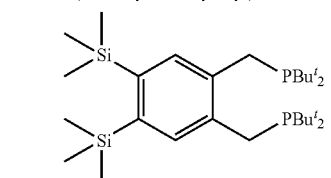

1,2-bis(di-tert-butyl(phosphinomethyl))-4,5-bis(trimethylsilyl)benzene

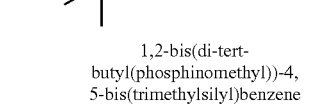

1,2-bis(di-tert-butyl(phosphinomethyl))-4-tert-butyl benzene

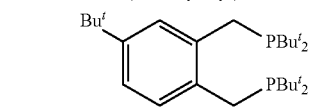

1,2-bis(di-tert-butyl(phosphinomethyl))-4,5-di-tert-butyl benzene

-continued

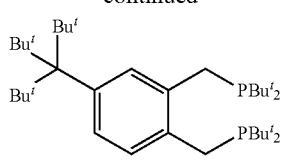

1,2-bis(di-tert-butyl(phosphinomethyl))-4-(tri-tert-butylmethyl)benzene

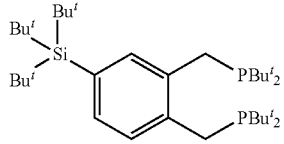

1,2-bis(di-tert-butyl(phosphinomethyl))-4-(tri-tert-butylsilyl)benzene

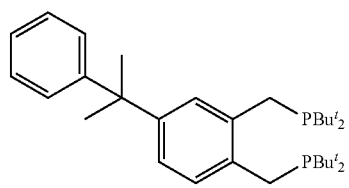

1,2-bis(di-tert-butyl(phosphinomethyl))-4-(2'-phenylprop-2'-yl)benzene

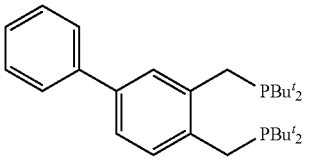

1,2-bis(di-tert-butyl(phosphinomethyl))-4-phenyl benzene

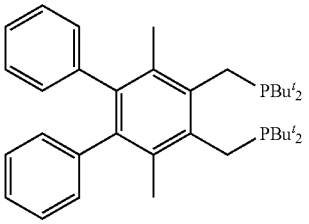

1,2-bis(di-tert-butyl(phosphinomethyl))-3,6-dimethyl-4,5-diphenyl benzene

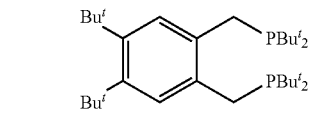

1,2-bis(di-tert-butyl(phosphinomethyl))-3,4, 5, 6-tetraphenyl benzene

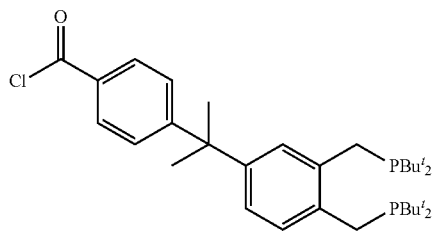

4-(1-{3,4-Bis-[(di-tert-butyl-phosphanyl)-methyl]-phenyl}-1-methyl-ethyl)-benzoyl chloride

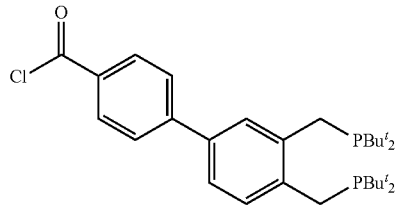

1,2-bis(di-tert-butyl(phosphinomethyl))-4-(4'-chlorocarbonyl-phenyl benzene

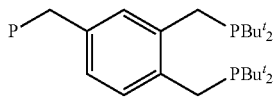

1,2-bis(di-tert-butyl(phosphinomethyl))-4-(phosphinomethyl) benzene

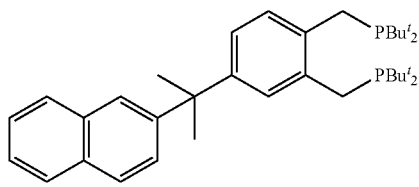

1,2-bis(di-tert-butyl(phosphinomethyl))-4-(2'-naphthylprop-2'-yl) benzene

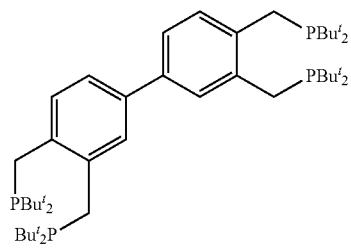

1,2-bis(di-tert-butyl(phosphinomethyl))-4-(3',4'-bis(di-tert-butyl(phospinomethyl))phenyl)benzene

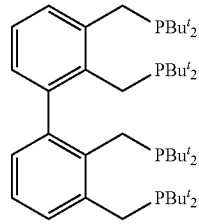

1,2-bis(di-tert-butyl(phosphinomethyl))-3-(2',3'-bis(di-tert-butyl(phospinomethyl))phenyl)benzene

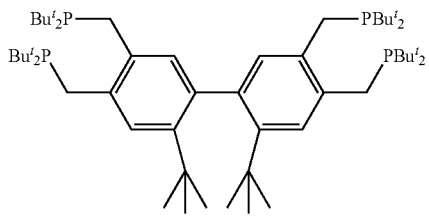

1,2-bis(di-tert-butyl(phosphinomethyl))-4-tertbutyl-5-(2'-tertbutyl-4',5'-bis(di-tert-butyl(phospinomethyl))phenyl)benzene, and

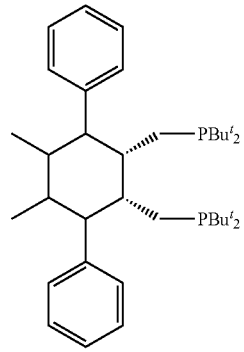

cis-1, 2-bis (di-tert-butylphosphinomethyl), 3, 6, diphenyl-4,5 dimethyl-cyclohexane,

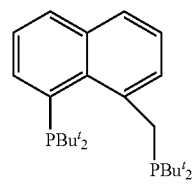

1-(di-tert-butylphosphino)-8-(di-tertbutylphosphinomethyl)-naphthalene

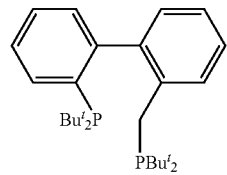

2-(di-tert-butylphosphinomethyl)-2'-(di-tert-butylphosphino)-biphenylene

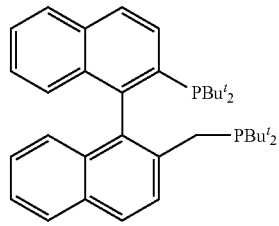

2-(di-tert-butylphosphinomethyl)-2'-(di-tert-butylphosphino)-binaphthylene

Examples of norbornyl bridge non-aromatic bridged ligands include:—

(2-exo, 3-exo)-bicyclo[2.2.1]heptane-2,3-bis[di-tert-butylphosphinomethyl)

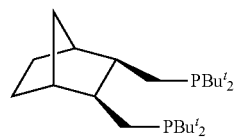

(2-endo, 3-endo)-bicyclo[2.2.1]heptane-2,3-bis[di-tert-butylphosphinomethyl)

Examples of substituted non-aromatic bridged ligand structures include:—

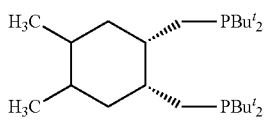

cis-1,2-bis (di-tert-butylphosphinomethyl),4,5 dimethylcyclohexane

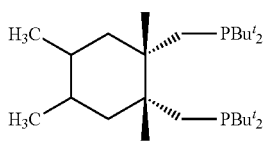

cis-1,2-bis (di-tert-butylphosphinomethyl),1,2,4,5 tetramethylcyclohexane

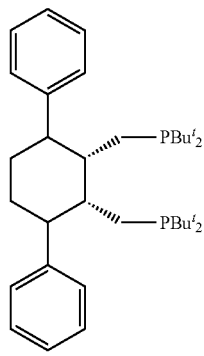

cis-1,2-bis (di-tert-butylphosphinomethyl), 3,6, diphenylcyclohexane

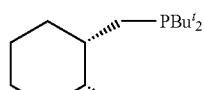

cis-1,2-bis (di-tert-butylphosphinomethyl) cyclohexane

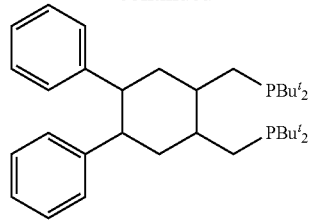

cis-1,2 bis(di-tert-butyl (phosphinomethyl)-4, 5 diphenyl cyclohexane

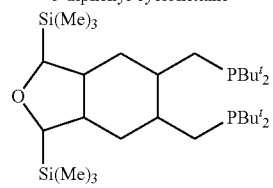

cis-5,6-bis(di-tert-butylphosphinomethyl)-1, 3- bis(trimethylsilyl)-3a,4,5,6,7,7a-hexahydro-1, 3H- isobenzofuran.

In the above example structures of ligands of general formulas (I)-(II), one or more of the $X^1$-$X^4$ tertiary carbon bearing groups, t-butyl, attached to the $Q^1$ and/or $Q^2$ group phosphorus may be replaced by a suitable alternative. Preferred alternatives are adamantyl, 1,3 dimethyl adamantyl, congressyl, norbornyl or 1-norbondienyl, or $X^1$ and $X^2$ together and/or $X^3$ and $X^4$ together form together with the phosphorus a 2-phospha-tricyclo[3.3.1.1{3,7}decyl group such as 2-phospha-1,3,5,7-tetramethyl-6,9,10-trioxadamantyl or 2-phospha-1,3,5-trimethyl-6,9,10-trioxadamantyl. In most embodiments, it is preferred that the $X^1$-$X^4$ groups or the combined $X^1/X^2$ and $X^3/X^4$ groups are the same but it may also be advantageous to use different groups to produce asymmetry around the active site in these selected ligands and generally in this invention.

Similarly, one of the linking groups A or B may be absent so that only A or B is methylene and the phosphorus atom not connected to the methylene group is connected directly to the ring carbon giving a 3 carbon bridge between the phosphorus atoms.

Typically, the group $X^1$ represents $CR^1(R^2)(R^3)$, $X^2$ represents $CR^4(R^5)(R^6)$, $X^3$ represents $CR^7(R^8)(R^9)$ and $X^4$ represents $CR^{10}(R^{11})(R^{12})$, wherein $R^1$ to $R^{12}$ represent alkyl, aryl or het.

Particularly preferred is when the organic groups $R^1$-$R^3$, $R^4$-$R^6$, $R^7$-$R^9$ and/or $R^{10}$-$R^{12}$ or, alternatively, $R^1$-$R^6$ and/or $R^7$-$R^{12}$ when associated with their respective tertiary carbon atom(s) form composite groups which are at least as sterically hindering as t-butyl(s).

The steric composite groups may be cyclic, part-cyclic or acyclic. When cyclic or part cyclic, the group may be substituted or unsubstituted or saturated or unsaturated. The cyclic or part cyclic groups may preferably contain, including the tertiary carbon atom(s), from $C_4$-$C_{34}$, more preferably $C_8$-$C_{24}$, most preferably $C_{10}$-$C_{20}$ carbon atoms in the cyclic structure. The cyclic structure may be substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, aryl or Het, wherein $R^{19}$ to $R^{30}$ are as defined herein, and/or be interrupted by one or more oxygen or sulphur atoms, or by silano or dialkylsilcon groups.

In particular, when cyclic, $X^1$, $X^2$, $X^3$ and/or $X^4$ may represent congressyl, norbornyl, 1-norbornadienyl or adamantyl, or $X^1$ and $X^2$ together with $Q^2$ to which they are attached form an optionally substituted 2-$Q^2$-tricyclo[3.3.1.1{3,7}]decyl group or derivative thereof, or $X^1$ and $X^2$ together with $Q^2$ to which they are attached form a ring system of formula 1a

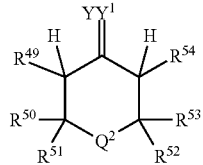

(1a)

Similarly, $X^3$ and $X^4$ together with $Q^1$ to which they are attached may form an optionally substituted 2-Q1-tricyclo[3.3.1.1{3,7}]decyl group or derivative thereof, or $X^3$ and $X^4$ together with $Q^1$ to which they are attached may form a ring system of formula 1b

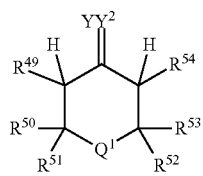

(1b)

Alternatively, one or more of the groups $X^1$, $X^2$, $X^3$ and/or $X^4$ may represent a solid phase to which the ligand is attached.

Particularly preferred is when $X^1$, $X^2$, $X^3$ and $X^4$ or $X^1$ and $X^2$ together with its respective $Q^2$ atom and $X^3$ and $X^4$ together with its respective $Q^1$ atom are the same or when $X^1$ and $X^3$ are the same whilst $X^2$ and $X^4$ are different but the same as each other.

In preferred embodiments, $R^1$ to $R^{12}$ and $R^{13}$-$R^{18}$ each independently represent alkyl, aryl, or Het;
$R^{19}$ to $R^{30}$ each independently represent hydrogen, alkyl, aryl or Het; $R^{19}$ represents hydrogen, unsubstituted $C_1$-$C_8$ alkyl or phenyl, $R^{20}$, $R^{22}$, $R^{23}$, $R^{24}$, $R^{25}$, $R^{26}$ each independently represent hydrogen or unsubstituted $C_1$-$C_8$ alkyl,
$R^{49}$ and $R^{54}$, when present, each independently represent hydrogen, alkyl or aryl;
$R^{50}$ to $R^{53}$, when present, each independently represent alkyl, aryl or Het;
$YY^1$ and $YY^2$, when present, each independently represent oxygen, sulfur or N—$R^{55}$, wherein $R^{55}$ represents hydrogen, alkyl or aryl.

Preferably, $R^1$ to $R^{12}$ herein each independently represent alkyl or aryl. More preferably, $R^1$ to $R^{12}$ each independently represent $C_1$ to $C_6$ alkyl, $C_1$-$C_6$ alkyl phenyl (wherein the phenyl group is optionally substituted as aryl as defined herein) or phenyl (wherein the phenyl group is optionally substituted as aryl as defined herein). Even more preferably, $R^1$ to $R^{12}$ each independently represent $C_1$ to $C_6$ alkyl, which is optionally substituted as alkyl as defined herein. Most preferably, $R^1$ to $R^{12}$ each represent non-substituted $C_1$ to $C_6$ alkyl such as methyl, ethyl, n-propyl, iso-propyl, n-butyl, iso-butyl, tert-butyl, pentyl, hexyl and cyclohexyl, especially methyl.

In a particularly preferred embodiment of the present invention $R^1$, $R^4$, $R^7$ and $R^{10}$ each represent the same alkyl, aryl or Het moiety as defined herein, $R^2$, $R^5$, $R^8$ and $R^{11}$ each represent the same alkyl, aryl or Het moiety as defined herein, and $R^3$, $R^6$, $R^9$ and $R^{12}$ each represent the same alkyl, aryl or Het moiety as defined herein. More preferably $R^1$, $R^4$, $R^7$ and $R^{10}$ each represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl; $R^2$, $R^5$, $R^8$ and $R^{11}$ each independently represent the same $C_1$-$C_6$ alkyl as defined above; and $R^3$, $R^6$, $R^9$ and $R^{12}$ each independently represent the same $C_1$-$C_6$ alkyl as defined above. For example: $R^1$, $R^4$, $R^7$ and $R^{10}$ each represent methyl; $R^2$, $R^5$, $R^8$ and $R^{11}$ each represent ethyl; and, $R^3$, $R^6$, $R^9$ and $R^{12}$ each represent n-butyl or n-pentyl.

In an especially preferred embodiment of the present invention each $R^1$ to $R^{12}$ group represents the same alkyl, aryl, or Het moiety as defined herein. Preferably, when alkyl groups, each $R^1$ to $R^{12}$ represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl. More preferably, each $R^1$ to $R^{12}$ represents methyl or tert-butyl, most preferably, methyl.

The 2-$Q^2$(or $Q^1$)-tricyclo[3.3.1.1.{3,7}]decyl group (referred to hereinafter as a 2-meta-adamantyl group for convenience wherein 2-meta-adamantyl is a reference to $Q^1$ or $Q^2$ being an arsenic, antimony or phosphorus atom i.e. 2-arsa-adamantyl and/or 2-stiba-adamantyl and/or 2-phospha-adamantyl, preferably, 2-phospha-adamantyl) may optionally comprise, beside hydrogen atoms, one or more substituents. Suitable substituents include those substituents as defined herein in respect of the adamantyl group. Highly preferred substituents include alkyl, particularly unsubstituted $C_1$-$C_8$ alkyl, especially methyl, trifluoromethyl, —$OR^{19}$ wherein $R^{19}$ is as defined herein particularly unsubstituted $C_1$-$C_8$ alkyl or aryl, and 4-dodecylphenyl. When the 2-meta-adamantyl group includes more than one substituent, preferably each substituent is identical.

Preferably, the 2-meta-adamantyl group is substituted on one or more of the 1, 3, 5 or 7 positions with a substituent as defined herein. More preferably, the 2-meta-adamantyl group is substituted on each of the 1, 3 and 5 positions. Suitably, such an arrangement means the Q atom of the 2-meta-adamantyl group is bonded to carbon atoms in the adamantyl skeleton having no hydrogen atoms. Most preferably, the 2-meta-adamantyl group is substituted on each of the 1, 3, 5 and 7 positions. When the 2-meta-adamantyl group includes more than 1 substituent preferably each substituent is identical. Especially preferred substituents are unsubstituted $C_1$-$C_8$ alkyl and haloakyls, particularly unsubstituted $C_1$-$C_8$ alkyl such as methyl and fluorinated $C_1$-$C_8$ alkyl such as trifluoromethyl.

Preferably, 2-meta-adamantyl represents unsubstituted 2-meta-adamantyl or 2-meta-adamantyl substituted with one or more unsubstituted $C_1$-$C_8$ alkyl substituents, or a combination thereof.

Preferably, the 2-meta-adamantyl group includes additional heteroatoms, other than the 2-Q atom, in the 2-meta-adamantyl skeleton. Suitable additional heteroatoms include oxygen and sulphur atoms, especially oxygen atoms. More preferably, the 2-meta-adamantyl group includes one or more additional heteroatoms in the 6, 9 and 10 positions. Even more preferably, the 2-meta-adamantyl group includes an additional heteroatom in each of the 6, and 10 positions. Most preferably, when the 2-meta-adamantyl group includes two or more additional heteroatoms in the 2-meta-adamantyl skeleton, each of the additional heteroatoms are identical. Preferably, the 2-meta-adamantyl includes one or more oxygen atoms in the 2-meta-adamantyl skeleton. An especially preferred 2-meta-adamantyl group, which may optionally be substituted with one or more substituents as defined herein, includes an oxygen atom in each of the 6, 9 and 10 positions of the 2-meta-adamantyl skeleton.

Highly preferred 2-meta-adamantyl groups as defined herein include 2-phospha-1,3,5,7-tetramethyl-6,9,10-trioxadamantyl, 2-phospha-1,3,5-trimethyl-6,9,10-trioxadamantyl, 2-phospha-1,3,5,7-tetra(trifluoromethyl)-6,9,10-trioxadamantyl group, and 2-phospha-1,3,5-tri(trifluoromethyl)-6,9,10-trioxadamantyl group. Most preferably, the 2-phospha-adamantyl is selected from 2-phospha-1,3,5,7-tetramethyl-6,9,10-trioxadamantyl group or 2-phospha-1,3,5-trimethyl-6,9,10-trioxadamantyl group. Preferably, when more than one 2-meta-adamantyl group is present in a compound of formula I-II, each 2-meta-adamantyl group is identical. However, it can also be advantageous if asymmetric ligands are prepared and if such ligands include a 2-meta-adamantyl group incorporating the $Q^1$ atom then other groups can be found on the $Q^2$ atom or vice versa.

The 2-meta-adamantyl group may be prepared by methods well known to those skilled in the art. Suitably, certain 2-phospha-adamantyl compounds are obtainable from Cytec Canada Inc, Canada. Likewise corresponding 2-meta-adamantyl compounds of formulas I-II etc may be obtained from the same supplier or prepared by analogous methods.

Preferred embodiments of the present invention include those wherein:

$X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$;

$X^3$ represents $CR^7(R^8)(R^9)$, $X^4$ represents $CR^{10}(R^{11})(R^{12})$, and $X^1$ and $X^2$ together with $Q^2$ to which they are attached form a 2-phospha-adamantyl group;

$X^3$ represents $CR^7(R^8)(R^9)$, $X^4$ represents $CR^{10}(R^{11})(R^{12})$; and $X^1$ and $X^2$ together with $Q^2$ to which they are attached form a ring system of formula 1a;

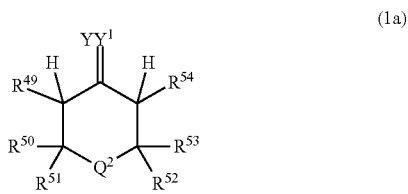

(1a)

$X^3$ represents $CR^7(R^8)(R^9)$, $X^4$ represents adamantyl, and $X^1$ and $X^2$ together with $Q^2$ to which they are attached form a 2-phospha-adamantyl group;

$X^3$ represents $CR^7(R^8)(R^9)$, $X^4$ represents adamantyl and $X^1$ and $X^2$ together with $Q^2$ to which they are attached form a ring system of formula 1a;

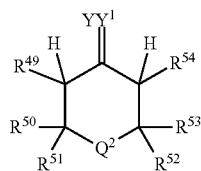

(1a)

$X^3$ represents $CR^7(R^8)(R^9)$, $X^4$ represents adamantyl, $X^1$ represents $CR^1(R^2)(R^3)$ and $X^2$ represents $CR^4(R^5)(R^6)$;

$X^3$ represents $CR^7(R^8)(R^9)$, $X^4$ represents congressyl, and $X^1$ and $X^2$ together with $Q^2$ to which they are attached form a 2-phospha-adamantyl group;

$X^3$ represents $CR^7(R^8)(R^9)$, $X^4$ represents congressyl, $X^1$ represents $CR^1(R^2)(R^3)$ and $X^2$ represents $CR^4(R^5)(R^6)$;

$X^3$ and $X^4$ independently represent adamantyl, and $X^1$ and $X^2$ together with $Q^2$ to which they are attached form a 2-phospha-adamantyl group;

$X^3$ and $X^4$ independently represent adamantyl, and $X^1$ and $X^2$ together with $Q^2$ to which they are attached form a ring system of formula 1a;

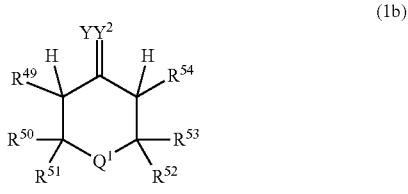

(1a)

$X^3$ and $X^4$ independently represent adamantyl, $X^1$ represents $CR^1(R^2)(R^3)$ and $X^2$ represents $CR^4(R^5)(R^6)$;

$X^1$, $X^2$, $X^3$ and $X^4$ represent adamantyl;

$X^3$ and $X^4$ together with $Q^1$ to which they are attached may form a ring system of formula 1b

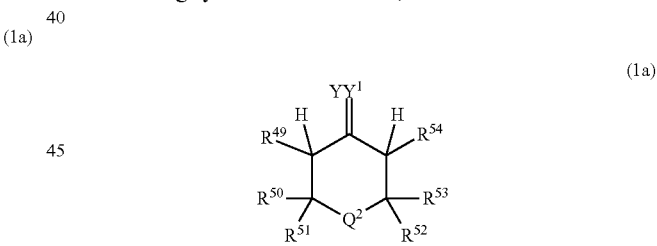

(1b)

and $X^1$ and $X^2$ together with $Q^2$ to which they are attached form a ring system of formula 1a;

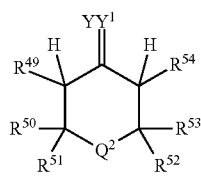

(1a)

$X^3$ and $X^4$ independently represent congressyl, and $X^1$ and $X^2$ together with $Q^2$ to which they are attached form a 2-phospha-adamantyl group;

$X^3$ and $X^4$ together with $Q^1$ to which they are attached may form a ring system of formula 1b

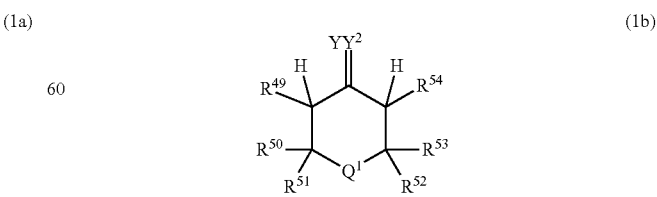

(1b)

and $X^1$ and $X^2$ together with $Q^2$, to which they are attached form a 2-phospha-adamantyl group;

$X^3$ and $X^4$ independently represent congressyl, and $X^1$ represents $CR^1(R^2)(R^3)$ and $X^2$ represents $CR^4(R^5)(R^6)$;

$X^3$ and $X^4$ together with $Q^1$ to which they are attached may form a ring system of formula 1b

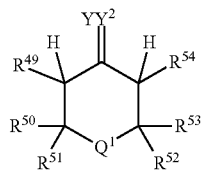

(1b)

$X^1$ represents $CR^1(R^2)(R^3)$ and $X^2$ represents $CR^4(R^5)(R^6)$;
$X^3$ and $X^4$ together with $Q^1$ to which they are attached form a 2-phospha-adamantyl group, and $X^1$ and $X^2$ together with $Q^2$ to which they are attached form a 2-phospha-adamantyl group Highly preferred embodiments of the present invention include those wherein:
$X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$; especially where $R^1$-$R^{12}$ are methyl.

Preferably in a compound of formula II, $X^3$ is identical to $X^4$ and/or $X^1$ is identical to $X^2$.

Particularly preferred combinations in the present invention include those wherein:—

(1) $X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$;
 A and B are the same and represent —$CH_2$— or A is —$CH_2$— and B is not present so that the phosphorus is joined directly to the group R;
 $Q^1$ and $Q^2$ both represent phosphorus linked to the R group at ring positions 1 and 2;
 R represents 4-(trimethylsilyl)-benzene-1,2-diyl (2) $X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$;
 A and B are the same and represent —$CH_2$— or A is —$CH_2$— and B is not present so that the phosphorus is joined directly to the group R;
 $Q^1$ and $Q^2$ both represent phosphorus linked to the R group at ring positions 1 and 2;
 R represents 4-t-butyl-benzene-1,2-diyl.

(3) $X^3$ and $X^4$ together with $Q^1$ to which they are attached form a 2-phospha-adamantyl group, and, $X^1$ and $X^2$ together with $Q^2$ to which they are attached form a 2-phospha-adamantyl group;
 A and B are the same and represent —$CH_2$— or A is —$CH_2$— and B is not present so that the phosphorus is joined directly to the group R;
 $Q^1$ and $Q^2$ both represent phosphorus linked to the R group at ring positions 1 and 2;
 R represents 4-(trimethylsilyl)-benzene-1,2-diyl.

(4) $X^1$, $X^2$, $X^3$ and $X^4$ represent adamantyl;
 A and B are the same and represent —$CH_2$— or A is —$CH_2$— and B is not present so that the phosphorus is joined directly to the group R;
 $Q^1$ and $Q^2$ both represent phosphorus linked to the R group at ring positions 1 and 2;
 R represents 4-(trimethylsilyl)-benzene-1,2-diyl.

(5) $X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$;
 A and B are the same and represent —$CH_2$— or A is —$CH_2$— and B is not present so that the phosphorus is joined directly to the group R;
 $Q^1$ and $Q^2$ both represent phosphorus linked to the R group at ring positions 1 and 2;
 R represents ferrocene or benzene-1,2-diyl (6) $X^3$ and $X^4$ together with $Q^1$ to which they are attached form a 2-phospha-adamantyl group, and, $X^1$ and $X^2$ together with $Q^2$ to which they are attached form a 2-phospha-adamantyl group;
 A and B are the same and represent —$CH_2$— or A is —$CH_2$— and B is not present so that the phosphorus is joined directly to the group R;
 $Q^1$ and $Q^2$ both represent phosphorus linked to the R group at ring positions 1 and 2;
 R represents ferrocene or benzene-1,2-diyl.

(7) $X^1$, $X^2$, $X^3$ and $X^4$ represent adamantyl;
 A and B are the same and represent —$CH_2$— or A is —$CH_2$— and B is not present so that the phosphorus is joined directly to the group R;
 $Q^1$ and $Q^2$ both represent phosphorus linked to the R group at ring positions 1 and 2;
 R represents ferrocene or benzene-1,2-diyl.

Preferably, in the compound of formula II, A and/or B each independently represents $C_1$ to $C_6$ alkylene which is optionally substituted as defined herein, for example with alkyl groups. Preferably, the lower alkylene groups which A and/or B represent are non-substituted. Particularly preferred alkylenes which A and B may independently represent are —$CH_2$— or —$C_2H_4$—. Most preferably, each of A and B represent the same alkylene as defined herein, particularly —$CH_2$— or A represents —$CH_2$— and B is not present or vice versa Still further preferred compounds of formulas I-II include those wherein:
$R^1$ to $R^{12}$ are alkyl and are the same and preferably, each represents $C_1$ to $C_6$ alkyl, particularly methyl.

Especially preferred specific compounds of formulas I-II include those wherein:
each $R^1$ to $R^{12}$ is the same and represents methyl;
A and B are the same and represent —$CH_2$—;
R represents benzene-1,2-diyl, ferrocene-1,2-diyl, 4-t-butyl-benzene-1,2-diyl, 4(trimethylsilyl)-benzene-1,2-diyl.

The adamantyl, congressyl, norbornyl or 1-norborndienyl group may optionally comprise, besides hydrogen atoms, one or more substituents selected from alkyl, —$OR^{19}$, —$OC(O)R^{20}$, halo, nitro, —$C(O)R^{21}$, —$C(O)OR^{22}$, cyano, aryl, —$N(R^{23})R^{24}$, —$C(O)N(R^{25})R^{26}$, —$C(S)N(R^{27})R^{28}$, —$SR^{29}$, —$C(O)SR^{30}$, —$CF_3$, —$P(R^{56})R^{57}$, —$PO(R^{58})(R^{59})$, —$PO_3H_2$, —$PO(OR^{60})(OR^{61})$, or —$SO_3R^{62}$, wherein $R^{19}$-$R^{30}$, alkyl, halo, cyano and aryl are as defined herein and $R^{56}$ to $R^{62}$ each independently represent hydrogen, alkyl, aryl or Het.

Suitably, when the adamantyl, congressyl, norbornyl or 1-norborndienyl group is substituted with one or more substituents as defined above, highly preferred substituents include unsubstituted $C_1$ to $C_8$ alkyl, —$OR^{19}$, —$OC(O)R^{20}$, phenyl, —$C(O)OR^{22}$, fluoro, —$SO_3H$, —$N(R^{23})R^{24}$, —$P(R^{56})R^{57}$, —$C(O)N(R^{25})R^{26}$ and —$PO(R^{58})(R^{59})$, —$CF_3$, wherein $R^{19}$-$R^{26}$ are as defined herein, $R^{56}$ to $R^{59}$ each independently represent unsubstituted $C_1$-$C_8$ alkyl or phenyl. In a particularly preferred embodiment the substituents are $C_1$ to $C_8$ alkyl, more preferably, methyl such as found in 1,3 dimethyl adamantyl.

Suitably, the adamantyl, congressyl, norbornyl or 1-norborndienyl group may comprise, besides hydrogen atoms, up to 10 substituents as defined above, preferably up to 5 substituents as defined above, more preferably up to 3 substituents as defined above. Suitably, when the adamantyl, congressyl, norbornyl or 1-norborndienyl group comprises, besides hydrogen atoms, one or more substituents as defined herein, preferably each substituent is identical. Preferred substituents are unsubstituted $C_1$-$C_8$ alkyl and trifluoromethyl, particularly unsubstituted $C_1$-$C_8$ alkyl such as methyl. A highly preferred adamantyl, congressyl, norbornyl or 1-norborndienyl group comprises hydrogen atoms only i.e. the adamantyl congressyl, norbornyl or 1-norborndienyl group is not substituted.

Preferably, when more than one adamantyl, congressyl, norbornyl or 1-norborndienyl group is present in a compound of formulas I-II, each such group is identical.

Preferably, the bidentate ligand is a bidentate phosphine, arsine or stibine ligand, preferably, a bidentate phosphine ligand. Particularly preferred is the bidentate phosphine ligand 1,2-bis(di-t-butylphophino)o-xylene.

DEFINITIONS

The term "lower alkylene" which A and B represent in a compound of formulas I-II, when used herein, includes $C_0$-$C_{10}$ or $C_1$ to $C_{10}$ groups which, in the latter case, can be bonded at two places on the group to thereby connect the group $Q^1$ or $Q^2$ to the R group, and, in the latter case, is otherwise defined in the same way as "alkyl" below. Nevertheless, in the latter case, methylene is most preferred. In the former case, by $C_0$ is meant that the group $Q^1$ or $Q^2$ is connected directly to the R group and there is no $C_1$-$C_{10}$ lower alkylene group and in this case only one of A and B is a $C_1$-$C_{10}$ lower alkylene. In any case, when one of the groups A or B is $C_0$ then the other group cannot be $C_0$ and must be a $C_1$-$C_{10}$ group as defined herein and, therefore, at least one of A and B is a $C_1$-$C_{10}$ "lower alkylene" group so that the term "optional" should be understood accordingly.

The term "alkyl" when used herein, means $C_1$ to $C_{10}$ alkyl and includes methyl, ethyl, ethenyl, propyl, propenyl butyl, butenyl, pentyl, pentenyl, hexyl, hexenyl and heptyl groups. Unless otherwise specified, alkyl groups may, when there is a sufficient number of carbon atoms, be linear or branched (particularly preferred branched groups include t-butyl and isopropyl), be saturated or unsaturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, unsubstituted or substituted aryl, or unsubstituted or substituted Het and/or be interrupted by one or more (preferably less than 4) oxygen, sulphur, silicon atoms, or by silano or dialkylsilcon groups, or mixtures thereof.

$R^1$ to $R^{12}$ and $R^{13}$-$R^{18}$ each independently represent alkyl, aryl, or Het unless $X^1$ or $X^2$ is joined to the $Q^2$ atom via a non tertiary carbon in which case they can each also represent hydrogen.

$R^{19}$ to $R^{30}$ herein each independently represent hydrogen, halo, unsubstituted or substituted aryl or unsubstituted or substituted alkyl, or, in the case of $R^{21}$, additionally, halo, nitro, cyano, thio and amino. Preferably, $R^{19}$ to $R^{30}$ represents hydrogen, unsubstituted $C_1$-$C_8$ alkyl or phenyl, more preferably, hydrogen or unsubstituted $C_1$-$C_8$ alkyl.

The term "Ar" or "aryl" when used herein, includes five-to-ten-membered, preferably five to eight membered, carbocyclic aromatic or pseudo aromatic groups, such as phenyl, cyclopentadienyl and indenyl anions and naphthyl, which groups may be unsubstituted or as one option substituted with one or more substituents selected from unsubstituted or substituted aryl, alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$ or $C(S)NR^{27}R^{28}$ wherein $R^{19}$ to $R^{30}$ are as defined herein.

The term "alkenyl" when used herein, means $C_2$ to $C_{10}$ alkenyl and includes ethenyl, propenyl, butenyl, pentenyl, and hexenyl groups. Unless otherwise specified, alkenyl groups may, when there is a sufficient number of carbon atoms, be linear or branched, be saturated or unsaturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, unsubstituted or substituted aryl, or unsubstituted or substituted Het, wherein $R^{19}$ to $R^{30}$ are defined herein and/or be interrupted by one or more (preferably less than 4) oxygen, sulphur, silicon atoms, or by silano or dialkylsilcon groups, or mixtures thereof.

The term "alkynyl" when used herein, means $C_2$ to $C_{10}$ alkynyl and includes ethynyl, propynyl, butynyl, pentynyl, and hexynyl groups. Unless otherwise specified, alkynyl groups may, when there is a sufficient number of carbon atoms, be linear or branched, be saturated or unsaturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, unsubstituted or substituted aryl, or unsubstituted or substituted Het, wherein $R^{19}$ to $R^{30}$ are defined herein and/or be interrupted by one or more (preferably less than 4) oxygen, sulphur, silicon atoms, or by silano or dialkylsilcon groups, or mixtures thereof.

The terms "alkyl", "aralkyl", "alkaryl", "arylenealkyl" or the like should, in the absence of information to the contrary, be taken to be in accordance with the above definition of "alkyl" as far as the alkyl or alk portion of the group is concerned.

The above Ar or aryl groups may be attached by one or more covalent bonds but references to "arylene" or "arylenealkyl" or the like herein should be understood as two covalent bond attachment but otherwise be defined as Ar or aryl above as far as the arylene portion of the group is concerned. References to "alkaryl", "aralkyl" or the like should be taken as references to Ar or aryl above as far as the Ar or aryl portion of the group is concerned.

Halo groups with which the above-mentioned groups may be substituted or terminated include fluoro, chloro, bromo and iodo.

The term "Het", when used herein, includes four- to twelve-membered, preferably four- to ten-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, alkyl (which alkyl group may itself be unsubstituted or substituted or terminated as defined herein) —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)$ $SR^{30}$ or —$C(S)N(R^{27})R^{28}$ wherein $R^{19}$ to $R^{30}$ are as defined herein The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

The term hetero as mentioned herein means nitrogen, oxygen, sulfur or mixtures thereof.

The catalyst compounds of the present invention may act as a "heterogeneous" catalyst or a "homogeneous" catalyst, preferably, a homogenous catalyst.

By the term "homogeneous" catalyst we mean a catalyst, i.e. a compound of the invention, which is not supported but is simply admixed or formed in-situ with the reactants of the carbonylation reaction, preferably in a suitable solvent as described herein.

By the term "heterogeneous" catalyst we mean a catalyst, i.e. the compound of the invention, which is carried on a support.

Where a compound of a formula herein (e.g. formulas I-II) contains an alkenyl group or a cycloalkyl moiety as defined, cis (E) and trans (Z) isomerism may also occur. The present invention includes the individual stereoisomers of the compounds of any of the formulas defined herein and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound one of the formulas or a suitable salt or derivative thereof. An individual enantiomer of a compound of one of the formulas may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

BRIEF DESCRIPTION OF THE DRAWINGS

The invention will now be described and illustrated by way of the following non-limiting examples and comparative examples wherein:—

Referring to FIG. 1, a continuous process for the reaction of purified streams of carbon monoxide, ethylene and methanol in the liquid phase, in the presence of a catalyst system, to generate the desired product, methyl propanoate is shown. A reactor tank 2 accommodates a liquid phase 4 and a gas phase 6. The liquid phase comprises methanol, methyl propanoate (MEP), dissolved process gas and catalyst components. The liquid phase 6 is stirred by means of a pair of mixing blades 8,10 located below the liquid phase surface in axially spaced relationship on drive shaft 12 driven by motor 14. A typical input gas stream 16 of 60% ethylene, 20% carbon monoxide and 20% of inert gases enters the reactor tank 2 near the base of the reactor tank side wall 18 and below the level of the liquid phase in the tank 2. The 20% of inert gases are typically made up of ethane 8%, methane 4%, carbon dioxide 0.4%, with nitrogen and argon making up the balance of 7.6%. The level and composition of the inerts will vary depending on the impurities present in the feed gas and guard bed efficiencies.

Figure 1:
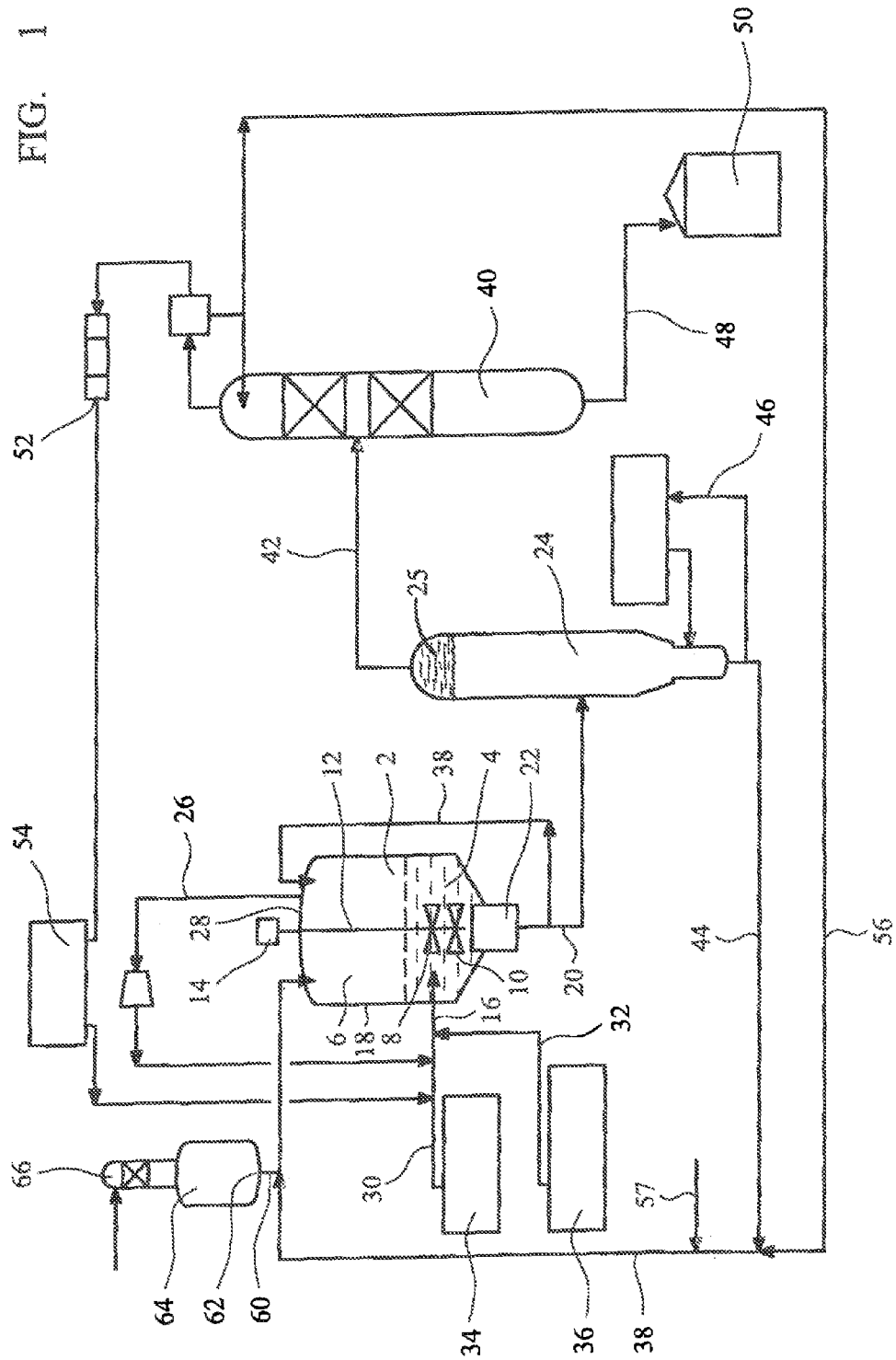
FIG. 1 is a schematic view of the process of the present invention.

The gas entering into the reactor vessel at the base passes up through the reaction mixture continuously and is dispersed by the agitator mixing blades 8,10 into fine bubbles. In this way the ethylene and carbon monoxide were dissolved in the reaction mix. The input gas stream 16 comprises an ethylene feed stream 30 and a carbon monoxide feed stream 32 which each proceed from their source (not shown) to the input gas stream, each via a respective guard bed 34, 36. The reactor tank 2 has a liquid phase exit pipe 20 located in the base wall 22 thereof to facilitate transport of the impure methyl propionate product stream to the flash column 24 and a gas phase exit pipe 26 located in the top wall 28 of the reactor 2 to facilitate transport of the headspace gas back to the input feed stream.

The product stream is fed for separation to a single stage 'flash' type distillation column 24 where the bulk of the MEP and methanol is flashed overhead along with a small portion of the sulphonic acid and its ester and directed to the purification column 40 via flash column overhead conduit 42. The heavy fraction which remained as liquid after being passed into the flash column contains the catalyst components and is recycled back into the reactor 2 via an exit pipe 44 located in the base of the flash column 24. Some of the heavy fraction may be cycled through a catalyst concentration loop 46 and back into the base of the flash column until it has reached the desired concentration or in order to avoid return of too much catalyst back to the reactor 2.

If the methyl propanoate product is required free of methanol, a second distillation column is needed. The methyl propionate flash column overhead stream is therefore fed into purification column 40 where the pure methyl propionate and the sulphonic acid or ester carry over is removed from the base thereof as the heavy fraction and fed via purification column base exit pipe 48 to the methyl propionate product tank 50. This material has been analysed after concentration for methyl methane sulphonate by GC and has been shown to contain this compound. The sulphur selectively removed from the flash column is a heavy in the MeP purification column A low boiling mixture of methanol and methyl propanoate is generated as the light product, and is removed continuously from the top of the MeP purification column. The liquid portion of the lighter fraction removed from the purification column 40 containing MeP and methanol may be recycled to the reactor 2.

The acid in the purified methyl propionate product may be simply neutralised by the addition of a stoichiometric amount of base. However, it is generally preferred to add an excess of base. Typically, the base is an alkali or alkaline earth metal hydroxide, more typically, sodium hydroxide is used.

In one embodiment, the sodium hydroxide is conveniently dissolved in formalin used in the catalytic conversion of methyl propionate to methyl methacrylate with formaldehyde. By introducing the sodium hydroxide into the formalin it is more easily dissolved due to the presence of methanol and water in the formalin. Contact of the formalin with the methyl propionate leads to neutralisation of the acid in the methyl propionate stream. By recycling of the unreacted methyl propionate stream acid free methyl propionate may be recycled into the conversion reaction with formalin.

For the purpose of recycling, the purification column recycle pipe 56 is connected with the flash column exit pipe 44. The combined recycle pipe is also connected to the incoming fresh catalyst feed pipe 57 to form a second liquid input pipe 58 for the reactor 2.

The reaction in reactor vessel 2 was carried out at 100° C. and at between 9 and 15 barg pressure.

The flash column 24 has been adapted to include packing 25 at the upper end thereof. The packing is arranged as structured packing and occupies just less than a quarter of the flash column. The packing is structured packing consisting of a bed of Sulzer Mellapak type 202Y situated at the top of the column. The effect of the packing is to give approximately two further equilibrium separation stages.

The catalyst system was made up as follows. Into a 15 m³ catalyst make-up tank blanketed under nitrogen is added 11600 liters of methyl propanoate and 117 liters of methanol. This material is sparged with nitrogen for 3 hours to ensure that it is thoroughly deoxygenated. To this solution is added 5.1 Kg of palladium dba (a mixture of tris(dibenzylideneacetone)dipalladium ($Pd_2(dba)_3$) and tris(dibenzylideneacetone)palladium ($Pd(dba)_3$) Heraeus-Pd assay 19.60% Pd (equivalent to 1.0 Kg of Pd metal) and 23.35 Kg of a 20% w/w solution of 1,2-bis(di-tert-butylphosphinomethyl)benzene in MeP. This equates to 9.40 moles of palladium and 11.85 moles of phosphine ligand, a ratio of palladium:phosphine of 1:1.26. The palladium salt and phosphine ligand are allowed to complex for 12 hours before the addition of 13.9 liters of a 70% w/w solution of methanesulphonic acid in water (133.53 moles of MSA). This results in a mole ratio of palladium:methanesulphonic acid of 1:14.2. This completes the preparation of the catalyst which is now ready for use and is fed at a low but continuous flow-rate directly through the fresh catalyst feed pipe 48 into Reactor 2. The palladium concentration of the catalyst solution is approximately 93 ppm Pd as calculated from the values above. The MW of palladium used for calculation of palladium feed rate is 106.4 Daltons. The palladium catalyst feed at this concentration generally results in a Pd concentration in the reactor of between 25-40 ppm. The total amount of methanesulphonic acid (MSA) fed to the process can be calculated based on the number of total catalyst batches fed to the process. The actual MSA levels present can be calculated by titration of the reactor and flash column solutions. The MSA level is calculated by subtracting the propionic acid (PA) value (determined by Gas Chromatography) from the total acid value determined by acid titration. No acids other than MSA and PA are present in the system During the above continuous operation, the palladium in the catalyst decomposes at a slow but steady rate, and is replaced by adding fresh catalyst made up as above.

After start up of the continuous reactor unit, when the desired rate of generation of methyl propanoate product had been achieved, a process of gradual reduction of the feed rates of the catalyst components was undertaken.

In order to sustain the rate of generation of methyl propanoate, it was found necessary to continuously replace the palladium and ligand catalyst component which were lost to decomposition with fresh palladium and ligand at a rate which balanced the rate of loss. However, the catalyst component also includes acid which is necessary to activate the palladium and the acid does not decompose and can therefore build up in the reactor.

Examples

Preparation of Methyl Propanoate from Ethylene, Carbon Monoxide and Methanol

Figure 2:
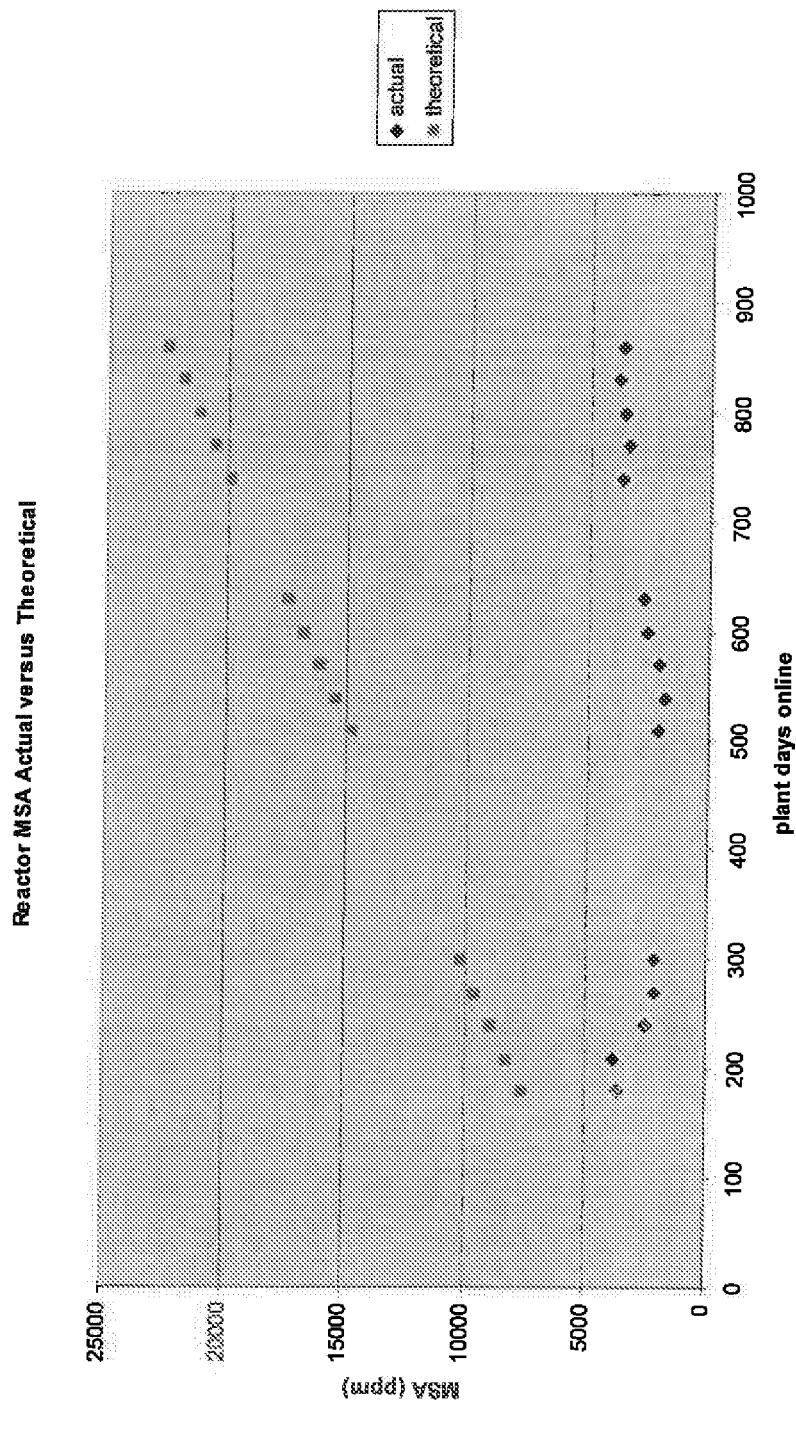
FIG. 2 is a plot of actual reactor acid versus theoretical reactor acid.
Figure 3:
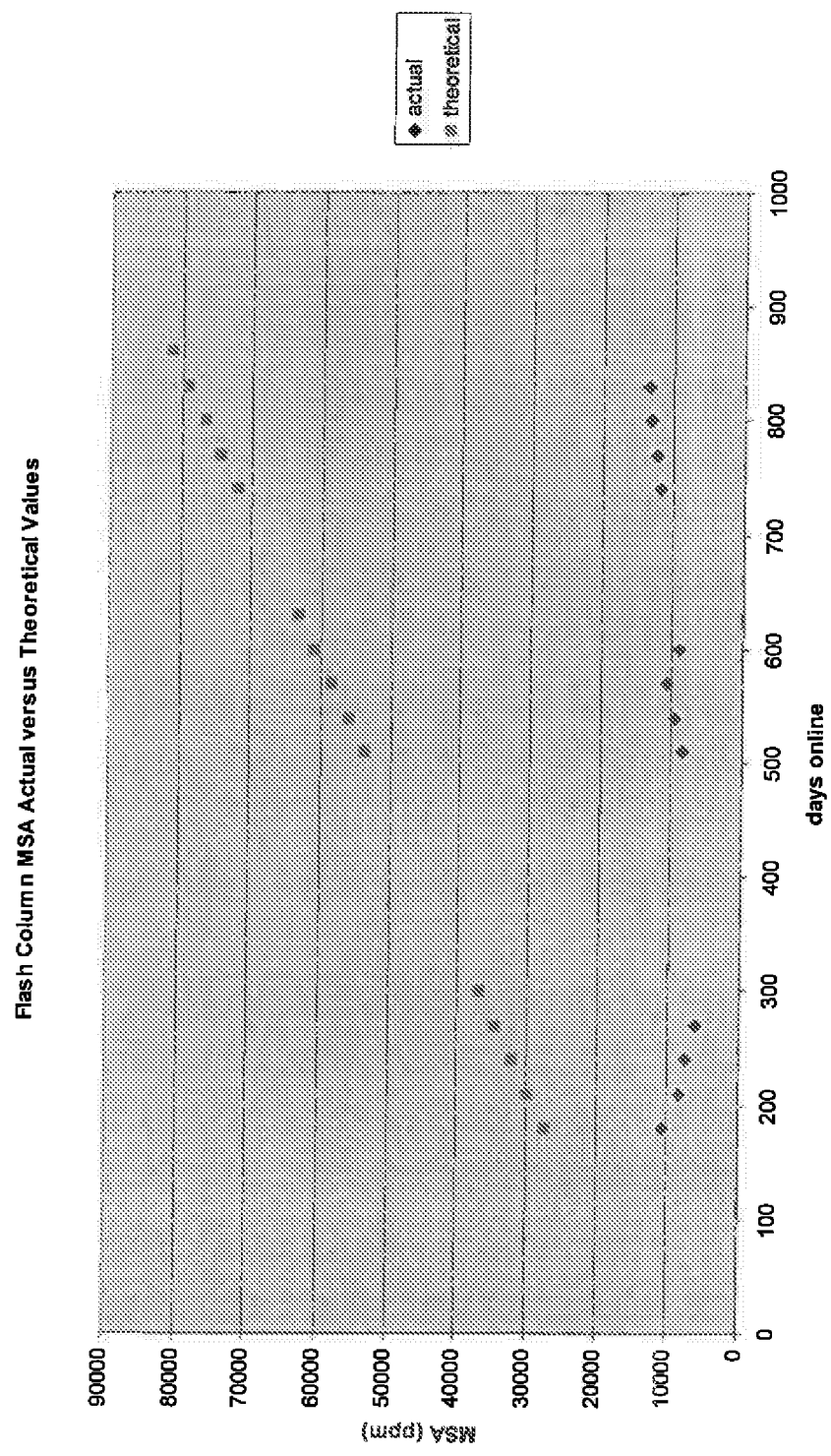
FIG. 3 is a plot of actual flash column acid versus theoretical acid.

Relevant acid analysis of the liquid phase outlet of the reactor, liquid phase of the flash column and product stream are shown in Table 1. The comparison between actual reactor and flash column MSA values and theoretical values obtained if no acid were removed from the process are shown in FIGS. 2 and 3.

TABLE 1

| Days Online | Reactor MSA Actual (ppm) | Reactor MSA Theory (ppm) | Flash Column Liquid MSA Actual (ppm) | Flash Column Liquid MSA Theory (ppm) |
| --- | --- | --- | --- | --- |
| 180 | 3631 | 7531 | | 27259 |
| 210 | 3780 | 8191 | 10772 | 29647 |
| 240 | 2493 | 8851 | 8499 | 32036 |
| 270 | 2134 | 9511 | 7480 | 34425 |
| 300 | 2194 | 10171 | 6256 | 36814 |
| 510 | 2080 | 14791 | 9012 | 53536 |
| 540 | 1801 | 15451 | 8483 | 55925 |
| 570 | 2096 | 16111 | 9648 | 58314 |
| 600 | 2583 | 16771 | 10516 | 60703 |
| 630 | 2710 | 17431 | 8930 | 63092 |
| 740 | 3670 | 19851 | 10729 | 71851 |
| 770 | 3396 | 20511 | 11642 | 74240 |
| 800 | 3552 | 21171 | 12427 | 76629 |
| 830 | 3790 | 21831 | 13282 | 79018 |
| 860 | 3680 | 22491 | 13582 | 81407 |

Theoretical acid values are based on the addition of one catalyst batch every fourteen days and an average flash:reactor concentration factor of 3.62. It can be seen from FIGS. 2 and 3 that the flash column of the invention surprisingly prevents acid build up in the reactor.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A continuous process for the production of an alkyl ester product comprising the steps of carbonylating ethylene with carbon monoxide in the presence of C1-6 alkanol co-reactant to form the said alkyl ester product, wherein the carbonylation takes place in the presence of a catalyst system comprising;
   a. a bidentate ligand,
   b. a catalytic metal selected from a group 8, 9 or 10 metal or a compound thereof, and
   c. a sulphonic acid capable of forming an acid alkyl ester with the C1-6 alkanol, the process including the step of separating the formed alkyl ester product from a carbonylated crude product stream by treatment that vaporizes the alkyl ester product in a single stage flash distillation column and provide a purified alkyl ester product stream separated from the said bidentate ligand and catalytic metal, wherein the said distillation column includes further separation means effective to provide further separation of the product while reducing acid build-up in a reactor.

2. The process of claim 1, wherein the further separation means is packing in or associated with the upper part of the flash distillation column and/or is provided by trays.

3. The process of claim 2, wherein the packing is structured or random packing.

4. The process of claim 2, wherein the packing provides between 0.01 and 5 further theoretical plates for separation.

5. The process of claim 2, wherein the packing occupies between 5 and 40% of the column.

6. The process of claim 1, wherein an amount of reflux is introduced into the flash distillation column.

7. The process of claim 6, wherein the reflux component is a separate stream of the alkyl ester product of the reaction or a mixture thereof.

8. The process of claim 7, wherein the alkyl ester product is vaporised from within the crude product stream by effective heat treatment in the flash distillation column at a suitable temperature and pressure effective to vaporise the product and/or its azeotrope with other components present.

9. The process of claim 1, wherein the purified alkyl ester product stream is subsequently subjected to a sulphonic acid treatment step effective to separate the said acid from or neutralise the said acid in the said purified alkyl ester product stream.

10. The process of claim 9, wherein the sulphonic acid treatment step is either carried out with base to at least partly neutralise the acid in the said purified product stream or is carried out by suitable heat and/or pressure treatment effective to preferentially vaporise the alkyl ester product from the purified stream such as by distillation thus leaving the acid and its ester as a heavy fraction.

11. The process of claim 9, wherein the sulphonic acid has a pKa of less than 6 when measured in dilute aqueous solution at 25° C.

12. The process of claim 9, wherein the sulphonic acid is selected from the group consisting of methane sulphonic acid, chlorosulphonic acid, fluorosulphonic acid, trifluoromethane sulphonic acid, benzene sulphonic acid, naphthalene sulphonic acid, toluene sulphonic acid (e.g. p-toluene sulphonic acid), t-butyl sulphonic acid, 2-hydroxypropane sulphonic acid, C2-C12 alkanesulphonic acid, camphor sulphonic acid or 1 and 2-adamantanesulphonic acid.

13. The process of claim 1, wherein the bidentate ligand is a bidentate ligand of general formula (I)

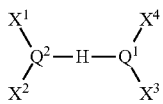

wherein:
H is a bivalent organic bridging group with 1-6 atoms in the bridge;
X1, X2, X3 and X4 independently represent univalent radicals of up to 30 atoms, optionally having at least one tertiary carbon atom via which the group is joined to the Q1 or Q2 atom, or X1 and X2 and/or X3 and X4 together form a bivalent radical of up to 40 atoms, optionally having at least two tertiary carbon atoms via which the radical is joined to the Q1 and/or Q2 atom; and
Q1 and Q2 each represent phosphorus, arsenic or antimony.

14. The process of claim 1, wherein the alkanol co-reactant is methanol, ethanol, propanol, iso-propanol, iso-butanol, t-butyl alcohol, phenol or n-butanol.

15. The process of claim 13, wherein the bidentate ligand is selected from 1,2-bis-(di-tert-butylphosphinomethyl)benzene, 1,2-bis-(di-tert-pentylphosphinomethyl)benzene, 1,2-bis-(di-tert-butylphosphinomethyl)naphthalene, 1,2 bis(di-adamantylphosphinomethyl)benzene, 1,2 bis(di-3,5-dimethyladamantylphosphinomethyl)benzene, 1,2 bis(di-5-tert-butyladamantylphosphinomethyl)benzene, 1,2 bis(1-adamantyl tert-butyl-phosphinomethyl)benzene, 1,2-bis-(2,2,6,6-tetramethyl-phospha-cyclohexan-4-one)-o-xylene, 1,2-bis-(2-(phospha-adamantyl))-o-xylene, 1-(diadamantylphosphinomethyl)-2-(di-tert-butylphosphinomethyl)benzene, 1-(di-tert-butylphosphinomethyl)-2-(dicongressylphosphinomethyl)benzene, 1-(di-tert-butylphosphino)-2-(phospha-adamantyl)o-xylene, 1-(diadamantylphosphino)-2-(phospha-adamantyl)o-xylene, 1-(di-tert-butylphosphino)-2-(P-(2,2,6,6-tetramethyl-phospha-cyclohexan-4-one)o-xylene, 142,2,6,6-tetramethyl-phospha-cyclohexan-4-one)-2-(phospha-adamantyl)o-xylene, 1-(di-tert-butylphosphinomethyl)-2-(di-tert-butylphosphino) benzene, 1-(phospha-adamantyl)-2-(phospha-adamantyl)methylbenzene, 1-(diadamantylphosphinomethyl)-2-(diadamantylphosphino)benzene, 1-(2-(P-(2,2,6,6-tetramethyl-phospha-cyclohexan-4-one))-benzyl)-2,2,6,6-tetramethyl-phospha-cyclohexan-4-one, 1-(di-tert-butylphosphinomethyl)-2-(phospha-adamantyl)benzene, 1-(di-tert-butylphosphinomethyl)-2-(diadamantylphosphino)benzene, 1-(di-tert-butylphosphinomethyl)-2-(P-(2,2,6,6-tetramethyl-phospha-cyclohexan-4-one)benzene, 1-(tert-butyl,adamantylphosphinomethyl)-2-(di-adamantylphosphinomethyl)benzene, 1-[(P-(2,2,6,6,-tetramethyl-phospha-cyclohexan-4-one)methyl)]-2-(phospha-adamantyl)benzene, 1,2-bis-(ditertbutylphosphinomethyl)ferrocene, 1,2,3-tris-(ditertbutylphosphinomethyl)ferrocene, 1,2-bis(1,3,5,7-tetramethyl-6,9,10-trioxa-2-phospha-adamantylmethyl)ferrocene, 1,2-bis-α,α-(P-(2,2,6,6-tetramethyl-phospha-cyclohexan-4-one))dimethylferrocene, and 1-(di-tert-butylphosphinomethyl)-2-(P-(2,2,6,6-tetramethyl-phospha-cyclohexan-4-one))ferrocene and 1,2-bis(1,3,5,7-tetramethyl-6,9,10-trioxa-2-phospha-adamantylmethyl) benzene; wherein "phospha-adamantyl" is selected from 2-phospha-1,3,5,7-tetramethyl-6,9,10-trioxadamantyl, 2-phospha-1,3,5-trimethyl-6,9,10 trioxadamantyl, 2-phospha-1,3,5,7-tetra(trifluoromethyl)-6,9,10-trioxadamantyl or 2-phospha-1,3,5-tri(trifluoromethyl)-6,9,10-trioxadamantyl, cis-1,2-bis(di-t-butylphosphinomethyl)-4,5-dimethyl cyclohexane; cis-1,2-bis(di-t-butylphosphinomethyl)-5-methylcyclopentane; cis-1,2-bis(2-phosphinomethyl-1,3,5,7-tetramethyl-6,9,10-trioxa-adamantyl)-4,5-dimethylcyclohexane; cis-1,2-bis(2-phosphinomethyl-1,3,5,7-tetramethyl-6,9,10-trioxa-adamantyl) 5-methylcyclopentane; cis-1,2-bis(di-adamantylphosphinomethyl)-4,5 dimethylcyclohexane; cis-1,2-bis(di-adamantylphosphinomethyl)-5-methyl cyclopentane; cis-1-(P,P adamantyl,t-butyl phosphinomethyl)-2-(di-t-butylphosphinomethyl)-4,5-dimethylcyclohexane; cis-1-(P,P adamantyl,t-butyl phosphinomethyl)-2-(di-t-butylphosphinomethyl)-5-methylcyclopentane; cis-1-(2-phosphinomethyl-1,3,5,7-tetramethyl-6,9,10-trioxa-adamantyl)-2-(di-t-butylphosphinomethyl)4,5-dimethylcyclohexane; cis-1-(2-phosphinomethyl-1,3,5,7-tetramethyl-6,9,10-trioxa-adamantyl)-2-(di-t-butylphosphinomethyl)-5-methyl cyclopentane; cis-1-(2-phosphinomethyl-1,3,5,7-tetramethyl-6,9,10-trioxa-adamantyl)-2-(diadamantylphosphinomethyl)-5-methyl cyclohexane; cis-1-(2-phosphinomethyl-1,3,5,7-tetramethyl-6,9,10-trioxa-adamantyl)-2-

(diadamantylphosphinomethyl)-5-methyl cyclopentane; cis-1-(2-phosphinomethyl-1,3,5,7-tetramethyl-6,9,10-trioxa-adamantyl)-2-(diadamantylphosphinomethyl)cyclobutane; cis-1-(di-t-butylphosphinomethyl)-2-(diadamantylphosphinomethyl)-4,5-dimethyl cyclohexane; cis-1-(di-t-butylphosphinomethyl)-2-(diadamantylphosphinomethyl)-5-methyl cyclopentane; cis-1,2-bis(2-phosphinomethyl-1,3,5-trimethyl-6,9,10-trioxatricyclo-{3.3.1.1[3.7]}decyl)-4,5-dimethyl cyclohexane; cis-1,2-bis(2-phosphinomethyl-1,3,5-trimethyl-6,9,10-trioxatricyclo-{3.3.1.1[3.7]}decyl)-5-methyl cyclopentane; cis-1-(2-phosphinomethyl-1,3,5-trimethyl-6,9,10-trioxatricyclo-{3.3.1.1[3.7]}decyl)-2-(di-t-butylphosphinomethyl)-4,5-dimethyl cyclohexane; cis-1-(2-phosphinomethyl-1,3,5-trimethyl-6,9,10-trioxatricyclo-{3.3.1.1[3.7]}decyl)-2-(di-t-butylphosphinomethyl)-5-methyl cyclopentane; cis-1-(2-phosphinomethyl-1,3,5-trimethyl-6,9,10-trioxatricyclo-{3.3.1.1[3.7]}decyl)-2-(diadamantylphosphinomethyl)-4,5-dimethyl cyclohexane; cis-1-(2-phosphinomethyl-1,3,5-trimethyl-6,9,10-trioxatricyclo-{3.3.1.1[3.7]}decyl)-2-(diadamantylphosphinomethyl)-5-methyl cyclopentane; cis-1,2-bis-perfluoro(2-phosphinomethyl-1,3,5,7-tetramethyl-6,9,10-trioxatricyclo{3.3.1.1[3.7]}-decyl)-4,5-dimethyl cyclohexane; cis-1,2-bis-perfluoro(2-phosphinomethyl-1,3,5,7-tetramethyl-6,9,10-trioxatricyclo{3.3.1.1[3.7]}decyl)-5-methyl cyclopentane; cis-1,2-bis-(2-phosphinomethyl-1,3,5,7-tetra(trifluoro-methyl)-6,9,10-trioxatricyclo{3.3.1.1[3.7]}decyl)-4,5-dimethyl cyclohexane; cis-1,2-bis-(2-phosphinomethyl-1,3,5,7-tetra(trifluoro-methyl)-6,9,10-trioxatricyclo{3.3.1.1[3.7]}decyl)-5-methyl cyclopentane; cis-1-(2-phosphino-1,3,5,7-tetramethyl-6,9,10-trioxa-adamantyl)-2-(di-t-butylphosphinomethyl)-4,5-dimethylcyclohexane; cis-1-(2-phosphinomethyl-1,3,5,7-tetramethyl-6,9,10-trioxa-adamantyl)-2-(2-phosphino-1,3,5,7-tetramethyl-6,9,10-trioxa-adamantyl)-4,5-dimethyl cyclohexane; cis-1-(di-t-butylphosphino)-2-(di-t-butylphosphinomethyl)-4,5-dimethyl cyclohexane; cis-1-(di-adamantylphosphino)-2-(di-t-butylphosphinomethyl)-4,5-dimethyl cyclohexane; cis-1-(di-adamantylphosphino)-2-(di-adamantylphosphinomethyl)-4,5-dimethyl cyclohexane; cis-1-(2-phosphino-1,3,5,7-tetramethyl-6,9,10-trioxa-adamantyl)-2-(di-adamantylphosphinomethyl)-4,5-dimethyl cyclohexane; cis-1-(P-(2,2,6,6-tetramethyl-phospha-cyclohexan-4-one))-2-(di-t-butylphosphinomethyl)-4,5-dimethyl cyclohexane; 1-[4,5-dimethyl-2-P-(2,2,6,6-tetramethyl-phospha-cyclohexan-4-one)-[1S,2R]cyclohexylmethyl]-P-2,2,6,6-tetramethyl-phospha-cyclohexan-4-one, cis-1,2-bis(di-t-butylphosphinomethyl)cyclohexane; cis-1,2-bis(di-t-butylphosphinomethyl)cyclopentane; cis-1,2-bis(di-t-butylphosphinomethyl)cyclobutane; cis-1,2-bis(2-phosphinomethyl-1,3,5,7-tetramethyl-6,9,10-trioxa-adamantyl)cyclohexane; cis-1,2-bis(2-phosphinomethyl-1,3,5,7-tetramethyl-6,9,10-trioxa-adamantyl)cyclopentane; cis-1,2-bis(2-phosphinomethyl-1,3,5,7-tetramethyl-6,9,10-trioxa-adamantyl)cyclobutane; cis-1,2-bis(di-adamantylphosphinomethyl)cyclohexane; cis-1,2-bis(di-adamantylphosphinomethyl)cyclopentane; cis-1,2-bis(di-adamantylphosphinomethyl)cyclobutane; cis-1,2-bis (P-(2,2,6,6-tetramethyl-phospha-cyclohexan-4-one)) dimethylcyclohexane, cis-1-(P,P-adamantyl,t-butyl-phosphinomethyl)-2-(di-t-butylphosphinomethyl)cyclohexane; cis-1-(2-phosphino-1,3,5,7-tetramethyl-6,9,10-trioxa-adamantyl)-2-(di-tbutylphosphinomethyl)cyclohexane; cis-1-(2-phosphinomethyl-1,3,5,7-tetramethyl-6,9,10-trioxa-adamantyl)-2-(2-phosphino-1,3,5,7-tetramethyl-6,9,10-trioxa-adamantyl)cyclohexane; cis-1-(di-t-butylphosphino)-2-(di-t-butylphosphinomethyl)cyclohexane; cis-1-(di-adamantylphosphino)-2-(di-t-butylphosphinomethyl)cyclohexane; cis-1-(di-adamantylphosphino)-2-(di-adamantylphosphinomethyl)cyclohexane; cis-1-(2-phosphino-1,3,5,7-tetramethyl-6,9,10-trioxa-adamantyl)-2-(di-adamantylphosphinomethyl)cyclohexane; cis-1-(P-(2,2,6,6-tetramethyl-phospha-cyclohexan-4-one))-2-(di-t-butylphosphinomethyl)cyclohexane; cis-1-(P-(2,2,6,6-tetramethyl-phospha-cyclohexan-4-one))-2-(P-(2,2,6,6-tetramethyl-phospha-cyclohexan-4-one))methylcyclohexane; cis-1-(P,P-adamantyl,t-butyl-phosphinomethyl)-2-(di-t-butylphosphinomethyl)cyclopentane; cis-1-(P,P-adamantyl,t-butyl-phosphinomethyl)-2-(di-t-butylphosphinomethyl)cyclobutane; cis-1-(2-phosphinomethyl-1,3,5,7-tetramethyl-6,9,10-trioxa-adamantyl)-2-(di-t-butylphosphinomethyl)cyclohexane; cis-1-(2-phosphinomethyl-1,3,5,7-tetramethyl-6,9,10-trioxa-adamantyl)-2-(di-t-butylphosphinomethyl)cyclopentane; cis-1-(2-phosphinomethyl-1,3,5,7-tetramethyl-6,9,10-trioxa-adamantyl)-2-(di-t-butylphosphinomethyl)cyclobutane; cis-1-(2-phosphinomethyl-1,3,5,7-tetramethyl-6,9,10-trioxa-adamantyl)-2-(diadamantylphosphinomethyl)cyclohexane; cis-1-(2-phosphinomethyl-1,3,5,7-tetramethyl-6,9,10-trioxa-adamantyl)-2-(diadamantylphosphinomethyl)cyclopentane; cis-1-(2-phosphinomethyl-1,3,5,7-tetramethyl-6,9,10-trioxa-adamantyl)-2-(diadamantylphosphinomethyl)cyclobutane; cis-1-(di-t-butylphosphinomethyl)-2-(diadamantylphosphinomethyl)cyclohexane; cis-1-(di-t-butylphosphinomethyl)-2-(diadamantylphosphinomethyl)cyclopentane; cis-1-(di-t-butylphosphinomethyl)-2-(diadamantylphosphinomethyl)cyclobutane; cis-1,2-bis(2-phosphinomethyl-1,3,5-trimethyl-6,9,10-trioxatricyclo-{3.3.1.1[3.7]}decyl)cyclohexane; cis-1,2-bis(2-phosphinomethyl-1,3,5-trimethyl-6,9,10-trioxatricyclo-{3.3.1.1[3.7]}decyl)cyclopentane; cis-1,2-bis(2-phosphinomethyl-1,3,5-trimethyl-6,9,10-trioxatricyclo-{3.3.1.1[3.7]}decyl)cyclobutane; cis-1-(2-phosphinomethyl-1,3,5-trimethyl-6,9,10-trioxatricyclo-{3.3.1.1[3.7]}decyl)-2-(di-t-butylphosphinomethyl)cyclohexane; cis-1-(2-phosphinomethyl-1,3,5-trimethyl-6,9,10-trioxatricyclo-{3.3.1.1[3.7]}decyl)-2-(di-t-butylphosphinomethyl)cyclopentane; cis-1-(2-phosphinomethyl-1,3,5-trimethyl-6,9,10-trioxatricyclo-{3.3.1.1[3.7]}decyl)-2-(di-t-butylphosphinomethyl)cyclobutane; cis-1-(2-phosphinomethyl-1,3,5-trimethyl-6,9,10-trioxatricyclo-{3.3.1.1[3.7]}decyl)-2-(diadamantylphosphinomethyl)cyclohexane; cis-1-(2-phosphinomethyl-1,3,5-trimethyl-6,9,10-trioxatricyclo-{3.3.1.1[3.7]}decyl)-2-(diadamantylphosphinomethyl)cyclopentane; cis-1-(2-phosphinomethyl-1,3,5-trimethyl-6,9,10-trioxatricyclo-{3.3.1.1[3.7]}decyl)-2-(diadamantylphosphinomethyl)cyclobutane; cis-1,2-bis-perfluoro(2-phosphinomethyl-1,3,5,7-tetramethyl-6,9,10-trioxatricyclo{3.3.1.1[3.7]}-decyl)cyclohexane; cis-1,2-bis-perfluoro(2-phosphinomethyl-1,3,5,7-tetramethyl-6,9,10-trioxatricyclo{3.3.1.1[3.7]}decyl)cyclopentane; cis-1,2-bis-perfluoro(2-phosphinomethyl-1,3,5,7-tetramethyl-6,9,10-trioxatricyclo{3.3.1.1[3.7]}decyl)cyclobutane; cis-1,2-bis-(2-phosphinomethyl-1,3,5,7-tetra(trifluoro-methyl)-6,9,10-trioxatricyclo{3.3.1.1[3.7]}decyl)cyclohexane; cis-1,2-bis-(2-phosphinomethyl-1,3,5,7-tetra(trifluoro-methyl)-6,9,10-trioxatricyclo{3.3.1.1[3.7]}decyl)cyclopentane; and cis-1,2-bis-(2-phosphinomethyl-1,3,5,7-tetra(trifluoro-methyl)-6,9,10-trioxatricyclo{3.3.1.1[3.7]}decyl)cyclobutane, (2-exo, 3-exo)-bicyclo[2.2.1]heptane-2,3-bis(di-tert-butylphosphinomethyl) and (2-endo, 3-endo)-bicyclo[2.2.1]heptane-2,3- bis(di-tert-butylphosphinomethyl), 1,2-bis(di-t-butylphosphinomethyl)-4,5-diphenyl benzene; 1,2-bis(di-t-butylphosphinomethyl)-4-phenylbenzene; 1,2-bis(di-t-butylphosphinomethyl)-4,5-bis-(trimethylsilyl)benzene; 1,2-bis(di-t-butylphosphinomethyl)-4-(trimethylsilyl)benzene; 1,2-bis(2-phosphinomethyl-1,3,5,7-tetramethyl-6,9,10-trioxa-adamantyl)-4,5-diphenylbenzene; 1,2-bis(2-phosphinomethyl-1,3,5,7-tetramethyl-6,9,10-trioxa-adamantyl)-4-phenylbenzene; 1,2-bis(2-phosphinomethyl-1,3,5,7-tetramethyl-6,9,10-trioxa-adamantyl)-4,5-bis-(trimethylsilyl)benzene; 1,2-bis(2-phosphinomethyl-1,3,5,7-tetramethyl-6,9,10-trioxa-adamantyl)-4-(trimethylsilyl)benzene; 1,2-bis(di-adamantylphosphinomethyl)-4,5 diphenylbenzene; 1,2-bis(di-adamantylphosphinomethyl)-4-phenyl benzene; 1,2-bis(di-adamantylphosphinomethyl)-4,5 bis-(trimethylsilyl)benzene; 1,2-bis(di-adamantylphosphinomethyl)-4-(trimethylsilyl)benzene; 1-(P,P adamantyl,t-butyl phosphinomethyl)-2-(di-t-butylphosphinomethyl)-4,5-diphenylbenzene; 1-(P,P adamantyl,t-butyl phosphinomethyl)-2-(di-t-butylphosphinomethyl)-4-phenylbenzene; 1-(P,P adamantyl,t-butyl phosphinomethyl)-2-(di-t-butylphosphinomethyl)-4,5-bis-(trimethylsilyl)benzene; 1-(P,P adamantyl,t-butyl phosphinomethyl)-2-(di-t-butylphosphinomethyl)-4-(trimethylsilyl)benzene; 1-(2-phosphinomethyl-1,3,5,7-tetramethyl-6,9,10-trioxa-adamantyl)-2-(di-t-butylphosphinomethyl)4,5-diphenylbenzene; 1-(2-phosphinomethyl-1,3,5,7-tetramethyl-6,9,10-trioxa-adamantyl)-2-(di-t-butylphosphinomethyl)-4-phenyl benzene; 1-(2-phosphinomethyl-1,3,5,7-tetramethyl-6,9,10-trioxa-adamantyl)-2-(di-t-butylphosphinomethyl)4,5-bis-(trimethylsilyl)benzene; 1-(2-phosphinomethyl-1,3,5,7-tetramethyl-6,9,10-trioxa-adamantyl)-2-(di-t-butylphosphinomethyl)-4-(trimethylsilyl)benzene; 1-(2-phosphinomethyl-1,3,5,7-tetramethyl-6,9,10-trioxa-adamantyl)-2-(diadamantylphosphinomethyl)-4,5-diphenylbenzene; 1-(2-phosphinomethyl-1,3,5,7-tetramethyl-6,9,10-trioxa-adamantyl)-2-(diadamantylphosphinomethyl)-4-phenyl benzene; 1-(2-phosphinomethyl-1,3,5,7-tetramethyl-6,9,10-trioxa-adamantyl)-2-(diadamantylphosphinomethyl)-4,5-bis-(trimethylsilyl)benzene; 1-(2-phosphinomethyl-1,3,5,7-tetramethyl-6,9,10-trioxa-adamantyl)-2-(diadamantylphosphinomethyl)-4-(trimethylsilyl)benzene; 1-(di-t-butylphosphinomethyl)-2-(diadamantylphosphinomethyl)-4,5-diphenyl benzene; 1-(di-t-butylphosphinomethyl)-2-(diadamantylphosphinomethyl)-4-phenyl benzene; 1-(di-t-butylphosphinomethyl)-2-(diadamantylphosphinomethyl)-4,5-bis-(trimethylsilyl)benzene; 1-(di-t-butylphosphinomethyl)-2-(diadamantylphosphinomethyl)-4-(trimethylsilyl)benzene; 1,2-bis(2-phosphinomethyl-1,3,5-trimethyl-6,9,10-trioxatricyclo-{3.3.1.1[3.7]}decyl)-4,5-diphenyl benzene; 1,2-bis(2-phosphinomethyl-1,3,5-trimethyl-6,9,10-trioxatricyclo-{3.3.1.1[3.7]}decyl)-4-phenyl benzene; 1,2-bis(2-phosphinomethyl-1,3,5-trimethyl-6,9,10-trioxatricyclo-{3.3.1.1[3.7]}decyl)-4,5-bis-(trimethylsilyl)benzene; 1,2-bis(2-phosphinomethyl-1,3,5-trimethyl-6,9,10-trioxatricyclo-{3.3.1.1[3.7]}decyl)-4-(trimethylsilyl)benzene; 1-(2-phosphinomethyl-1,3,5-trimethyl-6,9,10-trioxatricyclo-{3.3.1.1[3.7]}decyl)-2-(di-t-butylphosphinomethyl)-4,5-diphenyl benzene; 1-(2-phosphinomethyl-1,3,5-trimethyl-6,9,10-trioxatricyclo-{3.3.1.1[3.7]}decyl)-2-(di-t-butylphosphinomethyl)-4-phenyl benzene; 1-(2-phosphinomethyl-1,3,5-trimethyl-6,9,10-trioxatricyclo-{3.3.1.1[3.7]}decyl)-2-(di-t-butylphosphinomethyl)-4,5-bis-(trimethylsilyl)benzene; 1-(2-phosphinomethyl-1,3,5-trimethyl-6,9,10-trioxatricyclo-{3.3.1.1[3.7]}decyl)-2-(di-t-butylphosphinomethyl)-4-(trimethylsilyl)benzene; 1-(2-phosphinomethyl-1,3,5-trimethyl-6,9,10-trioxatricyclo-{3.3.1.1[3.7]}decyl)-2-(diadamantylphosphinomethyl)-4,5-diphenyl benzene; 1-(2-phosphinomethyl-1,3,5-trimethyl-6,9,10-trioxatricyclo-{3.3.1.1[3.7]}decyl)-2-(diadamantylphosphinomethyl)-4-phenyl benzene; 1-(2-phosphinomethyl-1,3,5-trimethyl-6,9,10-trioxatricyclo-{3.3.1.1[3.7]}decyl)-2-(diadamantylphosphinomethyl)-4,5-bis-(trimethylsilyl)benzene; 1-(2-phosphinomethyl-1,3,5-trimethyl-6,9,10-trioxatricyclo-{3.3.1.1[3.7]}decyl)-2-(diadamantylphosphinomethyl)-4-(trimethylsilyl)benzene; 1,2-bis-perfluoro(2-phosphinomethyl-1,3,5,7-tetramethyl-6,9,10-trioxatricyclo{3.3.1.1[3.7]}-decyl)-4,5-diphenyl benzene; 1,2-bis-perfluoro(2-phosphinomethyl-1,3,5,7-tetramethyl-6,9,10-trioxatricyclo{3.3.1.1[3.7]}decyl)-4-phenyl benzene; 1,2-bis-perfluoro(2-phosphinomethyl-1,3,5,7-tetramethyl-6,9,10-trioxatricyclo{3.3.1.1[3.7]}-decyl)-4,5-bis-(trimethylsilyl)benzene; 1,2-bis-perfluoro(2-phosphinomethyl-1,3,5,7-tetramethyl-6,9,10-trioxatricyclo{3.3.1.1[3.7]}decyl)-4-(trimethylsilyl)benzene; 1,2-bis-(2-phosphinomethyl-1,3,5,7-tetra(trifluoro-methyl)-6,9,10-trioxatricyclo{3.3.1.1[3.7]}decyl)-4,5-diphenyl benzene; 1,2-bis-(2-phosphinomethyl-1,3,5,7-tetra(trifluoro-methyl)-6,9,10-trioxatricyclo{3.3.1.1[3.7]}decyl)-4-phenyl benzene; 1,2-bis-(2-phosphinomethyl-1,3,5,7-tetra(trifluoro-methyl)-6,9,10-trioxatricyclo{3.3.1.1[3.7]}decyl)-4,5-bis-(trimethylsilyl)benzene; 1,2-bis-(2-phosphinomethyl-1,3,5,7-tetra(trifluoro-methyl)-6,9,10-trioxatricyclo{3.3.1.1[3.7]}decyl)-4-(trimethylsilyl)benzene; 1,2-bis(di-t-butylphosphinomethyl)-4,5-di-(2'-phenylprop-2'-yl) benzene; 1,2-bis(di-t-butylphosphinomethyl)-4-(2'-phenylprop-2'-yl)benzene; 1,2-bis(di-t-butylphosphinomethyl)-4,5-di-t-butyl benzene; 1,2-bis(di-t-butylphosphinomethyl)-4-t-butylbenzene; 1,2-bis(2-phosphinomethyl-1,3,5,7-tetramethyl-6,9,10-trioxa-adamantyl)-4,5-di-(2'-phenylprop-2'-yl)benzene; 1,2-bis(2-phosphinomethyl-1,3,5,7-tetramethyl-6,9,10-trioxa-adamantyl)-4-(2'-phenylprop-2'-yl)benzene; 1,2-bis(2-phosphinomethyl-1,3,5,7-tetramethyl-6,9,10-trioxa-adamantyl)-4,5-(di-t-butyl)benzene; 1,2-bis(2-phosphinomethyl-1,3,5,7-tetramethyl-6,9,10-trioxa-adamantyl)-4-t-butylbenzene; 1,2-bis(di-adamantylphosphinomethyl)-4,5-di-(2'-phenylprop-2'-yl) benzene; 1,2-bis(di-adamantylphosphinomethyl)-4-(2'-phenylprop-2'-yl)benzene; 1,2-bis(di-adamantylphosphinomethyl)-4,5-(di-t-butyl)benzene; 1,2-bis(di-adamantylphosphinomethyl)-4-t-butyl benzene; 1-(P,P adamantyl,t-butyl phosphinomethyl)-2-(di-t-butylphosphinomethyl)-4,5-di-(2'-phenylprop-2'-yl)benzene; 1-(P,P adamantyl,t-butyl phosphinomethyl)-2-(di-t-butylphosphinomethyl)-4-(2'-phenylprop-2'-yl)benzene; 1-(P,P adamantyl,t-butyl phosphinomethyl)-2-(di-t-butylphosphinomethyl)-4,5-(di-t-butyl)benzene; 1-(P,P adamantyl,t-butyl phosphinomethyl)-2-(di-t-butylphosphinomethyl)-4-t-butylbenzene; 1-(2-phosphinomethyl-1,3,5,7-tetramethyl-6,9,10-trioxa-adamantyl)-2-(di-t-butylphosphinomethyl)4,5-di-(2'-phenylprop-2'-yl)benzene; 1-(2-phosphinomethyl-1,3,5,7-tetramethyl-6,9,10-trioxa-adamantyl)-2-(di-t-butylphosphinomethyl)-4-(2'-phenylprop-2'-yl)benzene; 1-(2-phosphinomethyl-1,3,5,7-tetramethyl-6,9,10-trioxa-adamantyl)-2-(di-t-butylphosphinomethyl)4,5-(di-t-butyl)benzene; 1-(2-phosphinomethyl-1,3,5,7-tetramethyl-6,9,10-trioxa-adamantyl)-2-(di-t-butylphosphinomethyl)-4-t-butyl benzene; 1-(2-phosphinomethyl-1,3,5,7-tetramethyl-6,9,10-trioxa-adamantyl)-2-(diadamantylphosphinomethyl)-4,5-di-(2'-phenylprop-2'-yl)benzene; 1-(2-phosphinomethyl-1,3,5,7-tetramethyl-6,9,10-trioxa-adamantyl)-2-(diadamantylphosphinomethyl)-4-(2'-phenylprop-2'-yl)

benzene; 1-(2-phosphinomethyl-1,3,5,7-tetramethyl-6,9,10-trioxa-adamantyl)-2-(diadamantylphosphinomethyl)-4,5-(di-t-butyl)benzene; 1-(2-phosphinomethyl-1,3,5,7-tetramethyl-6,9,10-trioxa-adamantyl)-2-(diadamantylphosphinomethyl)-4-t-butyl benzene; 1-(di-t-butylphosphinomethyl)-2-(diadamantylphosphinomethyl)-4,5-di-(2'-phenylprop-2'-yl)benzene; 1-(di-t-butylphosphinomethyl)-2-(diadamantylphosphinomethyl)-4-(2'-phenylprop-2'-yl)benzene; 1-(di-t-butylphosphinomethyl)-2-(diadamantylphosphinomethyl)-4,5-(di-t-butyl)benzene; 1-(di-t-butylphosphinomethyl)-2-(diadamantylphosphinomethyl)-4-t-butyl benzene; 1,2-bis(2-phosphinomethyl-1,3,5-trimethyl-6,9,10-trioxatricyclo-{3.3.1.1[3.7]}decyl)-4,5-di-(2'-phenylprop-2'-yl)benzene; 1,2-bis(2-phosphinomethyl-1,3,5-trimethyl-6,9,10-trioxatricyclo-{3.3.1.1[3.7]}decyl)-4-(2'-phenylprop-2'-yl)benzene; 1,2-bis(2-phosphinomethyl-1,3,5-trimethyl-6,9,10-trioxatricyclo-{3.3.1.1[3.7]}decyl)-4,5-(di-t-butyl)benzene; 1,2-bis(2-phosphinomethyl-1,3,5-trimethyl-6,9,10-trioxatricyclo-{3.3.1.1[3.7]}decyl)-4-t-butyl benzene; 1-(2-phosphinomethyl-1,3,5-trimethyl-6,9,10-trioxatricyclo-{3.3.1.1[3.7]}decyl)-2-(di-t-butylphosphinomethyl)-4,5-di-(2'-phenylprop-2'-yl)benzene; 1-(2-phosphinomethyl-1,3,5-trimethyl-6,9,10-trioxatricyclo-{3.3.1.1[3.7]}decyl)-2-(di-t-butylphosphinomethyl)-4-(2'-phenylprop-2'-yl)benzene; 1-(2-phosphinomethyl-1,3,5-trimethyl-6,9,10-trioxatricyclo-{3.3.1.1[3.7]}decyl)-2-(di-t-butylphosphinomethyl)-4,5-(di-t-butyl)benzene; 1-(2-phosphinomethyl-1,3,5-trimethyl-6,9,10-trioxatricyclo-{3.3.1.1[3.7]}decyl)-2-(di-t-butylphosphinomethyl)-4-t-butyl benzene; 1-(2-phosphinomethyl-1,3,5-trimethyl-6,9,10-trioxatricyclo-{3.3.1.1[3.7]}decyl)-2-(diadamantylphosphinomethyl)-4,5-di-(2'-phenylprop-2'-yl)benzene; 1-(2-phosphinomethyl-1,3,5-trimethyl-6,9,10-trioxatricyclo-{3.3.1.1[3.7]}decyl)-2-(diadamantylphosphinomethyl)-4-(2'-phenylprop-2'-yl)benzene; 1-(2-phosphinomethyl-1,3,5-trimethyl-6,9,10-trioxatricyclo-{3.3.1.1[3.7]}decyl)-2-(diadamantylphosphinomethyl)-4,5-(di-t-butyl)benzene; 1-(2-phosphinomethyl-1,3,5-trimethyl-6,9,10-trioxatricyclo-{3.3.1.1[3.7]}decyl)-2-(diadamantylphosphinomethyl)-4-t-butyl benzene; 1,2-bis-perfluoro(2-phosphinomethyl-1,3,5,7-tetramethyl-6,9,10-trioxatricyclo{3.3.1.1[3.7]}-decyl)-4,5-di-(2'-phenylprop-2'-yl)benzene; 1,2-bis-perfluoro(2-phosphinomethyl-1,3,5,7-tetramethyl-6,9,10-trioxatricyclo{3.3.1.1[3.7]}decyl)-4-(2'-phenylprop-2'-yl)benzene; 1,2-bis-perfluoro(2-phosphinomethyl-1,3,5,7-tetramethyl-6,9,10-trioxatricyclo{3.3.1.1[3.7]}-decyl)-4,5-(di-(t-butyl)benzene; 1,2-bis-perfluoro(2-phosphinomethyl-1,3,5,7-tetramethyl-6,9,10-trioxatricyclo{3.3.1.1[3.7]}decyl)-4-t-butyl benzene; 1,2-bis-(2-phosphinomethyl-1,3,5,7-tetra(trifluoro-methyl)-6,9,10-trioxatricyclo{3.3.1.1[3.7]}decyl)-4,5-di-(2'-phenylprop-2'-yl)benzene; 1,2-bis-(2-phosphinomethyl-1,3,5,7-tetra(trifluoro-methyl)-6,9,10-trioxatricyclo{3.3.1.1[3.7]}decyl)-4-(2'-phenylprop-2'-yl)benzene; 1,2-bis-(2-phosphinomethyl-1,3,5,7-tetra(trifluoro-methyl)-6,9,10-trioxatricyclo{3.3.1.1[3.7]}decyl)-4,5-(di-t-butyl)benzene; 1,2-bis-(2-phosphinomethyl-1,3,5,7-tetra(trifluoro-methyl)-6,9,10-trioxatricyclo{3.3.1.1[3.7]}decyl)-4-t-butyl benzene, 1,2-bis-(P-(2,2,6,6-tetramethyl-phosphinomethyl-cyclohexan-4-one)-4-(trimethylsilyl)benzene, 1-(di-tert-butylphosphinomethyl)-2-(phospha-adamantyl)-4-(trimethylsilyl)benzene, 1-(diadamantylphosphinomethyl)-2-(phospha-adamantyl)-4-(trimethylsilyl)benzene, 1-(phospha-adamantyl)-2-(phospha-adamantyl)-4-(trimethylsilyl)methylbenzene, 1-(di-tert-butylphosphinomethyl)-2-(di-tert-butylphosphino)-4-(trimethylsilyl)benzene, 1-(di-adamantylphosphinomethyl)-2-(diadamantylphosphino)-4-(trimethylsilyl)benzene, 1-(di-tert-butylphosphinomethyl)-2-(diadamantylphosphino)-4-(trimethylsilyl)benzene, 1-(di-tert-butylphosphinomethyl)-2-(P-(2,2,6,6-tetramethyl-phospha-cyclohexan-4-one)-4-(trimethylsilyl)benzene, 1-(di-tert-butylphosphinomethyl)-2-(P-(2,2,6,6-tetramethyl-phospha-cyclohexan-4-one)-4-(trimethylsilyl)benzene, 1-(2-(P-(2,2,6,6-tetramethyl-phospha-cyclohexan-4-one))-4-trimethylsilylbenzyl)-2,2,6,6-tetramethyl-phospha-cyclohexan-4-one, 1-(tert-butyl,adamantylphosphino)-2-(di-adamantylphosphinomethyl)-4-(trimethylsilyl)benzene—and wherein "phospha-adamantyl" is selected from 2-phospha-1,3,5,7-tetramethyl-6,9,10-trioxadamantyl,2-phospha-1,3,5-trimethyl-6,9,10 trioxadamantyl, 2-phospha-1,3,5,7-tetra(trifluoromethyl)-6,9,10-trioxadamantyl or 2-phospha-1,3,5-tri(trifluoromethyl)-6,9,10-trioxadamantyl-, 1-(ditertbutylphosphinomethyl)-2-(P-(2,2,6,6-tetramethyl-phospha-cyclohexan-4-one))-4-(trimethylsilyl)ferrocene, 1,2-bis(di-t-butylphosphinomethyl)-4,5-diphenyl ferrocene; 1,2-bis(di-t-butylphosphinomethyl)-4-(or 1')phenylferrocene; 1,2-bis(di-t-butylphosphinomethyl)-4,5-bis-(trimethylsilyl)ferrocene; 1,2-bis(di-t-butylphosphinomethyl)-4-(or 1')(trimethylsilyl)ferrocene; 1,2-bis(2-phosphinomethyl-1,3,5,7-tetramethyl-6,9,10-trioxa-adamantyl)-4,5-diphenylferrocene; 1,2-bis(2-phosphinomethyl-1,3,5,7-tetramethyl-6,9,10-trioxa-adamantyl) 4-(or 1')phenylferrocene; 1,2-bis(2-phosphinomethyl-1,3,5,7-tetramethyl-6,9,10-trioxa-adamantyl)-4,5-bis-(trimethylsilyl)ferrocene; 1,2-bis(2-phosphinomethyl-1,3,5,7-tetramethyl-6,9,10-trioxa-adamantyl) 4-(or 1')(trimethylsilyl)ferrocene; 1,2-bis(di-adamantylphosphinomethyl)-4,5 diphenylferrocene; 1,2-bis(di-adamantylphosphinomethyl)-4-(or 1')phenyl ferrocene; 1,2-bis(di-adamantylphosphinomethyl)-4,5 bis-(trimethylsilyl)ferrocene; 1,2-bis(di-adamantylphosphinomethyl)-4-(or 1')(trimethylsilyl)ferrocene; 1-(P,P adamantyl,t-butyl phosphinomethyl)-2-(di-t-butylphosphinomethyl)-4,5-diphenylferrocene; 1-(P,P adamantyl,t-butyl phosphinomethyl)-2-(di-t-butylphosphinomethyl)-4-(or 1')phenylferrocene; 1-(P,P adamantyl,t-butyl phosphinomethyl)-2-(di-t-butylphosphinomethyl)-4,5-bis-(trimethylsilyl)ferrocene; 1-(P,P adamantyl,t-butyl phosphinomethyl)-2-(di-t-butylphosphinomethyl)-4-(or 1')(trimethylsilyl)ferrocene; 1-(2-phosphinomethyl-1,3,5,7-tetramethyl-6,9,10-trioxa-adamantyl)-2-(di-t-butylphosphinomethyl)4,5-diphenylferrocene; 1-(2-phosphinomethyl-1,3,5,7-tetramethyl-6,9,10-trioxa-adamantyl)-2-(di-t-butylphosphinomethyl)-4-(or 1')phenyl ferrocene; 1-(2-phosphinomethyl-1,3,5,7-tetramethyl-6,9,10-trioxa-adamantyl)-2-(di-t-butylphosphinomethyl)4,5-bis-(trimethylsilyl)ferrocene; 1-(2-phosphinomethyl-1,3,5,7-tetramethyl-6,9,10-trioxa-adamantyl)-2-(di-t-butylphosphinomethyl)-4-(or 1')(trimethylsilyl)ferrocene; 1-(2-phosphinomethyl-1,3,5,7-tetramethyl-6,9,10-trioxa-adamantyl)-2-(diadamantylphosphinomethyl)-4,5-diphenyl ferrocene; 1-(2-phosphinomethyl-1,3,5,7-tetramethyl-6,9,10-trioxa-adamantyl)-2-(diadamantylphosphinomethyl)-4-(or 1')phenyl ferrocene; 1-(2-phosphinomethyl-1,3,5,7-tetramethyl-6,9,10-trioxa-adamantyl)-2-(diadamantylphosphinomethyl)-4,5-bis-(trimethylsilyl)ferrocene; 1-(2-phosphinomethyl-1,3,5,7-tetramethyl-6,9,10-trioxa-adamantyl)-2-(diadamantylphosphinomethyl)-4-(or 1')(trimethylsilyl)ferrocene; 1-(di-t-butylphosphinomethyl)-2-(diadamantylphosphinomethyl)-4,5-diphenyl ferrocene; 1-(di-t-butylphosphinomethyl)-2-(diadamantylphosphinomethyl)-4-(or 1')phenyl ferrocene; 1-(di-t-butylphosphinomethyl)-2-(diadamantylphosphinomethyl)-4,5-bis-(trimethylsilyl)ferrocene; 1-(di-t-butylphosphinomethyl)-2-(diadamantylphosphinomethyl)-4-(or 1') (trimethylsilyl)ferrocene; 1,2-bis(2-phosphinomethyl-1,3,5-trimethyl-6,9,10-trioxatricyclo-{3.3.1.1[3.7]}decyl)-4,5-diphenyl ferrocene; 1,2-bis(2-phosphinomethyl-1,3,5-trimethyl-6,9,10-trioxatricyclo-{3.3.1.1[3.7]}decyl)-4-(or 1')phenyl ferrocene; 1,2-bis(2-phosphinomethyl-1,3,5-trimethyl-6,9,10-trioxatricyclo-{3.3.1.1[3.7]}decyl)-4,5-bis-(trimethylsilyl)ferrocene; 1,2-bis(2-phosphinomethyl-1,3,5-trimethyl-6,9,10-trioxatricyclo-{3.3.1.1[3.7]}decyl)-4-(or 1') (trimethylsilyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-diphenyl ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')phenyl ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-bis-(trimethylsilyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')(trimethylsilyl)ferrocene; 1-(2-phosphinomethyl-1,3,5-trimethyl-6,9,10-trioxatricyclo-{3.3.1.1[3.7]}decyl)-2-(di-adamantylphosphinomethyl)-4,5-diphenyl ferrocene; 1-(2-phosphinomethyl-1,3,5-trimethyl-6,9,10-trioxatricyclo-{0.3.1.1[3.7]}decyl)-2-(diadamantylphosphinomethyl)-4-(or 1')phenyl ferrocene; 1-(2-phosphinomethyl-1,3,5-trimethyl-6,9,10-trioxatricyclo-{3.3.1.1[3.7]}decyl)-2-(diadamantylphosphinomethyl)-4,5-bis-(trimethylsilyl) ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')(trimethylsilyl) ferrocene; 1,2-bis-perfluoro(2-phosphinomethyl-1,3,5,7-tetramethyl-6,9,10-trioxatricyclo{3.3.1.1[3.7]}-decyl)-4,5-diphenyl ferrocene; 1,2-bis-perfluoro(2-phosphinomethyl-1,3,5,7-tetramethyl-6,9,10-trioxatricyclo{3.3.1.1[3.7]}decyl)-4-(or 1')phenyl ferrocene; 1,2-bis-perfluoro(2-phosphinomethyl-1,3,5,7-tetramethyl-6,9,10-trioxatricyclo{3.3.1.1[3.7]}-decyl)-4,5-bis-(trimethylsilyl) ferrocene; 1,2-bis-perfluoro(2-phosphinomethyl-1,3,5,7-tetramethyl-6,9,10-trioxatricyclo{3.3.1.1[3.7]}decyl)-4-(or 1')(trimethylsilyl)ferrocene; 1,2-bis-(2-phosphinomethyl-1,3,5,7-tetra(trifluoro-methyl)-6,9,10-trioxatricyclo{3.3.1.1[3.7]}decyl)-4,5-diphenyl ferrocene; 1,2-bis-(2-phosphinomethyl-1,3,5,7-tetra(trifluoro-methyl)-6,9,10-trioxatricyclo{3.3.1.1[3.7]}decyl)-4-(or 1')phenyl ferrocene; 1,2-bis-(2-phosphinomethyl-1,3,5,7-tetra(trifluoro-methyl)-6,9,10-trioxatricyclo{3.3.1.1[3.7]}decyl)-4,5-bis-(trimethylsilyl)ferrocene; 1,2-bis-(2-phosphinomethyl-1,3,5,7-tetra(trifluoro-methyl)-6,9,10-trioxatricyclo{3.3.1.1[3.7]}decyl)-4-(or 1')(trimethylsilyl)ferrocene; 1,2-bis(di-t-butylphosphinomethyl)-4,5-di-(2'-phenylprop-2'-yl) ferrocene; 1,2-bis(di-t-butylphosphinomethyl)-4-(or 1')(2'-phenylprop-2'-yl)ferrocene; 1,2-bis(di-t-butylphosphinomethyl)-4,5-di-t-butyl ferrocene; 1,2-bis(di-t-butylphosphinomethyl)-4-(or 1')t-butylferrocene; 1,2-bis(2-phosphinomethyl-1,3,5,7-tetramethyl-6,9,10-trioxa-adamantyl)-4,5-di-(2'-phenylprop-2'-yl)ferrocene; 1,2-bis(2-phosphinomethyl-1,3,5,7-tetramethyl-6,9,10-trioxa-adamantyl)-4-(or 1')(2'-phenylprop-2'-yl)ferrocene; 1,2-bis(2-phosphinomethyl-1,3,5,7-tetramethyl-6,9,10-trioxa-adamantyl)-4,5-(di-t-butyl)ferrocene; 1,2-bis(2-phosphinomethyl-1,3,5,7-tetramethyl-6,9,10-trioxa-adamantyl)-4-(or 1')t-butylferrocene; 1,2-bis(di-adamantylphosphinomethyl)-4,5-di-(2'-phenylprop-2'-yl) ferrocene; 1,2-bis(di-adamantylphosphinomethyl)-4-(or 1') (2'-phenylprop-2'-yl)ferrocene; 1,2-bis(di-adamantylphosphinomethyl)-4,5-(di-t-butyl)ferrocene; 1,2-bis(di-adamantylphosphinomethyl)-4-(or 1')t-butyl ferrocene; 1-(P,P adamantyl,t-butyl phosphinomethyl)-2-(di-t-butylphosphinomethyl)-4,5-di-(2'-phenylprop-2'-yl)ferrocene; 1-(P,P adamantyl,t-butyl phosphinomethyl)-2-(di-t-butylphosphinomethyl)-4-(or 1')(2'-phenylprop-2'-yl) ferrocene; 1-(P,P adamantyl,t-butyl phosphinomethyl)-2-(di-t-butylphosphinomethyl)-4,5-(di-t-butyl)ferrocene; 1-(P,P adamantyl,t-butyl phosphinomethyl)-2-(di-t-butylphosphinomethyl)-4-(or 1')t-butylferrocene; 1-(2-phosphinomethyl-1,3,5,7-tetramethyl-6,9,10-trioxa-adamantyl)-2-(di-t-butylphosphinomethyl)4,5-di-(2'-phenylprop-2'-yl)ferrocene; 1-(2-phosphinomethyl-1,3,5,7-tetramethyl-6,9,10-trioxa-adamantyl)-2-(di-t-butylphosphinomethyl)-4-(or 1')(2'-phenylprop-2'-yl)ferrocene; 1-(2-phosphinomethyl-1,3,5,7-tetramethyl-6,9,10-trioxa-adamantyl)-2-(di-t-butylphosphinomethyl)4,5-(di-t-butyl)ferrocene; 1-(2-phosphinomethyl-1,3,5,7-tetramethyl-6,9,10-trioxa-adamantyl)-2-(di-t-butylphosphinomethyl)-4-(or 1')t-butyl ferrocene; 1-(2-phosphinomethyl-1,3,5,7-tetramethyl-6,9,10-trioxa-adamantyl)-2-(diadamantylphosphinomethyl)-4,5-di-(2'-phenylprop-2'-yl)ferrocene; 1-(2-phosphinomethyl-1,3,5,7-tetramethyl-6,9,10-trioxa-adamantyl)-2-(diadamantylphosphinomethyl)-4-(or 1')(2'-phenylprop-2'-yl)ferrocene; 1-(2-phosphinomethyl-1,3,5,7-tetramethyl-6,9,10-trioxa-adamantyl)-2-(diadamantylphosphinomethyl)-4,5-(di-t-butyl)ferrocene; 1-(2-phosphinomethyl-1,3,5,7-tetramethyl-6,9,10-trioxa-adamantyl)-2-(diadamantylphosphinomethyl)-4-(or 1')t-butyl ferrocene; 1-(di-t-butylphosphinomethyl)-2-(diadamantylphosphinomethyl)-4,5-di-(2'-phenylprop-2'-yl)ferrocene; 1-(di-t-butylphosphinomethyl)-2-(diadamantylphosphinomethyl)-4-(or 1')(2'-phenylprop-2'-yl)ferrocene; 1-(di-t-butylphosphinomethyl)-2-(diadamantylphosphinomethyl)-4,5-(di-t-butyl)ferrocene; 1-(di-t-butylphosphinomethyl)-2-(diadamantylphosphinomethyl)-4-(or 1')t-butyl ferrocene; 1,2-bis(2-phosphinomethyl-1,3,5-trimethyl-6,9,10-trioxatricyclo-{3.3.1.1[3.7]}decyl)-4,5-di-(2'-phenylprop-2'-yl)ferrocene; 1,2-bis(2-phosphinomethyl-1,3,5-trimethyl-6,9,10-trioxatricyclo-{3.3.1.1[3.7]}decyl)-4-(or 1')(2'-phenylprop-2'-yl)ferrocene; 1,2-bis(2-phosphinomethyl-1,3,5-trimethyl-6,9,10-trioxatricyclo-{3.3.1.1[3.7]}decyl)-4,5-(di-t-butyl) ferrocene; 1,2-bis(2-phosphinomethyl-1,3,5-trimethyl-6,9,10-trioxatricyclo-{3.3.1.1[3.7]}decyl)-4-(or 1')t-butyl ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-di-(2'-phenylprop-2'-yl)ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')(2'-phenylprop-2'-yl)ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-(di-t-butyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')t-butyl ferrocene; 1-(2-phosphinomethyl-1,3,5-trimethyl-6,9,10-trioxatricyclo-{3.3.1.1[3.7]}decyl)-2-(diadamantylphosphinomethyl)-4,5-di-(2'-phenylprop-2'-yl)ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')(2'-phenylprop-2'-yl)ferrocene; 1-(2-phosphinomethyl-1,3,5-trimethyl-6,9,10-trioxatricyclo-{3.3.1.1[3.7]}decyl)-2-(diadamantylphosphinomethyl)-4,5-(di-t-butyl) ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')t-butyl ferrocene; 1,2-bis-perfluoro(2-phosphinomethyl-1,3,5,7-tetramethyl-6,9,10-trioxatricyclo{3.3.1.1[3.7]}-decyl)-4,5-di-(2'-phenylprop-2'-yl)ferrocene; 1,2-bis-perfluoro(2-phosphinomethyl-1,3,5,7-tetramethyl-6,9,10-trioxatricyclo{3.3.1.1[3.7]

}decyl)-4-(or 1')(2'-phenylprop-2'-yl)ferrocene; 1,2-bis-perfluoro(2-phosphinomethyl-1,3,5,7-tetramethyl-6,9,10-trioxatricyclo{3.3.1.1[3.7]}-decyl)-4,5-(di-t-butyl)ferrocene; 1,2-bis-perfluoro(2-phosphinomethyl-1,3,5,7-tetramethyl-6,9,10-trioxatricyclo{3.3.1.1[3.7]}decyl)-4-(or 1')t-butyl ferrocene; 1,2-bis-(2-phosphinomethyl-1,3,5,7-tetra(trifluoro-methyl)-6,9,10-trioxatricyclo{3.3.1.1[3.7]}decyl)-4,5-di-(2'-phenylprop-2'-yl)ferrocene; 1,2-bis-(2-phosphinomethyl-1,3,5,7-tetra(trifluoro-methyl)-6,9,10-trioxatricyclo{3.3.1.1[3.7]}decyl)-4-(or 1')(2'-phenylprop-2'-yl)ferrocene; 1,2-bis-(2-phosphinomethyl-1,3,5,7-tetra(trifluoro-methyl)-6,9,10-trioxatricyclo{3.3.1.1[3.7]}decyl)-4,5-(di-t-butyl)ferrocene; 1,2-bis-(2-phosphinomethyl-1,3,5,7-tetra(trifluoro-methyl)-6,9,10-trioxatricyclo{3.3.1.1[3.7]}decyl)-4-(or 1')t-butyl ferrocene.

\* \* \* \* \*